(12) United States Patent
Bertrand et al.

(10) Patent No.: US 9,403,781 B2
(45) Date of Patent: Aug. 2, 2016

(54) CRYSTALLINE 1H-1,2,3-TRIAZOL-5-YLIDENES

(75) Inventors: Guy Bertrand, Riverside, CA (US); Gregorio Gulsado-Barrios, Riverside, CA (US); Jean Bouffard, Riverside, CA (US); Bruno Donnadieu, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 582 days.

(21) Appl. No.: 13/643,262

(22) PCT Filed: Apr. 26, 2011

(86) PCT No.: PCT/US2011/033971
§ 371 (c)(1),
(2), (4) Date: Mar. 8, 2013

(87) PCT Pub. No.: WO2011/139704
PCT Pub. Date: Nov. 10, 2011

(65) Prior Publication Data
US 2013/0197178 A1 Aug. 1, 2013

Related U.S. Application Data

(60) Provisional application No. 61/328,415, filed on Apr. 27, 2010.

(51) Int. Cl.
C07D 249/06 (2006.01)
C07F 15/00 (2006.01)
B01J 31/22 (2006.01)

(52) U.S. Cl.
CPC ........... *C07D 249/06* (2013.01); *B01J 31/2295* (2013.01); *C07F 15/0033* (2013.01)

(58) Field of Classification Search
CPC .................................................. C07D 249/06
See application file for complete search history.

(56) References Cited

U.S. PATENT DOCUMENTS 6,426,419 B1 7/2002 Grubbs et al.
2005/0013150 A2 1/2005 Herrmann et al.

FOREIGN PATENT DOCUMENTS

WO 03-011455 A1 2/2003

OTHER PUBLICATIONS

Karthikeyan et al. "Palladium complexes with abnormal N-heterocyclic carbene ligands derived from 1,2,3-triazolium ions and their application in Suzuki coupling" Tetrahedron Letters, 2009, vol. 50, pp. 5834-5837.*
Matthew et al. "1,2,3-Triazolylidenes as Versatile Abnormal Carbene Ligands for Late Transition Metals" Journal of the American Chemical Society, 2008, vol. 130, pp. 13534-13535.*
Crudden et al., "Stability and reactivity of N-heterocyclic carbene complexes," Coordination Chemistry Reviews, 2004, vol. 248, pp. 2247-2273.
Karthikeyan et al., "Palladium complexes with abnormal N-heterocyclic carbene ligands derived from 1,2,3-triazolium ions and their application in Suzuki coupling," Tetrahedral Letters, 2009, vol. 50, pp. 5834-5837.
Mathew et al., "1,2,3-Triazolylidenes as Versatile Abnormal Carbene Ligands for late Transition Metals," Journal of American Chemical Society, 2008, vol. 130, 13534-13535.
International Search Report and Written Opinion, Mail date Feb. 17, 2012, PCT application No. PCT/US2011/033971, 8 pages.

* cited by examiner

*Primary Examiner* — Joseph Kosack
(74) *Attorney, Agent, or Firm* — Mintz, Levin, Cohn, Ferris, Glovsky and Popeo, P.C.

(57) ABSTRACT

The present invention provides novel and stable crystalline 1H-1,2,3 triazolium carbenes and metal complexes of 1H-1,2,3 triazolium carbenes. The present invention also provides methods of making 1H-1,2,3 triazolium carbenes and metal complexes of 1H-1,2,3 triazolium carbenes. The present invention also provides methods of using 1H-1,2,3 triazolium carbenes and metal complexes of 1H-1,2,3 triazolium carbenes in catalytic reactions.

27 Claims, 6 Drawing Sheets

CRYSTALLINE 1H-1,2,3-TRIAZOL-5-YLIDENES

CROSS-REFERENCES TO RELATED APPLICATIONS

This application claims priority benefit of U.S. Provisional Application Ser. No. 61/328,415 filed on Apr. 27, 2010, the contents of which are incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. GM068825, awarded by the National Institutes of Health, and Grant No. DE-FG02-09ER16069, awarded by the Department of Energy. The Government has certain rights in this invention.

BACKGROUND OF THE INVENTION

Neutral carbon-based $\eta^1$ ligands have previously been limited to carbon monoxide, isocyanides, and carbenes. Carbenes tend to bind more strongly to metal centers than do phosphorus-based ligands. Because of this strong carbene-metal bond, the use of carbene ligands in metal coordination complexes avoids the need for excess ligands in catalytic reactions related thereto. In addition, metal coordination complexes that include carbene ligands are often less sensitive to air and moisture and are resistant to oxidation (E. Peris, et al., *C. R. Chimie* 2003, 6, 33-37). The robustness of carbene-containing metal coordination complexes is also largely due to the presence of strong carbon-metal bonds. Based on the beneficial properties that result from strong carbon-metal bonds in carbene-containing metal coordination complexes, other types of carbon-based L ligands are desirable.

Metal coordination complexes that include carbene ligands have been known since the 1960's (K. Ofele, *J. Organomet. Chem.*, 1968, 12, P42-P43; D. J. Cardin, et al., *Chem. Rev.* 1972, 72, 545-574). Despite being known since the 1960's, the number of catalytic applications that incorporate carbenes (J. C. Y. Lin, et al., *Chem. Rev.*, 2009, 109, 3561-3598; P. L. Arnold, et al., *Chem. Rev.*, 2009, 109, 3599-3611; S. Diez-Gonzalez, et al., *Chem. Rev.*, 2009, 109, 3612-3676; M. Poyatos, et al., *Chem. Rev.*, 2009, 109, 3677-3707; C. Samojlowicz, *Chem. Rev.*, 2009, 109, 3708-3742; W. A. L. van Otterlo, et al., *Chem. Rev.*, 2009, 109, 3743-3782; S. Monfette, et al., *Chem. Rev.* 2009, 109, 3783-3816; and B. Alcaide, *Chem. Rev.*, 2009, 109, 3817-3858) has increased in large part because of the recent availability of carbenes which are stable enough to be bottled (A. Igau, et al., *J. Am. Chem. Soc.*, 1988, 110, 6463-6466; A. Igau, et al., *Angew. Chem.*, 1989, 101, 617-618; *Angew. Chem. Int. Ed.*, 1989, 28, 621-622; A. J. Arduengo III, et al., *J. Am. Chem. Soc.*, 1991, 113, 361-363; A. J. Arduengo III, et al., *J. Am. Chem. Soc.*, 1995, 117, 11027-11028; D. Enders, *Angew. Chem.*, 1995, 107, 1119-1122; *Angew. Chem. Int. Ed.*, 1995, 34, 1021-1023; M. Melaimi, et al., *Angew. Chem. Int. Ed.*, 2010, 49, 8810-8849; D. Tapu, et al., *Chem. Rev.* 2009, 109, 3385-3407; J. Vignolle, et al., *Chem. Rev.* 2009, 109, 3333-3384; F. E. Hahn, et al., *Angew. Chem.* 2008, 120, 3166-3216; *Angew. Chem. Int. Ed.*, 2008, 47, 3122-3172; Y. Canac, et al., *J. Organomet. Chem.*, 2004, 689, 3857-3865; D. Bourissou, et al., *Chem. Rev.* 2000, 100, 39-91). Carbenes, such as imidazol-2-ylidenes (U.S. Provisional Patent Application 61/393,841, filed Oct. 15, 2010) which are exemplified by compound 1 in FIG. 1, and 1,2,3-triazol-5-ylidenes (G. Guisado-Barrios, et al., *Angew. Chem. Int. Ed.*, 2010, 49, 4759-4762), which are exemplified by compound 2 in FIG. 1, are recognized for their advantageous properties as ligands for metal coordination complexes and in catalytic applications (C. Grondal, et al., *Nat. Chem.*, 2010, 2, 167-178; D. Enders, et al., *Chem. Rev.*, 2007, 107, 5606-5655; V. Nair, et al., *Chem. Soc. Rev.*, 2008, 37, 2691-2698; N. E. Kamber, et al., *Chem. Rev.*, 2007, 107, 5813-5840).

What is needed in the art are compounds of, and methods for preparing, stable mesoionic carbenes, i.e. 1,2,3-triazol-5-ylidenes. Surprisingly, the present invention meets these as well as other needs.

BRIEF SUMMARY OF THE INVENTION

In one embodiment, the present invention provides a stable mesoionic triazolium carbene compound having the structure of Formula I:

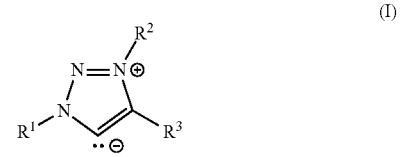

(I)

In Formula I, $R^1$, $R^2$, and $R^3$ are independently optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_3$-$C_{10}$ heterocycloalkyl, optionally substituted aryl, or optionally substituted heteroaryl. Also included are the salts of a compound of Formula I.

In a second embodiment, the present invention provides a coordination complex including a metal atom and at least one ligand selected from a compound of Formula I.

In a third embodiment, the present invention provides a reaction mixture including a compound of Formula I or a complex including a metal atom and at least one ligand selected from a compound of Formula I, a solvent and an olefin substrate, wherein said olefin substrate is selected to participate in an olefin metathesis reaction.

In a fourth embodiment, the present invention provides a method of making a compound of Formula I, the method including contacting a triazolium salt and a solvent with a Brönsted base at a temperature of from about 0 to about –100° C. and for a first reaction time of from about 5 minutes to about 20 minutes; warming and stirring the mixture of a triazolium salt in a solvent with a Brönsted base to room temperature for a second reaction time of about 10 minutes to about 60 minutes; removing the solvent under reduced pressure; extracting the product with an extracting solvent; optionally filtering the extracted product; and optionally removing the extracting solvent.

In a fifth embodiment, the present invention provides a method of catalyzing an α-arylation reaction, including combining α-arylation reactants with either a compound of Formula I or a complex including a metal atom and at least one ligand selected from a compound of Formula I under conditions sufficient for catalysis to occur.

In a sixth embodiment, the present invention provides a method of catalyzing a Suzuki coupling reaction, including combining Suzuki coupling reactants with either a compound of Formula I or a complex including a metal atom and at least one ligand selected from a compound of Formula I under conditions sufficient for catalysis to occur.

In a seventh embodiment, the present invention provides a method of catalyzing an amine arylation reaction, including combining amine arylation reactants with either a compound of Formula I or a complex including a metal atom and at least one ligand selected from a compound of Formula I under conditions sufficient for catalysis to occur.

In an eighth embodiment, the present invention provides a method for conducting olefin metathesis, including contacting an olefin substrate with either a compound of Formula I or a complex including a metal atom and at least one ligand selected from a compound of Formula I, under metathesis conditions.

In a ninth embodiment, the present invention provides a method of conducting a reaction selected from a carbon-carbon coupling reaction, a carbon-heteroatom coupling reaction or a 1,2 addition to a multiple bond, said method including contacting suitable substrates selected to undergo at least one of said reactions with either a compound of Formula I or a complex including a metal atom and at least one ligand selected from a compound of Formula I, under suitable reaction conditions.

DETAILED DESCRIPTION OF THE INVENTION

I. General

Figure 1:
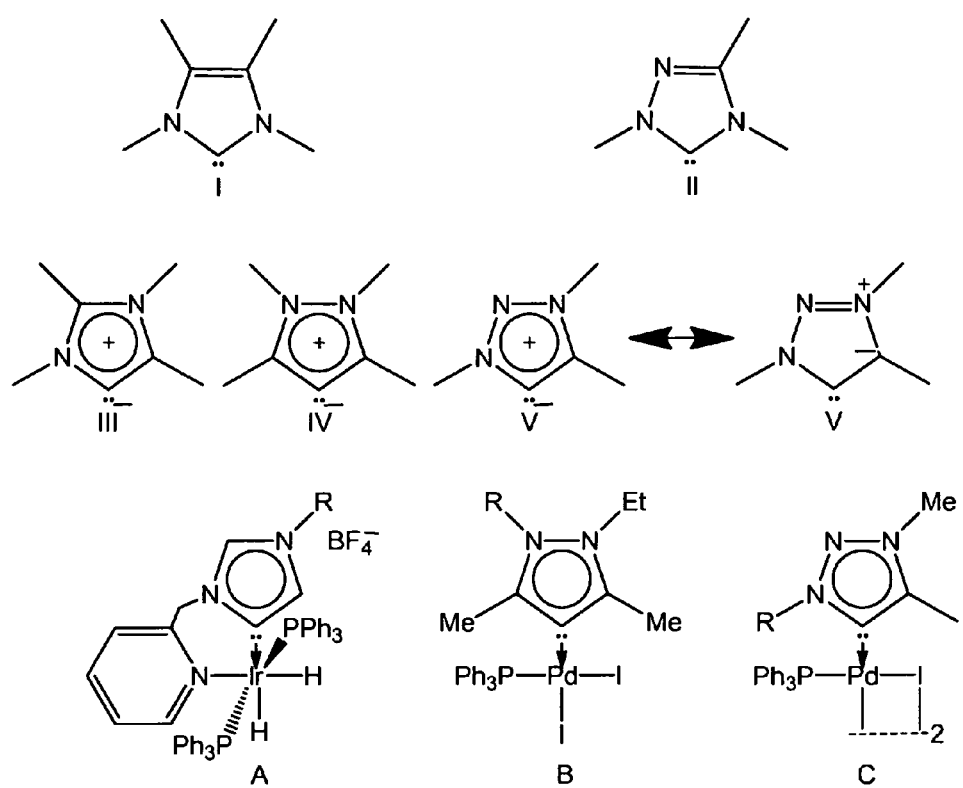
FIG. 1 shows classical N-heterocyclic carbenes, i.e. NHCs, as compounds I and II. Mesoionic carbene isomers are depicted as compounds III, IV, and V. The first reported metal complexes of mesoionic carbene isomers are depicted as compounds A, B, and C.
Figure 2:
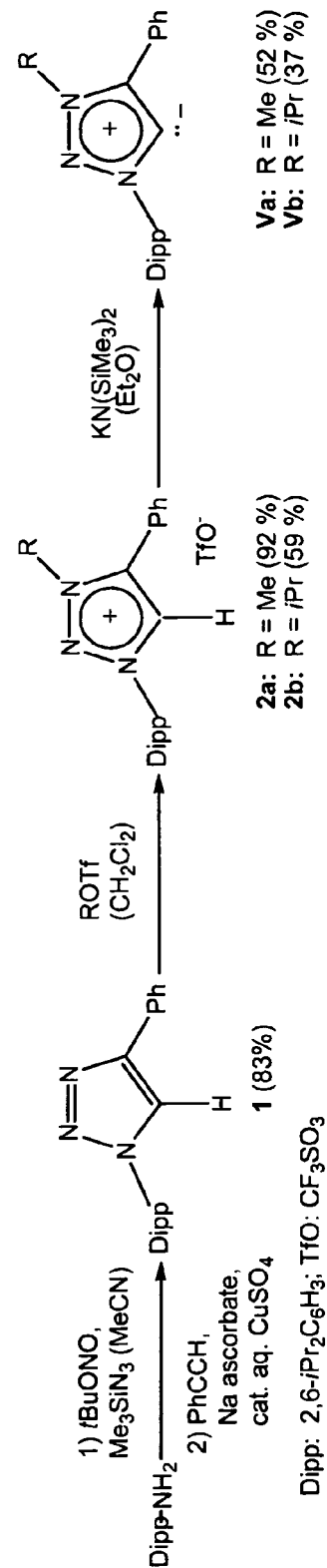
FIG. 2 shows the synthesis of the free 1,2,3-triazol-5-ylidenes, identified as compound Va and compound Vb.
Figure 3:
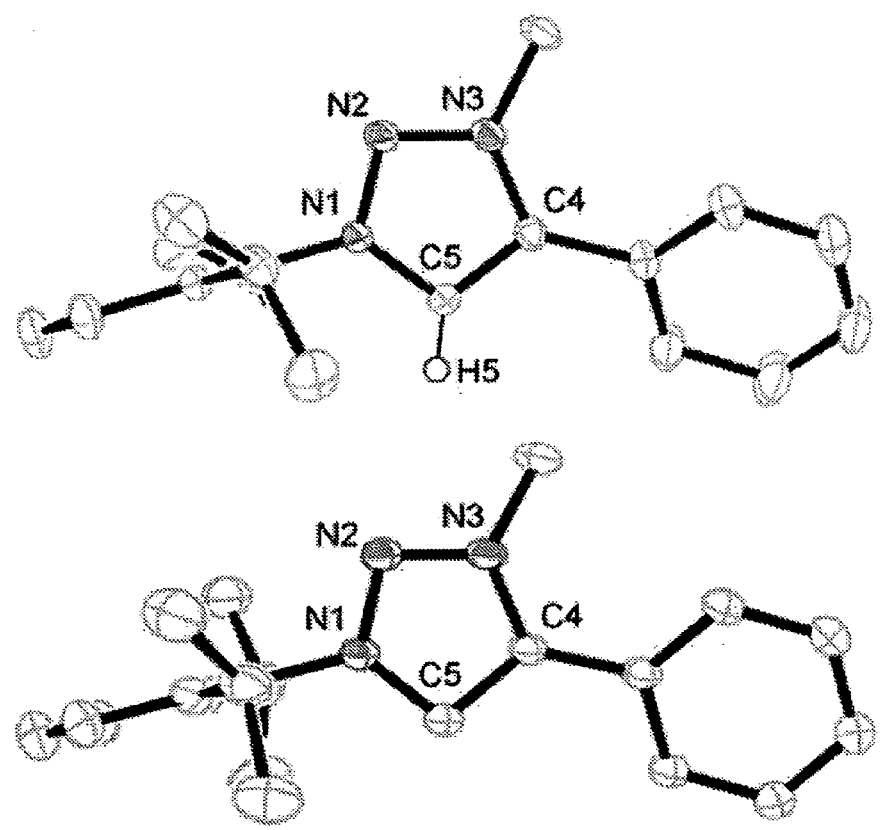
FIG. 3 shows molecular views, with 50% thermal ellipsoids shown, of compound 2a on the top and compound Va on the bottom in the solid state. Counter-ions, solvents molecules and H atoms are omitted with the exception that ring hydrogens are shown in compound 2a. Selected bond lengths (Å) and angles) (°) for compound 2a are the following: N1-N2: 1.3208(16) Å, N2-N3: 1.3183(16) Å, N3-C4: 1.3559(17) Å, C4-C5: 1.3647(19) Å, C5-N1: 1.3446(17) Å, <N1-C5-C4: 105.85(12) °; for compound Va: N1-N2: 1.3439(12) Å, N2-N3: 1.3216(13) Å, N3-C4: 1.3682(13) Å, C4-C5: 1.4053(14) Å, C5-N1: 1.3662(13) Å, <N1-C5-C4: 99.70(8) °.
Figure 4:
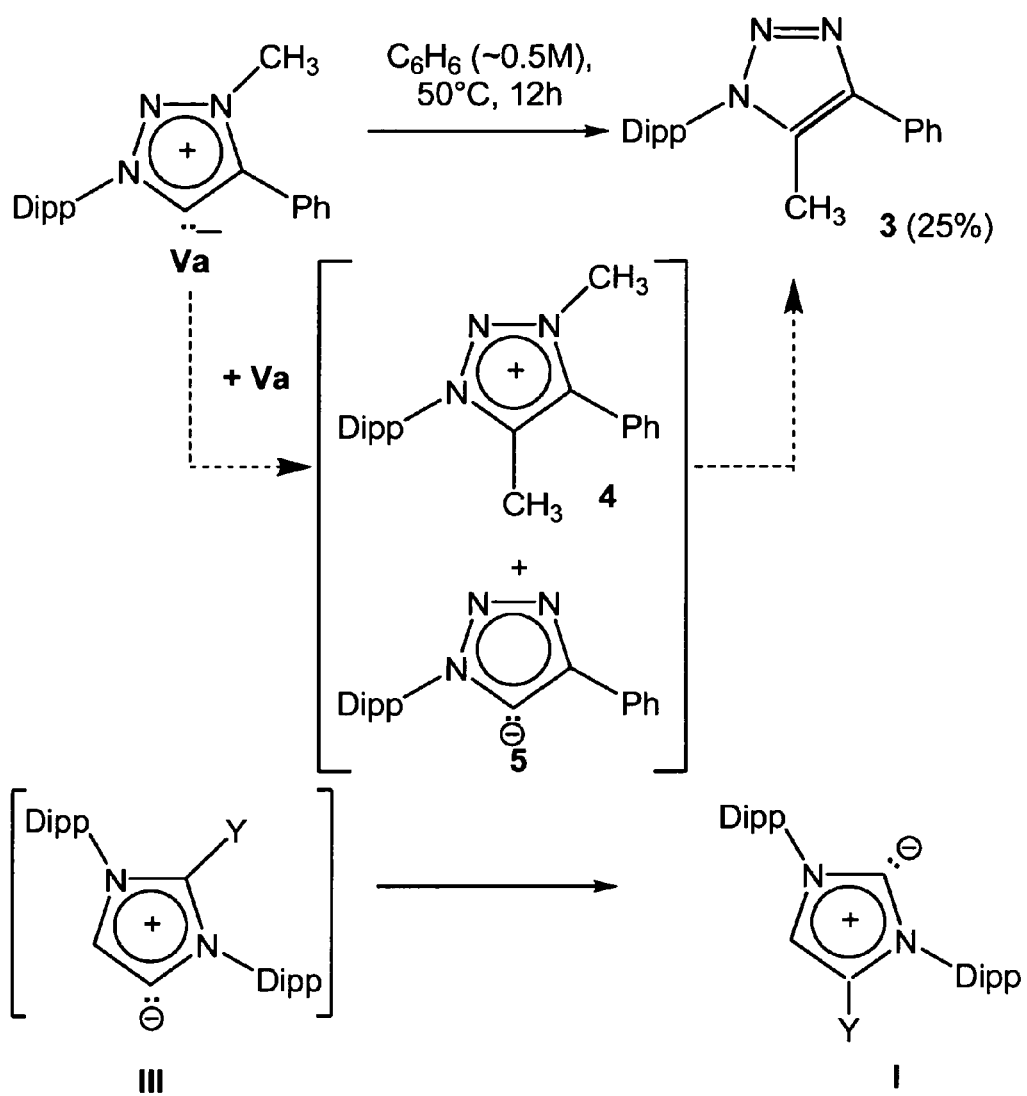
FIG. 4 shows the degradation of compound Va, free 1,2,3-triazol-5-ylidene, and the rearrangement of compound III into compound I.
Figure 5:
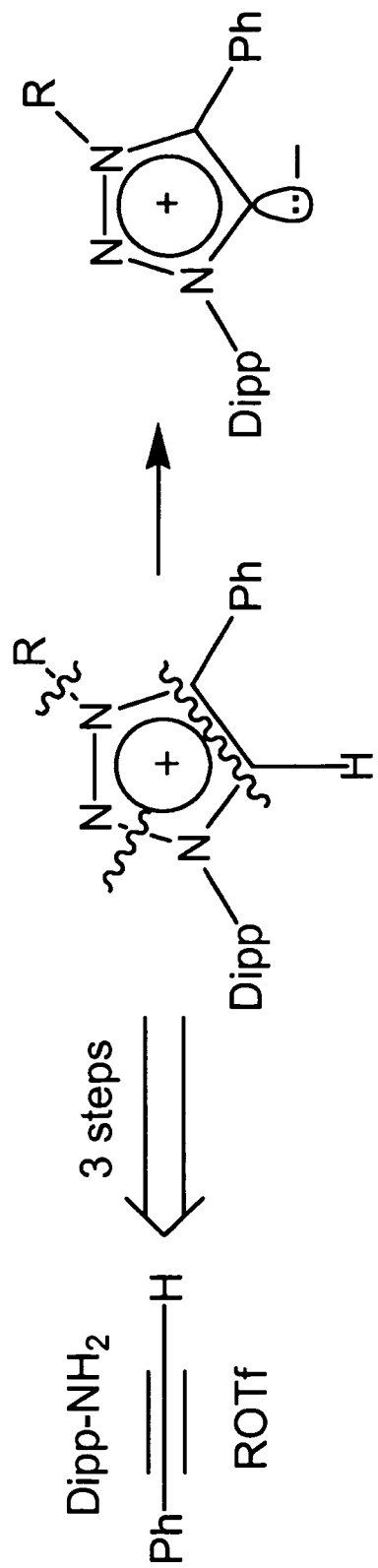
FIG. 5 shows a schematic of the modular synthesis and degradation of stable heterocycles encompassed within the scope of the present invention.

The present invention provides novel and stable crystalline 1H-1,2,3 triazolium carbenes, also known as 1H-1,2,3-triazol-5-ylidenes, and metal complexes of 1H-1,2,3 triazolium carbenes. The present invention also provides methods of making 1H-1,2,3 triazolium carbenes and metal complexes of 1H-1,2,3 triazolium carbenes. The present invention also provides methods of using 1H-1,2,3 triazolium carbenes and metal complexes of 1H-1,2,3 triazolium carbenes in catalytic reactions that include, but are not limited to, an α-arylation reaction, a Suzuki coupling reaction, a carbon-carbon coupling reaction, a carbon-heteroatom coupling reaction, a 1,2 addition to a multiple bond, an amine arylation reaction, and an olefin metathesis reaction.

II. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

As used herein, the term "carbene" refers to a class of compounds with a divalent carbon atom with a pair of lone electrons, i.e. a carbon atom that has two lone electrons and is also bonded to two other chemical entities.

As used herein, the term "triazolium carbene" refers a carbene derived from triazole. As used herein, the term "triazole" refers to a five-membered ring compound containing three nitrogen atoms in the ring. For example, the term "1,2,3-triazol-5-ylidene" refers to a five-membered ring compound wherein nitrogen atoms occupy the first, second, and third positions on the ring compound and wherein carbon atoms occupy the fourth and fifth positions on the ring compound.

As used herein, the phrase "stable mesoionic triazolium carbene" refers to a triazolium carbene that is stable and mesoionic. As used herein, the term "stable" refers to the tendency for a compound to not react under certain conditions for a certain period of time. For example, a stable triazolium carbene is a triazolium carbene that does not react for several days at about −30° C. under limited oxygen and moisture conditions. Another example of a stable triazolium carbene is a triazolium carbene that does not react for several hours at about 25° C. under limited oxygen and moisture conditions. Another example of a stable triazolium carbene is a triazolium carbene that does not react for about three days at about 25° C. under limited oxygen and moisture conditions. Another example of a stable triazolium carbene is a triazolium carbene that does not react for about ten hours at about 25° C. in benzene. As used herein, the term "mesoionic" refers to a heterocyclic compound wherein both the negative and positive charges therein are delocalized. An example of a mesoionic heterocyclic compound wherein the negative and positive charges therein are delocalized is a compound having the following structures:

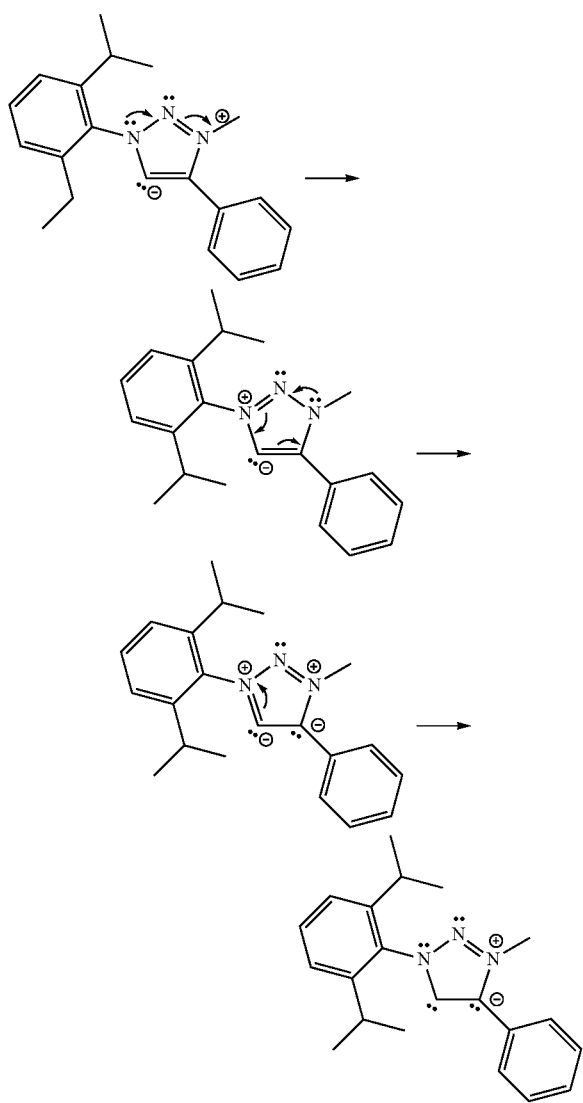

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, etc.

As used herein, the term "alkylene" refers to either a straight chain or branched alkylene of 1 to 7 carbon atoms, i.e., a divalent hydrocarbon radical of 1 to 7 carbon atoms; for instance, straight chain alkylene being the bivalent radical of Formula —$(CH_2)_n$—, where n is 1, 2, 3, 4, 5, 6 or 7. Preferably alkylene represents straight chain alkylene of 1 to 4 carbon atoms, e.g., a methylene, ethylene, propylene or butylene chain, or the methylene, ethylene, propylene or butylene chain mono-substituted by $C_1$-$C_3$-alkyl (preferably methyl) or disubstituted on the same or different carbon atoms by $C_1$-$C_3$-alkyl (preferably methyl), the total number of carbon atoms being up to and including 7. One of skill in the art will appreciate that a single carbon of the alkylene can be divalent, such as in —$(HC(CH_2)_nCH_3)$—, wherein n=0-5.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, butenyl, isobutenyl, butadienyl, pentenyl or hexadienyl.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl or butynyl.

As used herein, the term "cycloalkyl" refers to a saturated or partially unsaturated, monocyclic, fused bicyclic or bridged polycyclic ring assembly containing from 3 to 12 ring atoms, or the number of atoms indicated. For example, $C_3$-$C_8$ cycloalkyl includes cyclopropyl, cyclobutyl, cyclopentyl, cyclohexyl, cycloheptyl, and cyclooctyl. Cycloalkyl also includes norbornyl and adamantyl.

As used herein, the terms "heterocycloalkyl" and "heterocyclic" refer to a ring system having from 3 ring members to about 20 ring members and from 1 to about 5 heteroatoms such as N, O and S. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono, di, or tri substituted by one, two or three radicals selected from alkyl, alkoxy, hydroxy, halogen, cyano, amino, amino alkyl, trifluoromethyl, alkylenedioxy and oxy $C_2$-$C_3$ alkylene. Aryl also includes naphthyl and phenanthrenyl.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono or di substituted, by e.g. alkyl, nitro or halogen. Pyridyl represents 2-, 3-, or 4-pyridyl, advantageously 2- or 3-pyridyl. Thienyl represents 2- or 3-thienyl. Quinolinyl represents preferably 2-, 3-, or 4-quinolinyl. Isoquinolinyl represents preferably 1-, 3-, or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2-, 3-triazol or 1-, 2-, 4-triazolyl. Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono or di substituted.

Further to the substituents for the aryl and heteroaryl groups are varied and are selected from: halogen, OR', OC(O)R', NR'R'', SR', R', CN, $NO_2$, $CO_2$R', CONR'R'', C(O)R', OC(O)NR'R'', NR''C(O)R', NR''C(O)$_2$R', NR'C(O)NR''R''', NH C($NH_2$)=NH, NR'C($NH_2$)=NH, NH C($NH_2$)=NR', S(O)R', S(O)$_2$R', S(O)$_2$NR'R'', $N_3$, CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R'' and R''' are independently selected from hydrogen, $C_1$-$C_8$ alkyl and heteroalkyl, unsubstituted aryl and heteroaryl, (unsubstituted aryl) ($C_1$-$C_4$)alkyl, and (unsubstituted aryl)oxy($C_1$-$C_4$)alkyl.

Each of the above terms (e.g., "alkyl," "heteroalkyl," "aryl" and "heteroaryl"), when indicated as "substituted" or "optionally substituted," are meant to include both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O) NR"R"', —NR"C(O)$_2$R', —NR—C(NR'R"R"')=NR"", —NR—C(NR'R")=NR"', —S(O)R', —S(O)$_2$R', —S(O)$_2$NR'R", —NR(SO$_2$)R', —CN and —NO$_2$ in a number ranging from zero to (2 m'+1), where m' is the total number of carbon atoms in such radical. R', R", R"' and R"" are each independently selected from hydrogen, $C_1$-$C_8$ alkyl and heteroalkyl, unsubstituted aryl and heteroaryl, (unsubstituted aryl)-($C_1$-$C_4$)alkyl, and (unsubstituted aryl)oxy-($C_1$-$C_4$) alkyl. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "substituted alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O) CH$_2$OCH$_3$, and the like).

As used herein, the terms "halo" or "halogen," by themselves or as part of another substituent, mean, unless otherwise stated, a fluorine, chlorine, bromine, or iodine atom.

As used herein, the term "hydroxyl" refers to the radical having the formula OH.

As used herein, the phrase "coordinating metal ion" refers to a metal such as, but not limited to, an alkali metal, an alkaline earth metal, a transition metal such as, but not limited to, Co, Rh, Ir, Ni, Pd, Pt, Cu, Ag, and Au, which can bond to a ligand such as, but not limited to, the free-carbenes of the present application.

As used herein, the phrase "coordination complex" refers to a complex that includes a coordinating metal ion and a ligand.

As used herein, the term "ligand" refers to an ion or a molecule that bonds to a central metal atom.

As used herein, the phrase "Brönsted base" refers to a compound that is capable of bonding to a hydrogen cation, e.g. H$^+$.

As used herein, the phrase "room temperature" refers to the temperature of a laboratory under ambient conditions. For example, room temperature includes the range of from about 18° C. to about 28° C. Preferably, room temperature includes the range of from about 20° to about 25° C.

As used herein, the term "cation" refers to a positively-charged atom. For example, cation includes, but is not limited to, Li$^+$, Na$^+$, K$^+$, Rb$^+$, and Cs$^+$.

As used herein, the term "anion" refers to a negatively-charged atom. For example, anion includes, but is not limited to, F$^-$, Cl$^-$, Br$^-$, I$^-$, CN$^-$.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

As used herein, the term "isomers" refers to compounds having the same number and kind of atoms, and hence the same molecular weight, but differing in respect to the structural arrangement or configuration of the atoms.

As used herein, the term "tautomer," refers to one of two or more structural isomers which exist in equilibrium and which are readily converted from one isomeric form to another.

As used herein, the terms "a," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, or neutral conditions.

III. Compounds

The present invention provides crystalline 1H-1,2,3-Triazol-5-ylidenes and metal complexes of 1H-1,2,3-Triazol-5-ylidenes.

In some embodiments, the present invention provides a stable mesoionic triazolium carbene compound having the structure of Formula I:

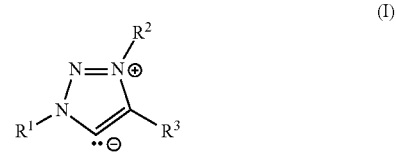

In Formula I, R$^1$, R$^2$, and R$^3$ are independently selected from optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_3$-$C_{10}$ heterocycloalkyl, optionally substituted aryl, or optionally substituted heteroaryl. Also included are the salts of compounds of Formula I.

In some embodiments, the present invention provides a compound having the structure of one of the following Formulas II-V:

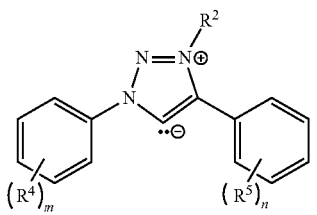

II

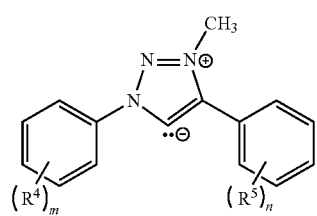

III

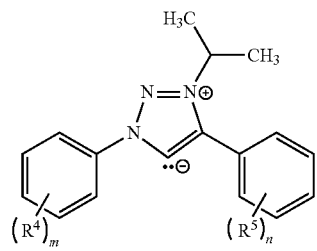

IV

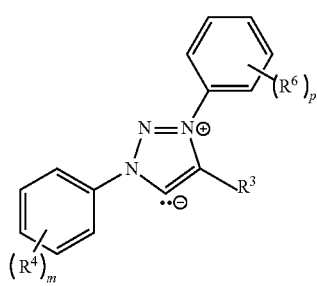

V

In Formulas II-V, $R^2$ and $R^3$ are as defined for Formula I; $R^4$, $R^5$, and $R^6$ are, in each instance, independently hydrogen, optionally substituted $C_1$-$C_6$ alkyl, optionally substituted $C_2$-$C_6$ alkenyl, optionally substituted $C_2$-$C_6$ alkynyl, halogen, or hydroxyl; subscripts m, n, and p are independently integers of from 0 to 5. Also included are the salts of compound of Formulas II-V.

In some other embodiments, the present invention provides a compound having the structure of one of the following Formulas VI-VII:

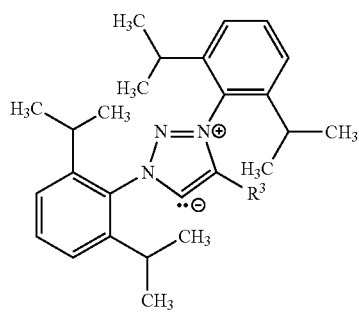

VI

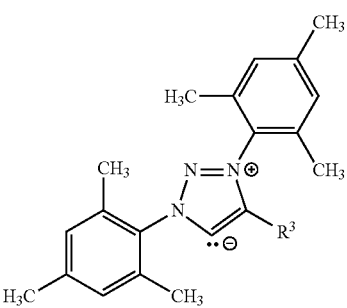

VII

In Formulas VI-VII, $R^3$ is as defined for Formula I.

In some embodiments, the present invention provides a compound of Formula wherein $R^4$ and $R^5$ are, in each instance, independently hydrogen, methyl, ethyl, propyl, isopropyl, butyl, isobutyl, halogen, or hydroxyl. In some other embodiments, $R^4$ and $R^5$ are both isopropyl and subscripts m and n are both 2. In some other embodiments, $R^4$ is isopropyl and subscript m is 2. In some embodiments, $R^5$ is isopropyl and subscript n is 2. In some other embodiments, $R^4$ and $R^5$ are both methyl and subscripts m and n are both 3. In some other embodiments, $R^4$ is methyl and subscript m is 3. In some embodiments, $R^5$ is methyl and subscript n is 3. In some other embodiments, subscripts m and n are both 0. In some embodiments, subscript m is 0. In some other embodiments, subscript n is 0. When subscript m is 0, $R^4$ is absent and the corresponding phenyl group has five hydrogen atoms bonded to it. When subscript n is 0, $R^5$ is absent and the corresponding phenyl group has five hydrogen atoms bonded to it.

In some embodiments, the present invention provides a compound of Formula V, wherein $R^4$ and $R^6$ are, in each instance, independently hydrogen, methyl, ethyl, propyl, isopropyl, butyl, isobutyl, halogen, or hydroxyl. In some other embodiments, $R^4$ and $R^6$ are both isopropyl and subscripts m and p are both 2. In some other embodiments, $R^4$ is isopropyl and subscript m is 2. In some embodiments, $R^6$ is isopropyl and subscript p is 2. In some embodiments, $R^4$ and $R^6$ are both methyl and subscripts m and p are both 3. In some other embodiments, $R^4$ is methyl and subscript m is 3. In some embodiments, $R^6$ is methyl and subscript p is 3. In some other embodiments, subscripts m and p are both 0. In some embodiments, subscript m is 0. In some other embodiments, subscript p is 0. When subscript m is 0, $R^4$ is absent and the corresponding phenyl group has five hydrogen atoms bonded to it. When subscript p is 0, $R^6$ is absent and the corresponding phenyl group has five hydrogen atoms bonded to it.

In some other embodiments, the present invention provides a compound having the structure selected from

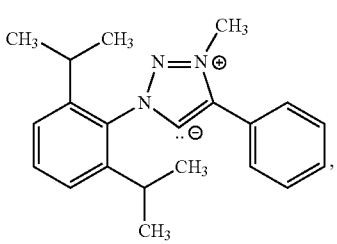

-continued
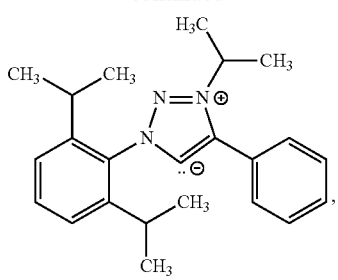
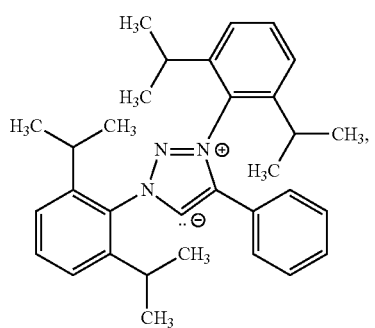
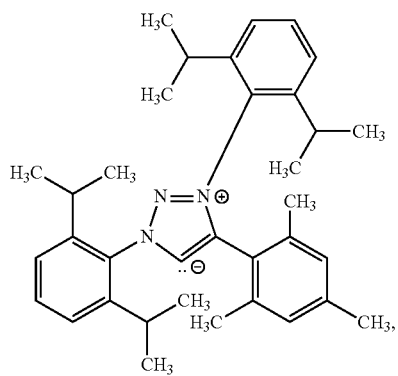
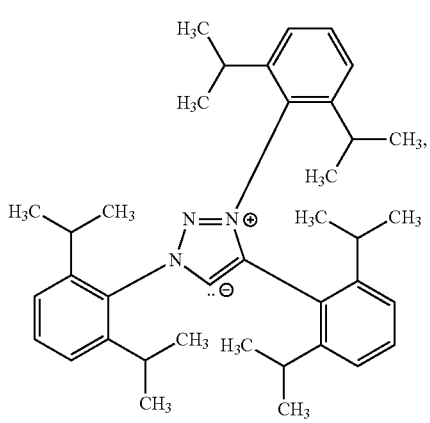
-continued
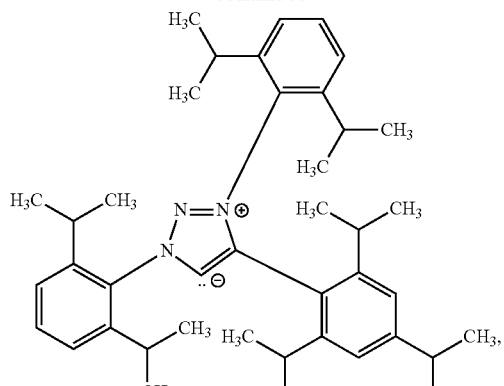
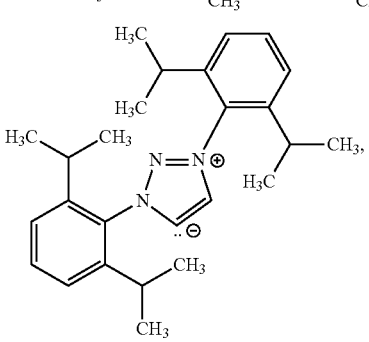
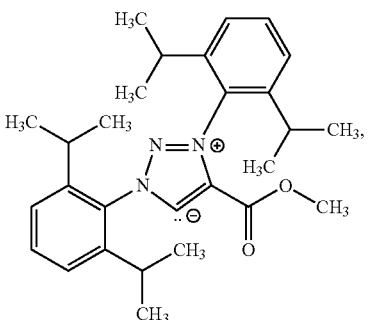
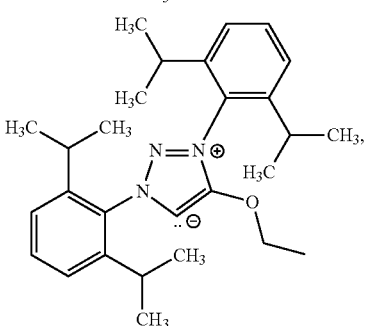
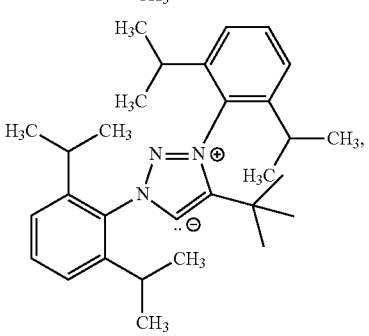

-continued
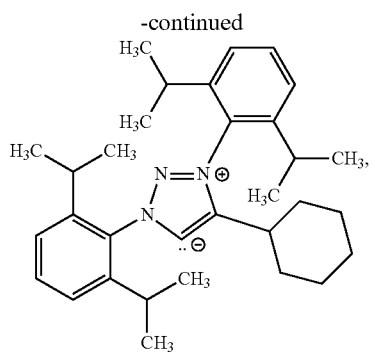
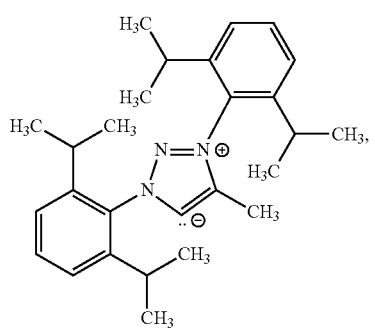
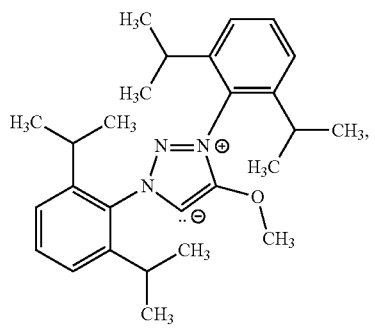
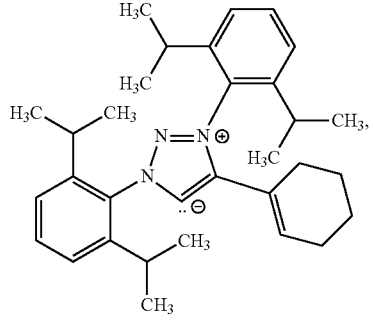
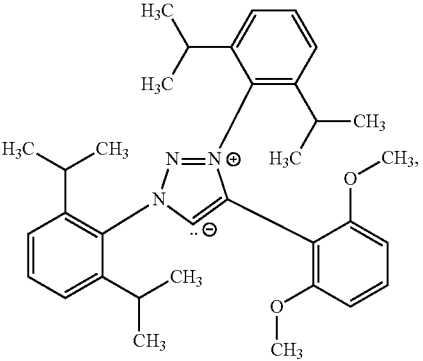
-continued
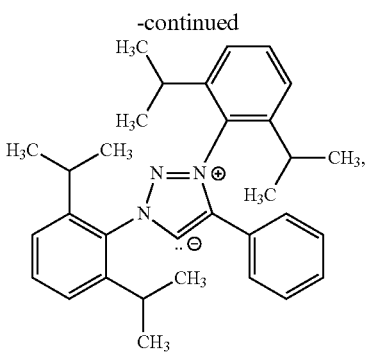
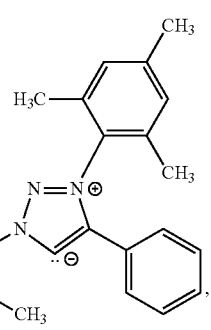
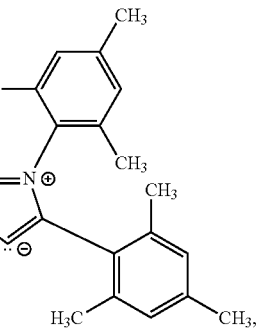
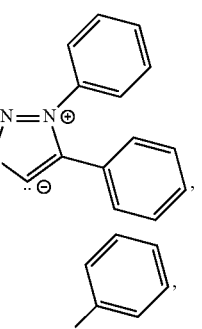
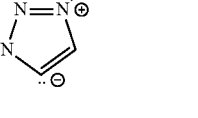
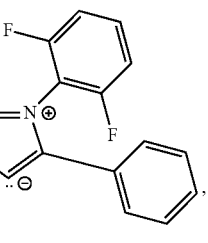

-continued

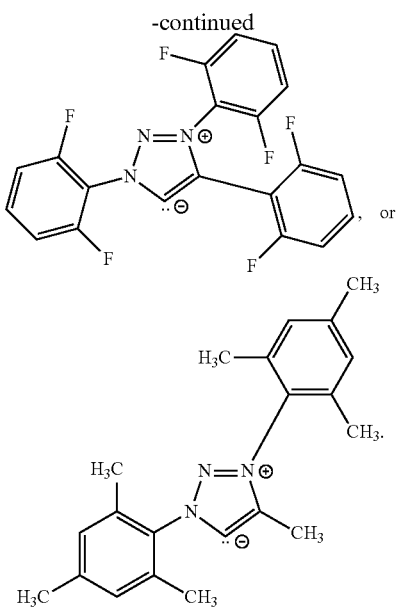, or

IV. Metal Complexes

In some embodiments, the present invention provides metal coordination complexes, including at least one ligand selected from a mesoionic triazolium carbene compounds of Formula I, that are useful as catalysts in a variety of organic reactions. One of skill in the art will appreciate that such complexes can employ a number of metals, including, but not limited to, transition metals, and have a variety of geometries (e.g., trigonal, square planar, trigonal bipyramidal and the like) depending on the nature of the metal and its oxidation state and other factors including, for example, additional ligands.

In some embodiments, the present invention provides a coordination complex including a metal atom and at least one ligand selected from a compound of Formula I. In some other embodiments, the metal atom is selected from Li, Na, K, Rb, Cs, Be, Mg, Ca, Sr, Ba, Ra, Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Ge, Sn, Pb, Sb, Bi, or Po. In some embodiments, the complex further includes at least one ligand selected from halide, pseudohalide, tetraphenylborate, perhalogenated tetraphenylborate, tetrahaloborate, hexahalophosphate, hexahaloantimonate, trihalomethanesulfonate, alkoxide, carboxylate, tetrahaloaluminate, tetracarbonylcobaltate, hexahaloferrate(III), tetrahaloferrate(III), tetrahalopalladate(II), alkylsulfonate, arylsulfonate, perchlorate, cyanide, thiocyanate, cyanate, isocyanate, isothiocyanate, amines, imines, phosphines, phosphites, carbonyl, alkenyl compounds, allyl compounds, carboxyl compounds, nitriles, alcohols, ethers, thiols or thioethers.

In some embodiments, the present invention provides a coordination complex including gold and a compound of Formula I or Formula II. In some other embodiments, the complex optionally includes a member selected from bent-allenes, phosphines, sulfonated phosphines, phosphites, phosphinites, phosphonites, arsines, stibines, ethers, ammonia, amines, amides, sulfoxides, carbonyls, nitrosyls, pyridines or thioethers.

In some other embodiments, the metal complex of the present invention includes the metal atom Ir. In some embodiments, the complex has the structure selected from

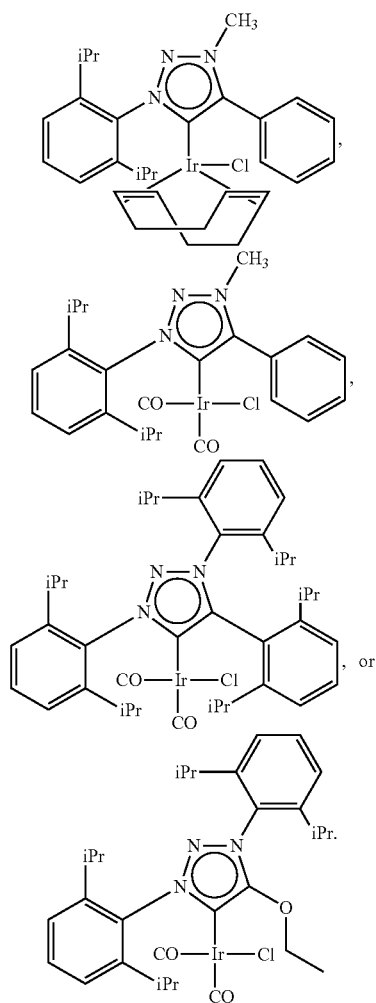

In general, any transition metal (e.g., a metal having d electrons) can be used to form the complexes/catalysts of the present invention. For example, suitable transition metals are those selected from one of Groups 3-12 of the periodic table or from the lanthanide or actinide series. Preferably, the metal will be selected from Groups 5-12 and even more preferably Groups 7-11. For example, suitable metals include platinum, palladium, iron, nickel, iridium, ruthenium and rhodium. The particular form of the metal to be used in the reaction is selected to provide, under the reaction conditions, metal centers which are coordinately unsaturated and not in their highest oxidation state.

To further illustrate, suitable transition metal complexes and catalysts include soluble or insoluble complexes of platinum, palladium, iridium, iron, rhodium, ruthenium and nickel. Palladium, rhodium, iridium, ruthenium and nickel are particularly preferred. Palladium and iridium are most preferred.

The transition metal complexes of the present invention can include additional ligands as required to obtain a stable complex. The additional ligands can be neutral ligands, anionic ligands and/or electron-donating ligands. The ligand can be added to the reaction mixture in the form of a metal complex, or added as a separate reagent relative to the addition of the metal.

Anionic ligands suitable as additional ligands are preferably halide, pseudohalide, tetraphenylborate, perhalogenated tetraphenylborate, tetrahaloborate, hexahalophosphate, hexahaloantimonate, trihalomethanesulfonate, alkoxide, carboxylate, tetrahaloaluminate, tetracarbonylcobaltate, hexahaloferrate(III), tetrahaloferrate(III) or/and tetrahalopalladate(II). Preferably, an anionic ligand is selected from halide, pseudohalide, tetraphenylborate, perfluorinated tetraphenylborate, tetrafluoroborate, hexafluorophosphate, hexafluoroantimonate, trifluoromethanesulfonate, alkoxide, carboxylate, tetrachloroaluminate, tetracarbonylcobaltate, hexafluoroferrate (III), tetrachloroferrate(III) or/and tetrachloropalladate(II). Preferred pseudohalides are cyanide, thiocyanate, cyanate, isocyanate and isothiocyanate. Neutral or electron-donor ligands suitable as additional ligands can be, for example, amines, imines, phosphines, phosphites, carbonyl, alkenyl compounds (e.g., allyl compounds), carboxyl compounds, nitriles, alcohols, ethers, thiols or thioethers. Still other suitable ligands can be carbene ligands such as the diaminocarbene ligands (e.g., NHCs).

While the present invention describes a variety of transition metal complexes useful in catalyzing organic reactions, one of skill in the art will appreciate that many of the complexes can be formed in situ. Accordingly, ligands (either carbene ligands or additional ligands) can be added to a reaction solution as a separate compound, or can be complexed to the metal center to form a metal-ligand complex prior to its introduction into the reaction solution. The additional ligands are typically compounds added to the reaction solution which can bind to the catalytic metal center. In some preferred embodiments, the additional ligand is a chelating ligand. While the additional ligands can provide stability to the catalytic transition metal complex, they may also suppress unwanted side reactions as well as enhance the rate and efficiency of the desired processes. Still further, in some embodiments, the additional ligands can prevent precipitation of the catalytic transition metal. Although the present invention does not require the formation of a metal-additional ligand complex, such complexes have been shown to be consistent with the postulate that they are intermediates in these reactions and it has been observed the selection of the additional ligand has an affect on the course of the reaction.

In related embodiments, the present invention provides metal complexes, of the type described above, in which the carbene ligand has a pendent functionalized side chain (e.g., aminoalkyl, mercaptoalkyl, acyloxyalkyl, a second carbene and the like) in which the functional group acts as a ligand to provide a bidentate ligand feature. In still other embodiments, the carbene ligand forms a metal complex with bidentate ligands that are not tethered to the cyclic carbene moiety.

In some embodiments, the present invention provides a reaction mixture including a coordination complex including a metal atom and at least one ligand selected from a carbene compound of Formula I, a solvent and an olefin substrate, wherein said olefin substrate is selected to participate in an olefin metathesis reaction. In some other embodiments, the olefin substrate is selected as a substrate for ring closing metathesis. In some embodiments, the olefin substrate is selected as a substrate for ring opening polymerization metathesis. In some other embodiments, the olefin substrate is selected as a substrate for cross metathesis. In some embodiments, the olefin substrate is selected as a substrate for acyclic diene polymerization metathesis.

V. Methods of Making the Compounds and Complexes of the Present Invention

The present invention provides methods of making and using the compounds having the structure of Formulas I through IV. See G. Guisado-Barrios, et al., "Crystalline 1H-1,2,3-Triazol-5-ylidenes: New Stable Mesoionic Carbenes (MICs)", *Angew. Chem. Int. Ed.,* 2010, 49, 4759-4762, which is incorporated herein by reference in its entirety.

In some embodiments, the present invention provides a method of making a compound of Formula I, the method including contacting a triazolium salt and a solvent with a Brönsted base at a temperature of from about 0 to about −100° C. and for a first reaction time of from about 5 minutes to about 20 minutes; warming and stirring the mixture of a triazolium salt in a solvent with a Brönsted base to room temperature for a second reaction time of about 10 minutes to about 60 minutes; removing the solvent under reduced pressure; extracting the product with an extracting solvent; optionally filtering the extracted product; and optionally removing the extracting solvent. In some embodiments, the triazolium salt has the structure of Formula VIII:

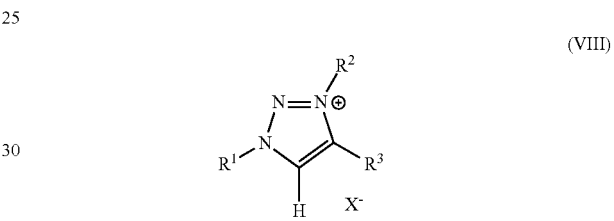

In Formula VIII, $R^1$, $R^2$, and $R^3$ are independently selected from substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_3$-$C_{10}$ heterocycloalkyl, optionally substituted aryl, or optionally substituted heteroaryl. X is an anion selected from fluoro, chloro, bromo, iodo, trifluoromethanesulfonate, chlorate, acetate, cyanide, thiocynate, oxalate, tetrafluoroborate, nitrate, nitrite, sulfate, sulfite, phosphate, carboxylate, $PbF_4^-$, or $SbF_6^-$. In some other embodiments, the triazolium salt has the structure selected from

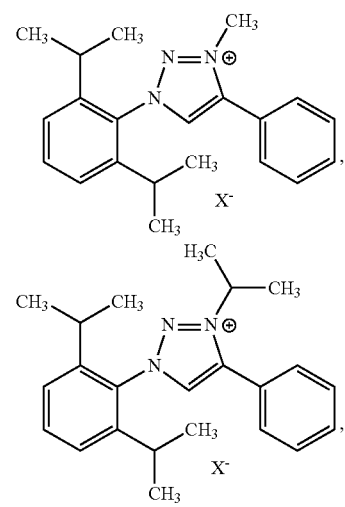

-continued
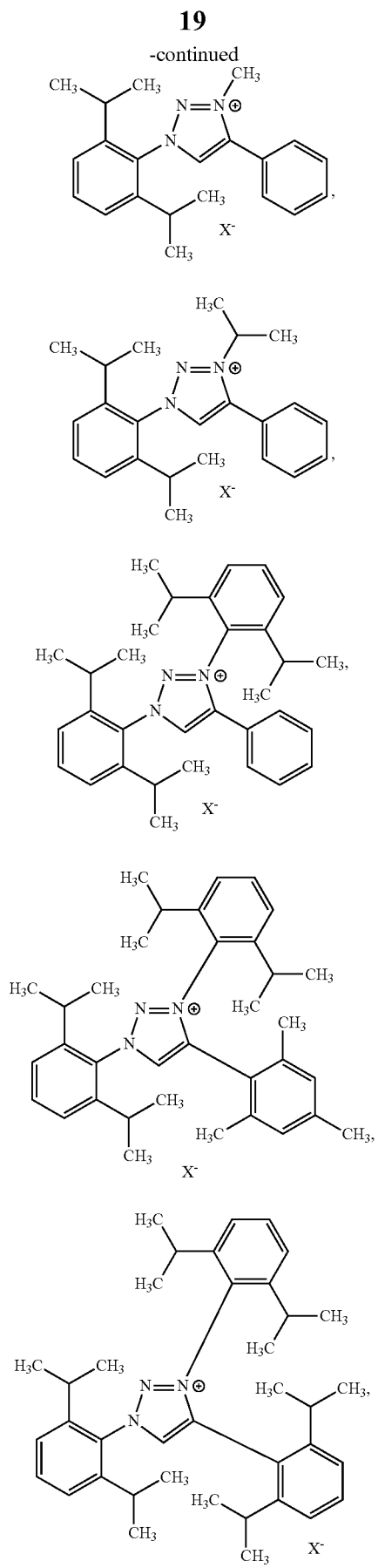
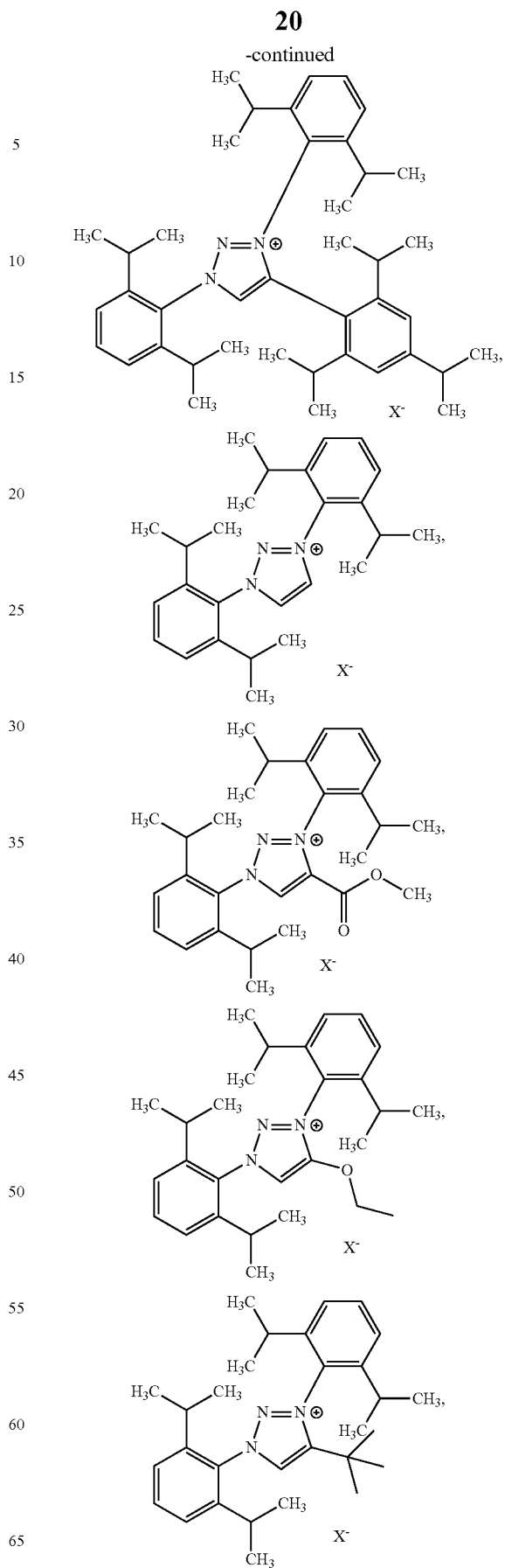

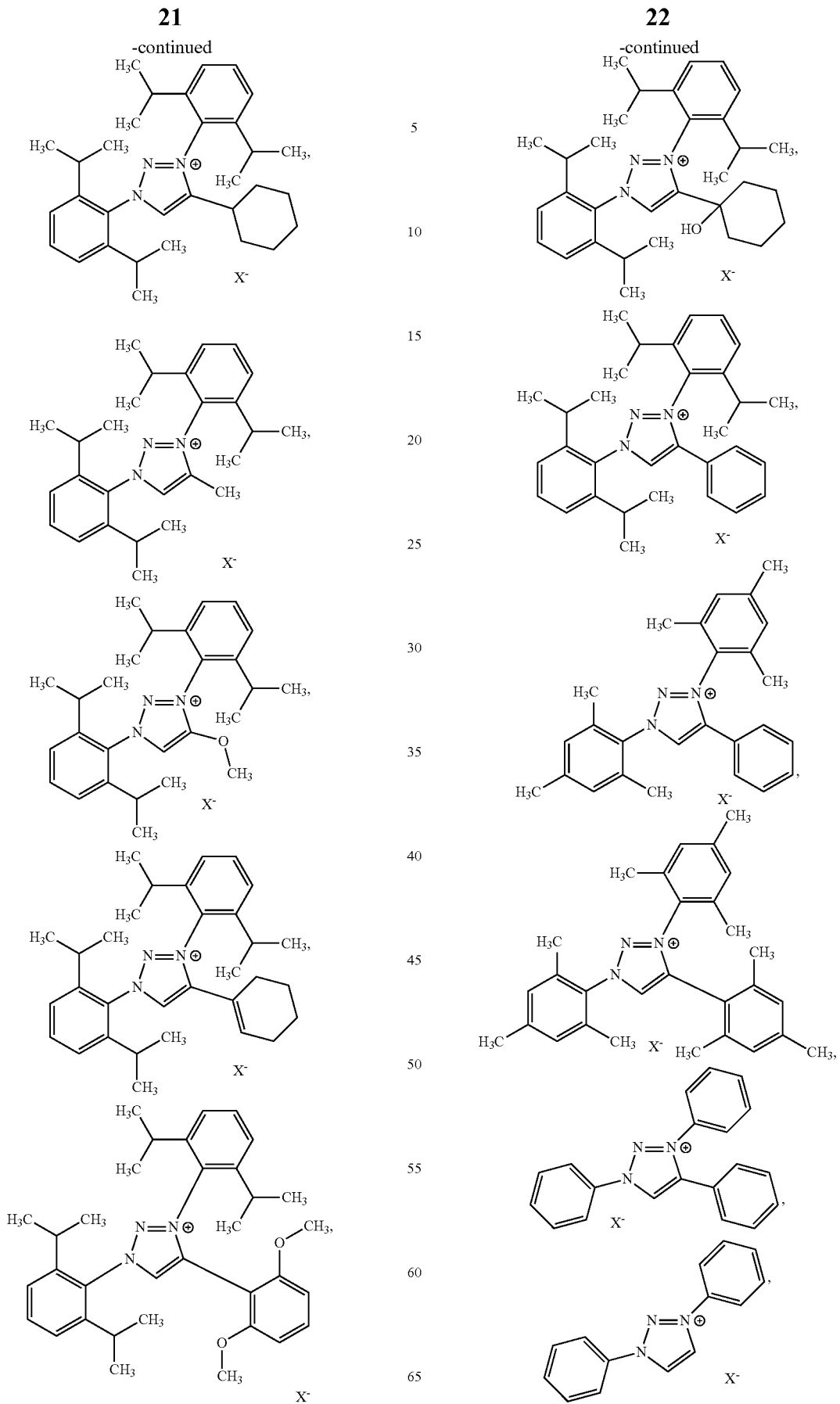

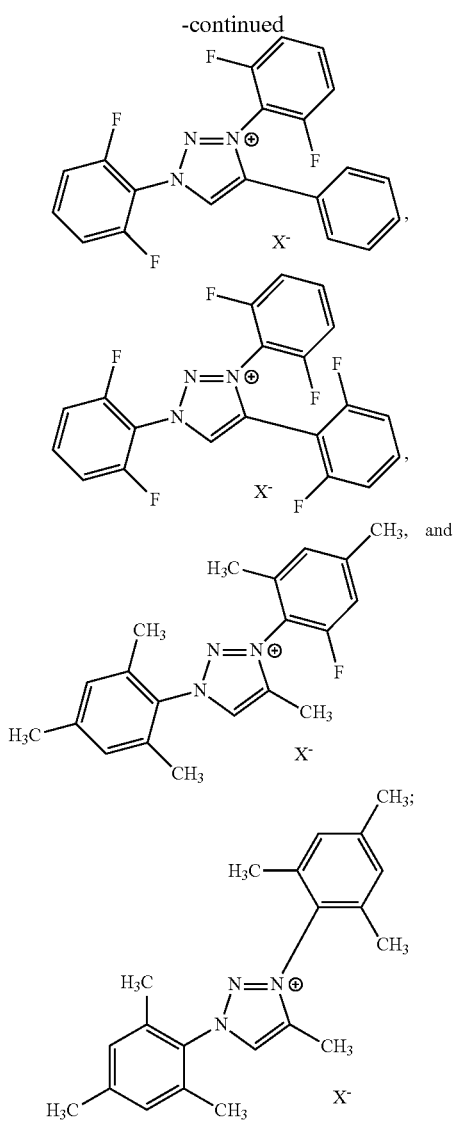

wherein X is an anion selected from the group consisting of fluoro, chloro, bromo, iodo, trifluoromethanesulfonate, chlorate, acetate, cyanide, thiocynate, oxalate, tetrafluoroborate, nitrate, nitrite, sulfate, sulfite, phosphate, carboxylate, $PbF_4^-$, and $SbF_6^-$.

In some embodiments, the Brönsted base is selected from lithium diisopropylamide, potassium bis(trimethylsilyl) amide, potassium hexamethyldisilazide, or potassium tert-butoxide. In some other embodiments the contacting of a triazolium salt in a solvent with a Brönsted base occurs at a temperature of approximately −78° C. In some embodiments, the first reaction time is about 10 minutes. In some other embodiments, the second reaction time is about 50 minutes. In some embodiments, the solvent is selected from anhydrous diethyl ether or tetrahydrofuran. In some other embodiments, the extracting solvent is selected from hexane, anhydrous hexane, diethyl ether, benzene, toluene or combinations thereof. In some embodiments, the extracting solvent is anhydrous hexane. In some other embodiments, the extracting solvent is benzene. In yet other embodiments, the extracting solvent is toluene.

Brönsted bases suitable for use with the present invention include, but are not limited to, those bases that include cations selected from rows 3, 4, and 5 of the periodic table. In other embodiments, the Brönsted base includes, but is not limited to, a base that includes a cation selected from rows 3 and 4 of the periodic table. In some other embodiments, the cation component to a Brönsted base is potassium, sodium, magnesium, cesium, calcium or barium. In other embodiments, the cation associated with a Brönsted base is sodium or potassium. In some other embodiments, the cation is potassium. Examples of specific Brönsted bases that are suitable for use with the present invention include, but are not limited to, potassium bis(trimethylsilyl)amide, sodium bis(trimethylsilyl)amide, potassium hydride, sodium hydride, sodium and potassium alkoxides (e.g., sodium methoxide, sodium tert-butoxide, potassium tert-butoxide), sodium and potassium aryloxides and derivatives thereof. In other embodiments, the Brönsted bases suitable for use with the present invention include, but are not limited to, potassium bis(trimethylsilyl) amide, sodium bis(trimethylsilyl)amide, potassium hydride and sodium hydride.

VI. Catalytic Reactions Suitable for Use with the Compounds and Complexes of the Present Invention As noted above, the compounds and complexes of the present invention are useful in catalyzing a variety of synthetic organic reactions including amine arylation reactions, Suzuki coupling reactions (aryl-aryl or aryl-alkyl coupling reactions), and α-arylation reactions. Still other reactions that can benefit from the above-noted compounds and complexes include, for example, hydrogenation, hydroformylation (of alkenes and alkynes), hydrosilylation (of alkenes, alkynes, ketones and aldehydes), metathesis (olefin (ring closing, cross metathesis, ring opening metathesis, ring opening metathesis polymerization) ene-yne), carbonylation, hydroarylation and hydroamination.

The reactions of the present invention can be performed under a wide range of conditions, and the solvents and temperature ranges recited herein should not be considered limiting. In general, it is desirable for the reactions to be run using mild conditions which will not adversely affect the reactants, the catalyst, or the product. For example, the reaction temperature influences the speed of the reaction, as well as the stability of the reactants and catalyst. The reactions will typically be run at temperatures in the range of 25° C. to 300° C., more preferably in the range 25° C. to 150° C.

Additionally, the reactions are generally carried out in a liquid reaction medium, but in some instances can be run without addition of solvent. For those reactions conducted in solvent, an inert solvent is preferred, particularly one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform; dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

In some embodiments, reactions utilizing the catalytic complexes of the present invention can be run in a biphasic mixture of solvents, in an emulsion or suspension, or in a lipid vesicle or bilayer. In certain embodiments, the catalyzed reactions can be run in the solid phase with one of the reactants tethered or anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, making a derivative of one or more of the substituents of the aryl group.

In some embodiments, the present invention provide a method of catalyzing an α-arylation reaction, including combining α-arylation reactants with either a carbene compound of Formula I or a coordination complex including a metal atom and at least one ligand selected from a carbene compound of Formula I, under conditions sufficient for catalysis to occur.

In some other embodiments, the present invention provide a method of catalyzing a Suzuki coupling reaction, including combining Suzuki coupling reactants with either a carbene compound of Formula I or a coordination complex including a metal atom and at least one ligand selected from a carbene compound of Formula I under conditions sufficient for catalysis to occur.

In some embodiments, the present invention provides a method of catalyzing an amine arylation reaction, including combining amine arylation reactants with either a carbene compound of Formula I or a coordination complex including a metal atom and at least one ligand selected from a carbene compound of Formula I under conditions sufficient for catalysis to occur.

In some other embodiments, the present invention provides a method for conducting olefin metathesis, including contacting an olefin substrate with either a carbene compound of Formula I or a coordination complex including a metal atom and at least one ligand selected from a carbene compound of Formula I, under metathesis conditions. In some embodiments, the olefin substrate is selected as a substrate for ring closing metathesis. In some other embodiments, the olefin substrate is selected as a substrate for ring opening polymerization metathesis. In some embodiments, the olefin substrate is selected as a substrate for cross metathesis. In some other embodiments, the olefin substrate is selected as a substrate for acyclic diene polymerization metathesis.

In some embodiments, the present invention provides a method of conducting a reaction selected from a carbon-carbon coupling reaction, a carbon-heteroatom coupling reaction or a 1,2 addition to a multiple bond, said method including contacting suitable substrates selected to undergo at least one of said reactions with either a carbene compound of Formula I or a coordination complex including a metal atom and at least one ligand selected from a carbene compound of Formula I, under suitable reaction conditions. In some embodiments, the reaction is a carbon-carbon coupling reaction and said suitable conditions include an organic solvent and a temperature of from −30° C. to 190° C. In some embodiments, the reaction is a carbon-heteroatom coupling reaction and said suitable conditions include an organic solvent and a temperature of from −30° C. to 190° C. In some embodiments, the reaction is a 1,2-addition to a multiple bond and said suitable conditions include an organic solvent and a temperature of from −30° C. to 190° C.

VII. Examples

Materials. Unless otherwise noted, all reagents including solvents were obtained from commercial suppliers and used directly without further purification. Anhydrous THF and $Et_2O$ were obtained after distillation over sodium benzophenone ketyl under an argon atmosphere. Anhydrous PhMe was obtained after distillation over sodium under an argon atmosphere. Anhydrous PhH and hexane were obtained after distillation over potassium. Anhydrous $CH_2Cl_2$ and $CH_3CN$ were obtained after distillation over calcium hydride under an argon atmosphere. Column chromatography was performed with silica gel (32-63 μM).

General methods, instrumentation and measurements. Synthetic manipulations that required an inert atmosphere, unless otherwise noted, were carried out in flame-dried glassware equipped with magnetic agitators under argon using standard Schlenk techniques or in an inert-atmosphere glovebox. $^1H$ and $^{13}C$ NMR spectra were recorded on either a 300 or a 400 MHz spectrometers. The chemical shift data for each signal are given in units of 0 (ppm) relative to tetramethylsilane (TMS) where 0 (TMS)=0, and referenced to the residual solvent resonances. Splitting patterns are denoted as s (singlet), d (doublet), t (triplet), q (quartet), sept (septet), m (multiplet), and br (broad). Infrared spectra were recorded on Bruker Equinox 55 FTIR spectrometer. High-resolution mass spectra (HR-MS) were acquired on LC-TOF instrument using electro spray ionization mode (ESI). Melting points (open or sealed capillaries) are reported without correction.

Example 1

Synthesis of 2-Azido-1,3-diisopropylbenzene 2,6-Diisopropylphenyl azide was prepared following the protocol of Barral, K., et al. *Org. Lett.* 2007, 9, 1809-1811. 2,6-Diisopropylaniline (2.76 g, 16 mmol) was dissolved in $CH_3CN$ (10 ml) in a 50-mL round-bottomed flask and cooled to 0° C. in an ice bath. To this mixture was added t-BuONO (2.42 g, 47 mmol), followed by $Me_3SiN_3$ (2.17 g, 18 mmol) dropwise. The mixture was allowed to warm to room temperature while stirring for 1 hour. The reaction leading to the formation of 2,6-diisopropylphenyl azide is highly exothermic following a variable induction period, which can lead to runaway reaction and pose a safety hazard (explosion). Consequently, caution is advised when performing this reaction, especially on a large scale. In particular, even when the reaction is performed at room temperature, it should be conducted with a large heat sink, e.g. flask immerged in a water bath at room temperature, and with efficient heat transfer, e.g. rapid and efficient stirring, oversized glassware. After evaporation of the solvent, the crude mixture was purified by silica gel chromatography using hexane as the mobile phase to yield 2,6-diisopropylphenyl azide as a yellowish oil (2.1 g, 64%). $^1$H-NMR (CDCl$_3$, 25° C., 300 MHz): δ=7.19 (m, 3H, H$_{ar}$), 3.38 (sept, 2H, J=6.84 Hz), 1.38 ppm (d, 12H, CH(CH$_3$)$_2$, J=6.9 Hz); $^{13}$C-NMR (CDCl$_3$, 25° C., 75 MHz): δ=143.3, 135.6, 127.1, 124.2, 29.0, 23.1 ppm. IR(CH$_2$Cl$_2$): v=2126.31 cm$^{-1}$. Characterization data for 2,6-diisopropylphenyl azide are consistent with literature values (Spencer, L. P., et al. *Organometallics*, 2003, 22, 3841-3854; Pilyugina, T. S., et al., *Organometallics*, 2005, 24, 1929-1937).

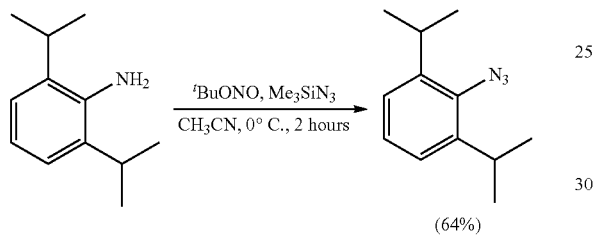

(64%)

Example 2

Synthesis of 1-(2,6-Diisopropylphenyl)-4-phenyl-1H-1,2,3-triazole

Triazole, identified as compound 1 below, was prepared following the protocol of Barral, K.; et al., *Org. Lett.* 2007, 9, 1809-1811. 2,6-Diisopropylaniline (5.56 g, 31 mmol) was dissolved in CH$_3$CN (20 ml) in a 50-mL round bottomed flask. t-BuONO (4.85 g, 47 mmol) and Me$_3$SiN$_3$ (4.34 g, 37 mmol) were sequentially added dropwise at 0° C., and stirring was maintained for two hours without removing the ice bath. The reaction leading to the formation of 2,6-diisopropylphenyl azide is highly exothermic following a variable induction period, which can lead to runaway reaction and pose a safety hazard (explosion). Consequently, caution is advised when performing this reaction, especially on a large scale. In particular, even when the reaction is performed at room temperature, it should be conducted with a large heat sink, e.g. flask immerged in a water bath at room temperature, and with efficient heat transfer, e.g. rapid and efficient stirring, oversized glassware. Phenylacetylene (4.74 g, 47 mmol), and a mixture of CuSO$_4$.5H$_2$O (0.79 g, 3.1 mmol) and sodium ascorbate (3.09 g, 15 mmol) in water (10 ml) were then added. The reaction mixture was allowed to slowly warm to room temperature while stirring overnight. The reaction was quenched by adding an excess of concentrated aqueous NH$_4$OH and the resulting mixture was stirred overnight. The product was extracted with CH$_2$Cl$_2$ and the combined organic fractions were dried over anhydrous MgSO$_4$. After evaporation of the solvent, the crude product was washed with hexane, to yield compound 1 as white solid (7.90 g, 83%). m.p. 176-177° C.; $^1$H-NMR (CDCl$_3$, 25° C., 300 MHz): δ=7.96 (d, 2H, H$_{ar}$, J=7.5 Hz) 7.91 (s, 1H, H$_{trz}$), 7.49 (3H, m), 7.41 (1H, d, H$_{ar}$, J=7.3 Hz), 7.33 (2H, d, H$_{ar}$, J=7.8 Hz), 2.36 (sept, 2H, J=6.8 Hz), 1.18 (d, 12H, CH(CH$_3$)$_2$, J=6.8 Hz); $^{13}$C-NMR (CDCl$_3$, 75 MHz) δ: 147.6, 146.3, 133.6, 131.0, 130.5, 129.1, 128.5, 125.9, 124.02, 122.6, 28.6, 24.4, 24.2; HR-MS (ESI): m/z calcd. for C$_{20}$H$_{23}$N$_3$ [M+H]$^+$ 306.1965. found 306.1958.

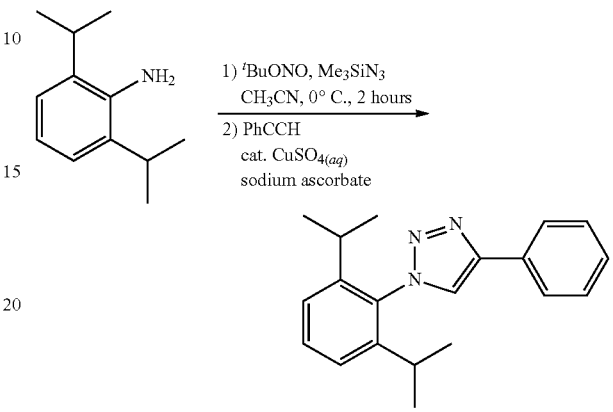

1 (83%)

Example 3

Synthesis of 1-(2,6-diisopropylphenyl)-3-methyl-4-phenyl-1H-1,2,3-triazolium trifluoromethanesulfonate To a solution of the triazole, identified as compound 1, (1.79 mmol, 0.5 g) in anhydrous DCM (20 mL) at −78° C. was added methyl trifluoromethanesulfonate (1.96 mmol, 0.32 g) dropwise. The reaction mixture was stirred overnight as it was allowed to warm to room temperature. The solvent was evaporated, and a white solid was obtained that was washed with diethyl ether and filtered to afford the compound, identified as compound 2a below, as a white solid (0.773 g; 92%). Crystals suitable for X-ray analysis were obtained by the vapor diffusion of Et$_2$O into a solution of compound 2a in CH$_2$Cl$_2$. m.p. 158-160° C.; $^1$H-NMR (CDCl$_3$, 25° C., 300 MHz): δ=8.62 (s, 1H, H$_{trz}$), 7.87 (d, 2H, H$_{ar}$, J=7.3 Hz), 7.60 (d, 4H, H$_{ar}$, J=7.9 Hz), 7.38 (d, 2H, H$_{ar}$, J=7.8 Hz), 4.44 (s, 3H), 2.34 (sept, 2H J=6.75 Hz), 1.21 (d, 6H, CH(CH$_3$)$_2$ J=6.4 Hz). 1.19 (d, 6H, CH(CH$_3$)$_2$ J=6.4 Hz). $^{13}$C NMR (CDCl$_3$, 25° C., 75 MHz): δ=145.7, 144.6, 133.1, 132.3, 130.9 (CH$_{trz}$), 130.7, 130.0, 129.9, 124.8, 121.4, 39.8, 28.9, 24.5, 23.9; HR-MS (ESI) m/z calcd. for C$_{21}$H$_{26}$N$_3$ [M+H]$^+$ 320.2121. found 320.2116.

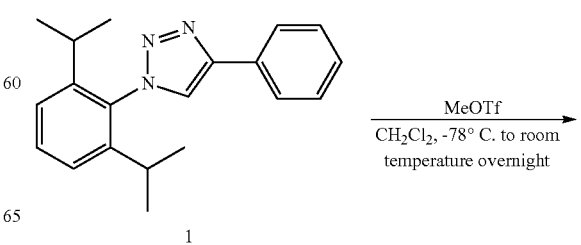

1

-continued

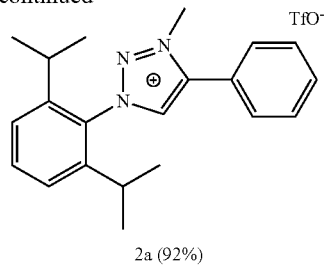

2a (92%)

Example 4

Synthesis of 1-(2,6-diisopropylphenyl)-3-(2-propyl)-4-phenyl-1H-1,2,3 triazolium trifluoromethanesulfonate In a first Schlenk flask was prepared isopropyl trifluoromethanesulfonate according to the method of Fernandez-Rodriguez, M. A., et al., *Organometallics*, 2009, 28, 361-369. To a solution of isopropanol (0.5 mL, 6.55 mmol) and pyridine (0.53 mL, 6.55 mmol) in anhydrous $CH_2Cl_2$ (20 mL) at −20° C. was added trifluoromethanesulfonic anhydride (1.10 ml, 6.55 mmol) dropwise. Contents were stirred at −20° C. for 30 minutes, followed by another 30 minutes at room temperature. Anhydrous hexane (20 ml) was added to precipitate the resulting pyridinium salts, and the resulting supernatant was filtered and transferred via a filter cannula to a second Schlenk flask containing a solution of the triazole, compound 1, (1 g, 3.27 mmol) in anhydrous $CH_2Cl_2$ (15 mL) precooled to −20° C. The reaction mixture was allowed to slowly warm to room temperature as it was stirred overnight. The reaction mixture was then quenched with saturated aqueous $K_2CO_3$, extracted with $CH_2Cl_2$, and the combined organic fractions were dried over anhydrous $MgSO_4$. Evaporation of the solvents affords a crude product that was purified by column chromatography on $SiO_2$ using 98:2 $CH_2Cl_2$:MeOH as the mobile phase to yield compound 2b as a colorless solid (0.67 g, 59%). m. p. 194-196° C.; $^1$H-NMR (CDCl$_3$, 25° C., 400 MHz): δ=8.81 (s, 1H, H$_{trz}$), 7.79-7.77 (m, 2H, H$_{ar}$), 7.62-7.58 (m, 4H, H$_{ar}$), 7.35 (d, 2H, H$_{ar}$, J=8 Hz), 5.24 (sept, 2H, J=6.4 Hz), 2.3 (sept, 2H, J=7.4 Hz), 1.67 (d, 6H, CH(CH$_3$)$_2$, J=6.4 Hz), 1.23 (d, 6H, CH(CH$_3$)$_2$, J=6.8 Hz), 1.13 (d, 6H, H(CH$_3$)z, J=7.2 Hz); $^{13}$C-NMR (CDCl$_3$, 25° C., 100 MHz): δ=145.5, 143.6, 133.1, 132.4, 131.5 (CH$_{trz}$), 130.3, 130.1, 124.9, 121.4, 56.6, 29.2, 24.8, 23.3, 22.8; HR-MS (ESI) m/z calcd. for $C_{23}H_{30}N_3^+$ [M+H]$^+$ 348.2434. found 348.2429.

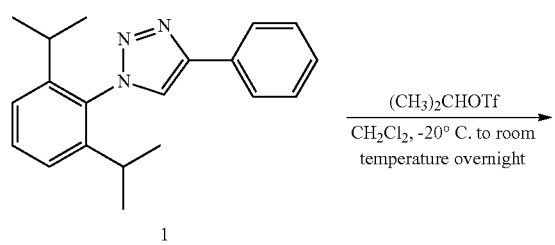

-continued

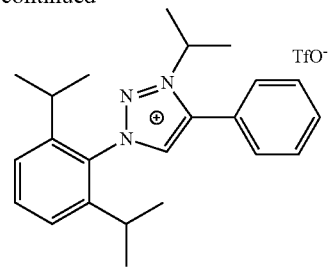

2a (59%)

Example 5

Synthesis of 1-(2,6-diisopropylphenyl)-3-methyl-4-phenyl-1H-1,2,3-triazol-5-ylidene

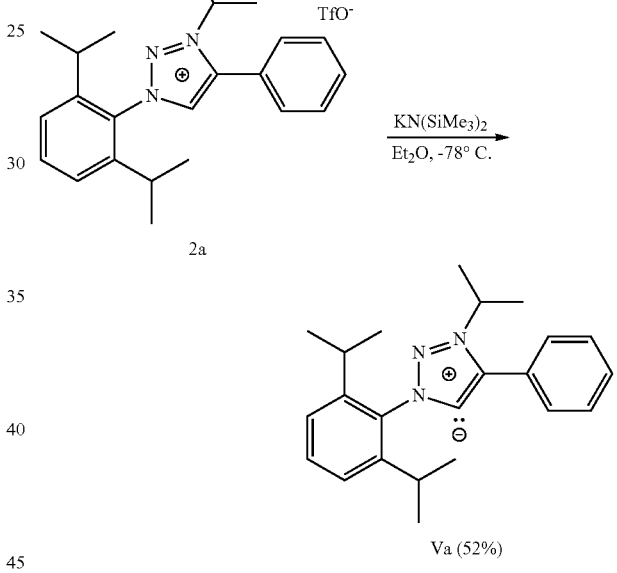

A Schlenk flask containing the triazolium salt, identified as compound 2a, (0.40 g, 0.9 mmol) and KN(SiMe$_3$)$_2$ (0.18 g, 0.9 mmol) was cooled to −78° C. and anhydrous Et$_2$O (7 mL) was added. The reaction mixture was stirred at −78° C. for 10 minutes, and allowed to warm up to room temperature for 50 minutes before the solvent was evaporated under reduced pressure. The residue was extracted twice by trituration in anhydrous hexane (2×5 mL). After filtration and transfer of the reaction mixture to a second Schlenk flask via a filter cannula, the solvent was evaporated to give the compound, identified as compound Va below, as a pale purlish-white solid (0.15 g, 52%). Crystals suitable for X-ray analysis were obtained by cooling a solution of compound Va in toluene/hexane (~9:1 v/v) to −30° C. m. p.: 50-52° C.; $^1$H NMR(C$_6$D$_6$, 25° C., 300 MHz): δ=7.9 (d, 2H, H$_{ar}$, J=7.1 Hz), 7.30 (d, 1H, J=7.1 Hz), 7.27 (m, 5H), 3.44 (s, 3H), 2.99 (sept, 2H, J=6.7 Hz), 1.31 (d, 6H, CH(CH$_3$)$_2$, J=6.7 Hz), 1.29 ppm (d, 6H, CH(CH$_3$)$_2$, J=6.8 Hz). $^{13}$C NMR (C$_6$D$_6$, 25° C., 75 MHz): δ=202.1, 148.8, 145.9, 139.8, 130.2, 129.8, 129.0, 128.6, 128.1, 124.1, 36.4, 29.2, 24.5.

Compound Va remained stable under limited oxygen and moisture conditions in the solid state for several days at −30° C. and for a few hours at room temperature. Upon heating in benzene solution for 12 hours at 50° C., compound Va decomposed to give, among other products, the triazole compound, identified as compound 3.

Example 6

Synthesis of 1-(2,6-Diisopropylphenyl)-3-(2-propyl)-4-phenyl-1H-1,2,3-triazol-5-ylidene To a Schlenk flask containing the triazolium salt, compound 2b, (0.20 g, 0.43 mmol) and KN(SiMe$_3$)$_2$ (0.085 g, 0.43 mmol) cooled to −78° C. was added anhydrous diethyl ether (7 mL). The reaction mixture was stirred at −78° C. for 10 minutes. Thereafter, the reaction mixture was allowed to warm up to room temperature for 50 minutes before the solvent was evaporated under reduced pressure. The residue was extracted twice by trituration in anhydrous hexane (2×5 mL). After filtration and transfer to a second Schlenk flask via a filter cannula, the solvent was evaporated to give the compound identified as Vb below as a pale pinkish-white solid (0.053 g, 37%). m. p.: 110-112° C.; $^1$H-NMR (C$_6$D$_6$, 25° C., 400 MHz): δ=7.50 (d, 2H, H$_{ar}$, J=6.8 Hz), 7.21 (m, 3H, H$_{ar}$, J=7.6 Hz), 7.12 (m, H$_{ar}$, 3H, J=8.0 Hz), 4.36 (sept, 2H, J=6.4 Hz), 2.7 (sept, 1H, CH(CH$_3$)$_2$, J=6.8 Hz), 1.25 (d, 6H, CH(CH$_3$)$_2$, J=6.4 Hz), 1.03 (d, 12H, CH(CH$_3$)$_2$, J=7.2 Hz); $^{13}$C-NMR (C$_6$D$_6$, 25° C., 100 MHz): δ=198.3, 148.3, 145.6, 139.9, 132.2, 130.5, 130.3, 129.5, 129.2, 128.6, 127.4, 124.3, 52.1, 29.2, 25.1, 24.1, 23.2.

Compound Vb showed no sign of decomposition after three days at room temperature in the solid state.

Example 7

Synthesis of the Iridium complex [(Va)Ir(CO)$_2$Cl]

A solution of the carbene, compound Va, (0.136 g, 0.43 mmol) in hexane (10 mL) was added at −78° C. to a stirred solution of [Ir(cod)Cl]$_2$ (0.144 g, 0.215 mmol) in THF (10 mL). The solution was allowed to warm to room temperature while stirring overnight. After evaporation of the solvent under reduced pressure, toluene (15 ml) was added, and carbon monoxide was bubbled through the solution for 30 minutes at room temperature. After solvent removal under reduced pressure, the crude green solid was purified by column chromatography on SiO$_2$ using hexane:ethyl acetate 80:20 (v/v) as the mobile phase to yield the compound, identified as [(Va)Ir(CO)$_2$Cl] below, as a yellow solid (0.189 mg, 73%). m. p.: 193-195° C.; $^1$H-NMR (CDCl$_3$, 25° C., 400 MHz): δ=7.82 (m, 2H, H$_{ar}$), 7.53 (m, 4H, 7.32 (d, J=8 Hz, 2H, H$_{ar}$), 4.13 (s, 3H), 2.54 (sept, J=6.8 Hz, 2H), 1.35 (d, 6H, CH(CH$_3$)$_2$, J=6.4 Hz), 1.09 (d, 6H, CH(CH$_3$)$_2$, J=6.8 Hz); $^{13}$C NMR (CDCl$_3$, 25° C., 100 MHz): δ=181.4, 168.7, 166.6, 148.0, 145.8, 130.9, 130.4, 128.8, 126.6, 124.0, 37.9, 29.2, 26.3, 22.5; IR (CH$_2$Cl$_2$): ν=2061, 1977 (ν(CO)) cm$^{-1}$; HR-MS (ESI) m/z calcd. for C$_{23}$H$_{25}$ClIrN$_3$O$_2$ [M+Na]$^+$ 626.1149. found 626.1163.

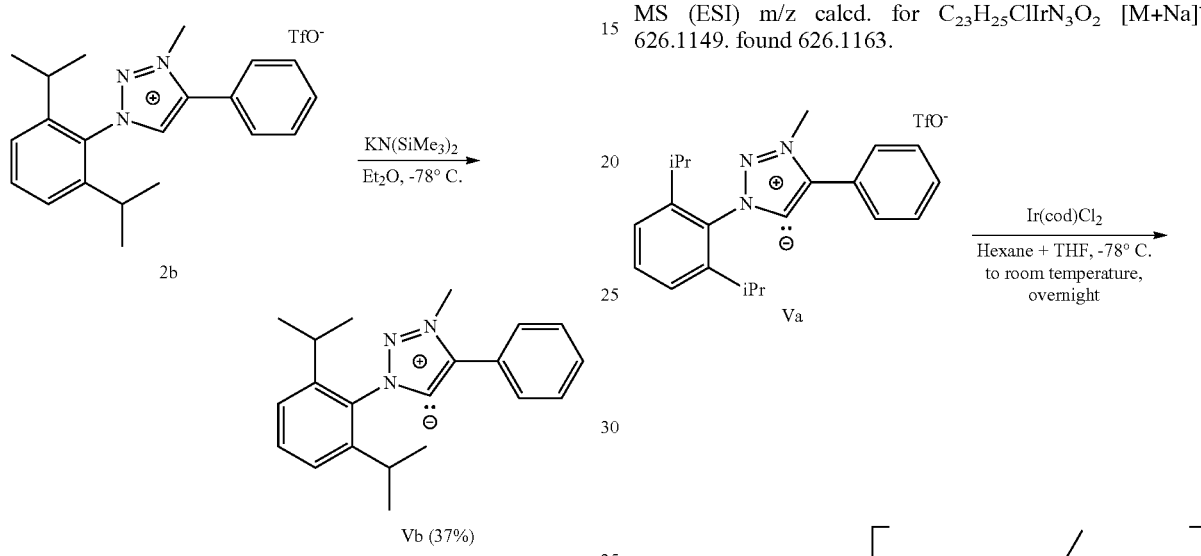

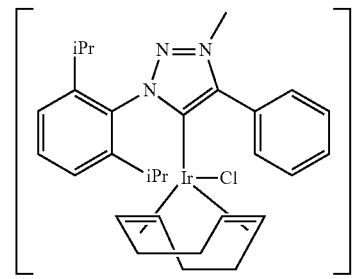

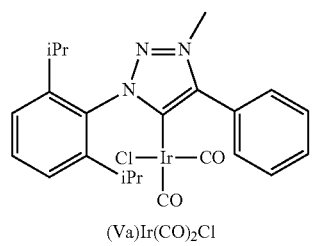

Example 8

Decomposition and Rearrangement of Triazolylidenes, Compounds Va and Vb

The composition of solutions of the triazolylidenes, identified as compounds Va and Vb, in $C_6D_6$ (~0.1 M) under an argon atmosphere in a septum-capped NMR tube were followed by $^1$H-NMR at time intervals as specified in Table 1 below.

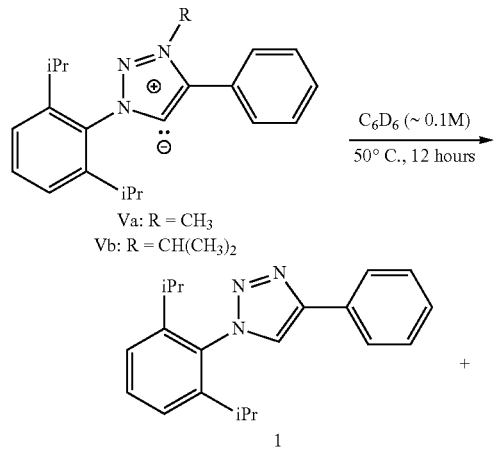

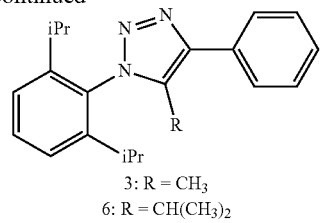

3: R = $CH_3$
6: R = $CH(CH_3)_2$

TABLE 1

| | Va | | Vb | |
|---|---|---|---|---|
| Reaction Time and Temperature | Estimated Relative Ratio of Compounds Va:1:3a | Reaction Time and Temperature | Estimated Relative Ratio of Compounds Vb:1:6 |
| 1 hour at room temperature | 1:0.15:0.1 | 1 hour at room temperature | 1:nd:nd |
| 7 days at room temperature | 1:1.5:0.9 | 2 days at room temperature | 1:0.09:nd |
| More than 12 hours at 50° C. | 1:4.3:2.6 | More than 12 hours at 50° C. | 1:0.06:nd |

In Table 1, the term "nd" refers to a compound that is not detected.

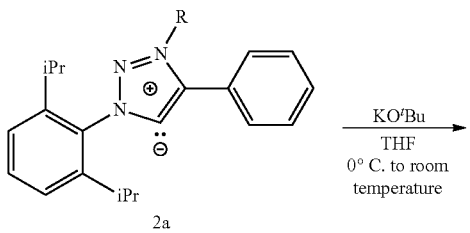

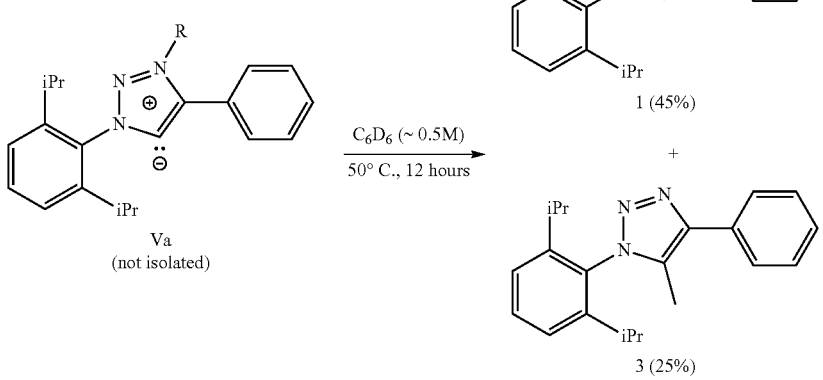

Decomposition and rearrangement of 1-(2,6-Diisopropylphenyl)-5-methyl-4-phenyl-1H-1,2,3-triazole To a flame-dried Schlenk flask equipped with a magnetic agitator and charged with the triazolium salt, identified as compound 2a, (235 mg, 0.5 mmol) and KO$^t$Bu (112 mg, 1.0 mmol) was added anhydrous THF (20 mL) under an argon atmosphere and at 0° C. The resulting mixture was stirred for 15 min at 0° C., during which a pale yellow-orange color develops. Then the mixture was stirred for an additional 45 min at room temperature before the solvents were evaporated under reduced pressure. The residue was extracted by trituration in anhydrous $C_6H_6$ (20 mL), filtered and transferred to a second Schlenk flask via a filter cannula. Solvents were evaporated under reduced pressure, and the residue was redissolved in anhydrous $C_6H_6$ (1.0 mL). The resulting purplish mixture was stirred at 50° C. for 12 h, quenched with EtOH (~1 mL), and the solvents were evacuated under reduced pressure. The crude product mixture was then purified by column chromatography on $SiO_2$ using dichloromethane as the mobile phase to afford, after evaporation of the solvents, compound 1 as an off-white solid (70 mg, 46%, higher Ri), followed by compound 4 as a viscous pale yellow oil (40 mg, 25%, lower Ri). $^1$H-NMR (CDCl$_3$, 300 MHz): δ=7.92 (m, 2H), 7.56-7.47 (m, 3H), 7.42-7.31 (m, 3H), 2.30 (s, 3H), 2.25 (sept, 2H, J=6.9 Hz), 1.16 (d, 6H, J=6.7 Hz), 1.15 (d, 6H, J=6.9 Hz); $^{13}$C-NMR (CDCl$_3$, 75 MHz): δ=146.8, 143.6, 131.9, 131.8, 131.1, 128.9, 127.8, 126.9, 126.8, 124.3, 28.6, 24.9, 23.4, 10.0; HR-MS (ESI): calcd. for $C_{21}H_{25}N_3$ [M+H]$^+$ 320.2121. found 320.2114.

As noted above, the publication, G. Guisado-Barrios, et al., "Crystalline 1H-1,2,3-Triazol-5-ylidenes: New Stable Mesoionic Carbenes (MICs)", Angew. Chem. Int. Ed., 2010, 49, 4759-4762, and all its supporting information, which is available online at http://dx.doi.org/10.1002/anie.201001864, is incorporated herein by reference in its entirety.

Example 9

Synthesis of Arylated MICs

Synthesis of Arylated MICs. Triazolium salts can be prepared by the methods described in the following: a) Wirschun, W., et al., J. Chem. Soc., Perkin Trans., 1, 1998, 1755-1761; b) Wirschun, W., et al., J. Prakt. Chem. 1998, 340, 300-308; c) Al-Masoudi, N., et al. J. Chem. Soc., Perkin Trans., 1, 1998, 947-953; d) Wirschun, W., et al. Synthesis 1997, 233-241; e) Wirschun, W.; et al., Tetrahedron, 1997, 53, 5755-5766; f) Weng, M., et al., J. Prakt. Chem. 2000, 342, 486-493; g) Hartman, W. W.; et al. Org. Synth., 1934, 14, 163.

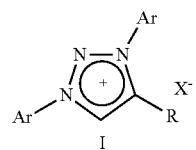

X = SbCl$_6$, PF$_6$

Triazenes 8a-d were first prepared by an adaptation of literature procedures, including the treatment of anilines with isoamyl nitrite (8a,d) (See Vernin, G., et al., J. Synthesis, 1977, 691-693; Nimitsiriwat, N., et al., Inorg. Chem., 2007, 46, 9988-9997; Barrett, A. G., et al., Inorg. Chem., 2008, 47, 7366-7376). Triazenes were also prepared by the nucleophilic attack of anilines on arenediazonium salts in pH-buffered aqueous solutions (8c) (see Hartman, W. W., et al., Org. Synth. 1934, 14, 163). Triazenes were also prepared by the nucleophilic attack of aryl Grignards on aryl azides (8b) (See Hauber, S.-O., et al., Angew. Chem. Int. Ed., 2005, 44, 5871-5875; Alexander, S. G., et al., Dalton Trans., 2009, 2326-2336). The cycloaddition is then best carried out in a convenient single one-pot operation by the addition of tert-butyl hypochlorite as the N-chlorinating agent to a stirred suspension of the triazene 8a-d, alkyne 9a-r, and potassium hexafluorophosphate in dichloromethane at −78° C., followed by warming to room temperature to afford the desired triazolium salts 10aa-da after filtration of the insoluble inorganic byproducts and trituration in diethyl ether (Scheme 2). It is noteworthy that heterocycle formation, unlike for CuAAC, proceeds rapidly below room temperature, and does not necessitate copper catalysts. The reaction works well with a variety of alkynes and tolerates both electron-rich (9j,l) and electron-poor (90 alkynes, in addition to enynes (9k). Highly sterically demanding MIC precursors can be prepared in good yields (10ac, 10ad). In addition to terminal alkynes, cycloaddition with internal alkynes also proceeds well (10an-ao). Trimethylsilyl alkynes react as well, but under these conditions protodesilylation occurs readily and the protic triazolium salts are instead obtained (10aa, 10ae, 10ai). The success in the formation of the heterocycle depends on the stability of the postulated intermediates G, H, and, for some combinations of triazene and alkyne substrates, decomposition of the intermediates is competitive with the rate of cycloaddition. It was found that that the reaction proceeds best at high concentrations in the presence of an excess of alkyne. Occasionally, as is the case for dimesityltriazene 8b, performing the cycloaddition in the absence of potassium hexafluorophosphate, which presumably shifts the G-H equilibrium towards the more stable chlorotriazene, and performing the anion exchange in a subsequent step results in higher yields. This reaction is readily scaled-up, as exemplified by the preparation of 10bb at the 20-mmol scale in excellent yields (10.1 g, 88%).

Scheme 1. Triazolium salts from the formal cycloaddition of 1,3-diaza-2-azoniaallene salts and alkynes.

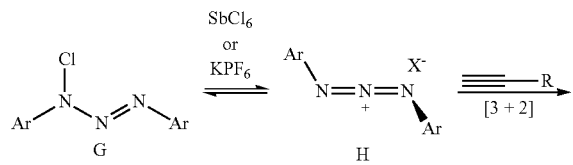

Scheme 2. Preparation of 1,3-diaryl-1,2,3-triazolium salts from triazenes and alkynes.

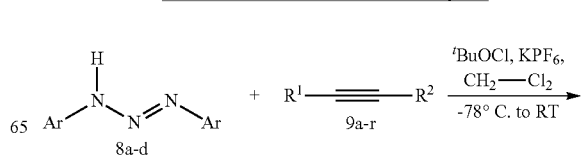

37
-continued

10aa-dda

1,3-Diaryl triazolium with R¹, R² substituents, PF₆⁻ counterion (general structure)

10ab — 1,3-Dipp, 4-Ph triazolium PF₆⁻ (94–95%)[a]

10ac — 1,3-Dipp, 4-Mes triazolium PF₆⁻ (57%)

10ad — 1,3-Dipp, 4-Dipp triazolium PF₆⁻ (66%)

10ae — 1,3-Dipp, 4-Tipp triazolium PF₆⁻ (50%)

10af — 1,3-Dipp, 4-H triazolium PF₆⁻ (70%)[b]

10ag — 1,3-Dipp, 4-COOMe triazolium PF₆⁻ (65%)

10ah — 1,3-Dipp, 4-tBu triazolium PF₆⁻ (22%)

10ai — 1,3-Dipp, 4-Cy triazolium PF₆⁻ (65%)

38
-continued

10aj — 1,3-Dipp, 4-Me triazolium PF₆⁻ (62%)[c]

10ak — 1,3-Dipp, 4-OEt triazolium PF₆⁻ (59%)

10al — 1,3-Dipp, 4-(cyclohex-1-en-1-yl) triazolium PF₆⁻ (61%)

10am — 1,3-Dipp, 4-(2,6-dimethoxycyclohex-1-en-1-yl) triazolium PF₆⁻ (78%)

10an — 1,3-Dipp, 4-(1-hydroxycyclohexyl) triazolium PF₆⁻ (66%)

10ao — 1,3-Dipp, 4,5-diPh triazolium PF₆⁻ (88%)

10ap — 1,3-Dipp, 4-Ph, 5-Me triazolium PF₆⁻ (70%)

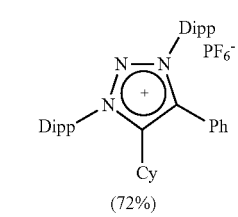

(72%) 10ap

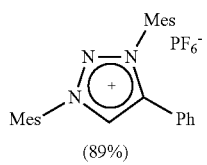

(89%) 10ba

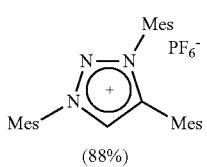

(88%) 10bb

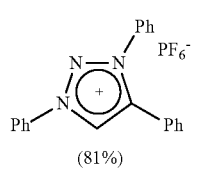

(81%) 10ca

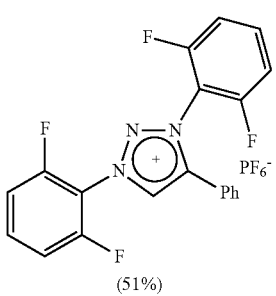

(51%) 10da a) Preformed with either PhCCH (9a) or PhCCSiMe₃ (9r);
b) With Me₃SiCCH (9e);
c) With CH₃CCSiMe₃.

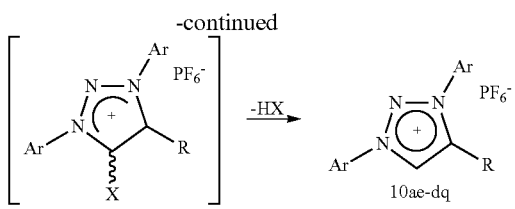

10ae

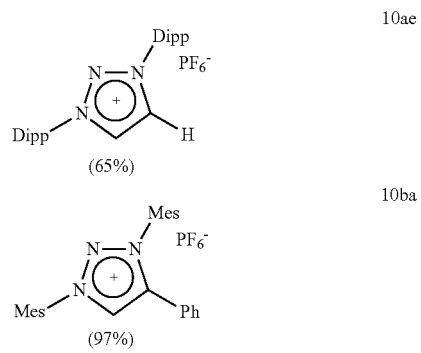

(65%) 10ba (97%) 10be (91%) 10ce (52%)

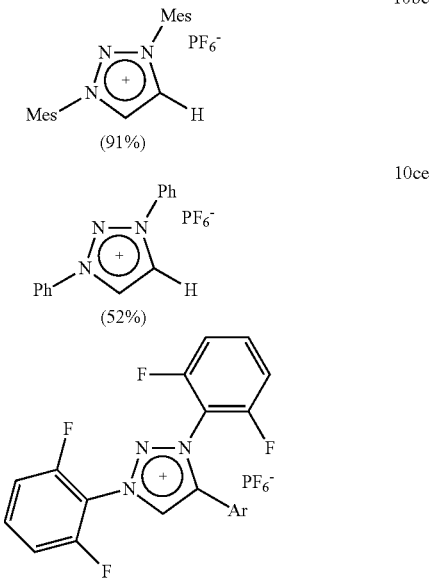

10da (>99%), Ar = Ph)
10dq (88%, Ar = 2,6-C₆H₃F₂)

Vinyl halides (11a-q) can be used as synthetic alkyne equivalents in a cognate preparation of MIC precursors (Scheme 3a). The cycloaddition proceeds under the aforementioned conditions, during which spontaneous elimination of hydrogen halide occurs. Allyl halides (e.g. 12) can also be used; in this case dehydrohalogenation-aromatization of the intermediate adduct (13) is not truly spontaneous, but is readily achieved by treatment with an amine base in a second step (Scheme 3b).

Scheme 3. Preparation of 1,3-diaryl-1,2,3-triazolium salts from triazenes and synthetic alkyne equivalents.

A)

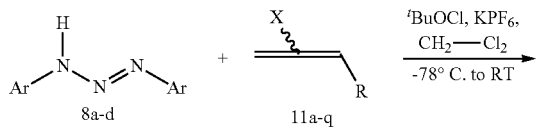

B)

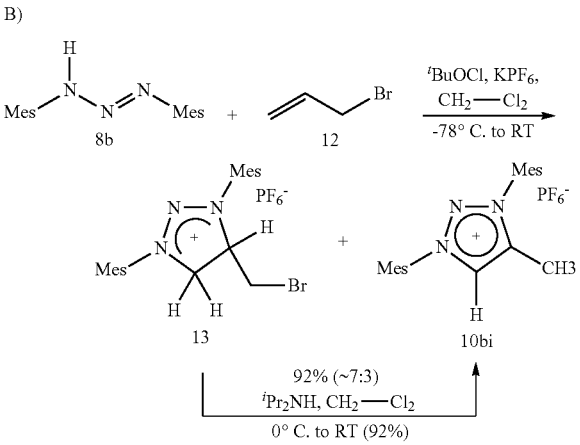

Treatment of 1,3-diaryl-1H-1,2,3-triazoliums salts 10aa-xx with potassium bases such as potassium bis(trimethylsilyl)amide or preferably potassium tert-butoxide results in their clean deprotonation and formation of the target stable free MICs 14aa-xx in moderate to excellent yields (Scheme 4). Treatment of triazolium salt 10 am with potassium tert-butoxide does not give rise to the expected MIC, but to MIC 14ae, which was independently obtained by deprotonation of precursor 10ae (Scheme 5). These results are rationalized by the consecutive deprotonation of the hydroxyl substituent and extrusion of cyclohexanone. This observation is significant for it establishes the viability of one of the elementary steps required for numerous carbene-mediated organocatalytic reactions (e.g. benzoin condensation, Stetter reaction). MIC 14ae is also remarkable in that it is the first stable free carbene that can tolerate the sterically unhindered proton as a substituent in alpha to the carbene center. While such is likely possible for aNHC B and other types of mesoionic carbenes, it is not accessible for NHCs A as an internal N to C proton transfer would instantly anihilate the carbene.

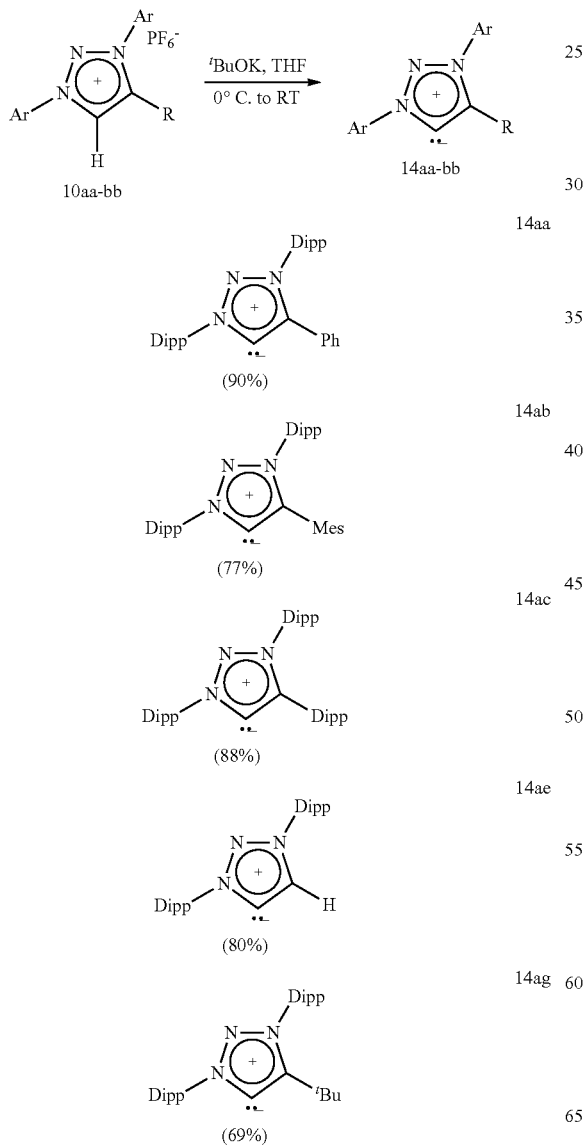

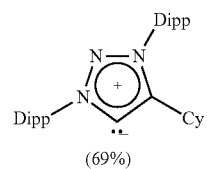

14ah (69%)

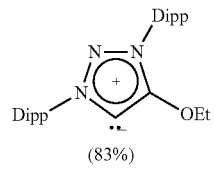

14aj (83%)

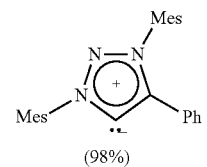

14ba (98%)

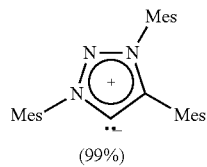

14bb (99%)

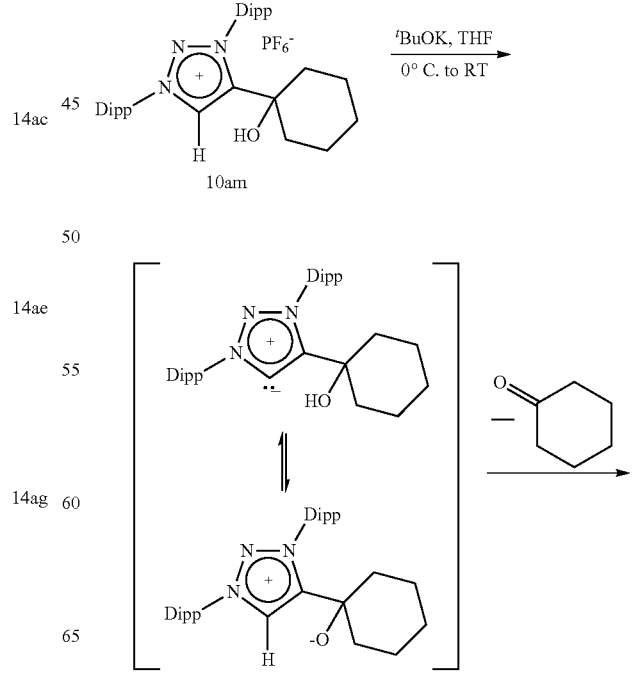

Scheme 5. Preparation of MICs 14ae by ketone extursion from triazolium precursors 10am.

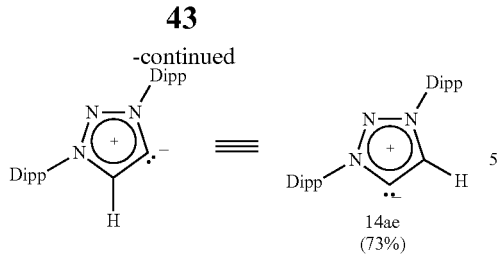

14ae (73%)

Figure 6:
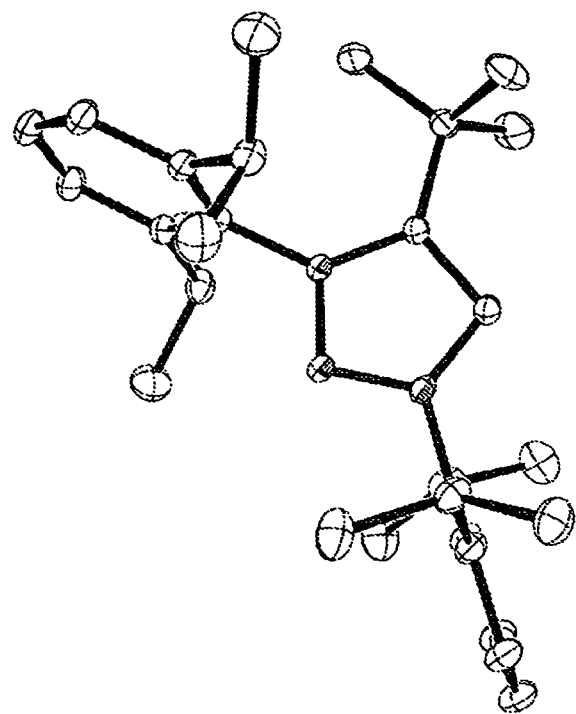
FIG. 6 shows the structure of MIC 14ag as established by X-ray crystallography. Solid-state structures of 10ac (left) and 14ag (right) with 50% thermal ellepsoids. For clarity, counter-ions and hydrogen atoms, except for the ring hydrogen of 10ac were omitted. Selected bond lengths (Å) and angles (°) for 10ac: N1-N2: 1.3201(16), N2-N3: 1.3278(16), N3-C4: 1.3819(16), C4-C5: 1.3713(19), C5-N1: 1.3523(17), ∠N1-C5-C4: 106.36(12). 14ag: N1-N2: 1.3420(7), N2-N3: 1.3302(7), N3-C4: 1.3763(8), C4-C5: 1.4041(8), C5-N1: 1.3655(8), ∠N1-C5-C4: 100.21(5).
Figure 6:
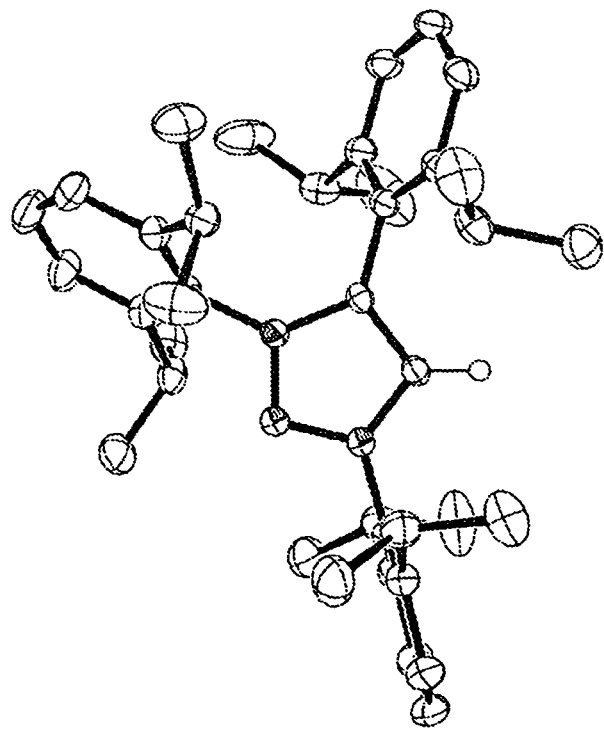

Experimental Properties of MICs. The structure of MIC 14ag was established by X-ray crystallography (FIG. 6).

The free carbenes proved to be very robust and could be stored in the solid state at room temperature under an inert atmosphere for several weeks. Upon heating in benzene solution for 12 hour at 50° C., MIC 14ba (m.p.=154-156° C. dec.) shows no sign of decomposition, which illustrates the efficacy of introducing of aryl substituents at the third nitrogen position in the ring to shut down undesired decomposition pathways. Consistent with previous results, no dimerization of these carbenes was observed in solution.

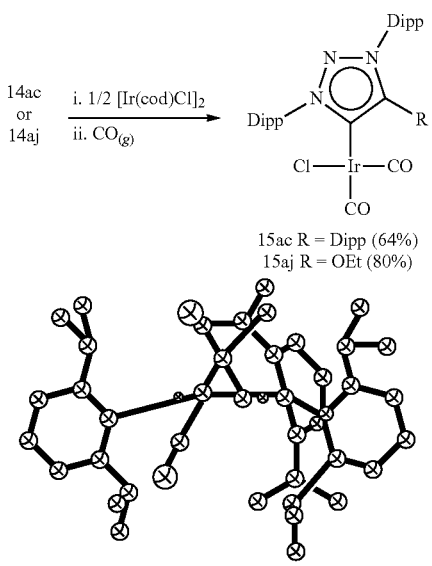

Scheme 6. Preparation of iridium carbonyl complexes.

15ac R = Dipp (64%)
15aj R = OEt (80%)

With respect to Scheme 6, the right side shows a molecular view of 15ac in the solid state with 50% thermal ellipsoids. For clarity, hydrogen atoms are omitted from the right side of Scheme 6.

A wide variety of 1,3-diaryl substituted MICs are conveniently prepared through the scalable Wirschun-Jochims formal cycloaddition between 1,3-diaza-2-azoniaallene salts and alkynes or synthetic alkyne equivalents, followed by deprotation with mild alkoxide bases. By this method, MICs bearing both highly sterically demanding (Tipp, tBu), or minimally sterically demanding (H), as well as polar and functionalized substituents in alpha to the carbene center can be obtained. The widespread availability of chiral acetylenes derived from the diastereo- or enantioselective addition of acetylides to carbonyls and imines suggests that this synthetic route will be amenable to the facile synthesis of chiral variants of these strongly electron-donating ligands. The combination of their practical, versatile and modular preparation, enhanced stability, advantageous electronic properties, and the demonstration of their effectiveness in a catalytic setting foreshadows the development of numerous MIC transition metal complexes for catalytic applications.

Example 10

1,4-Bis(2,4,6-trimethylphenyl)-3-isopropyl-1H-1,2,3-triazolium trifluoromethanesulfonate (1d). To a stirred solution of 2-propanol (690 µL, 9.0 mmol) and pyridine (750 µL, 9.3 mmol) in dichloromethane (5 mL) at −78° C. is added trifluoromethanesulfonic anhydride (1.5 mL, 8.9 mmol). The resulting mixture is stirred at −78° C. for 30 min, and then stirred an additional 30 min as is allowed to slowly reach room temperature. Pentane (10 mL) is added to precipitate the pyridinium salt byproduct, and contents are transferred via filter cannula into a solution of 1,4-bis(2,4,6-trimethylphenyl)-1H-1,2,3-triazole (915 mg, 3 mmol) in dichloromethane (5 mL) at 78° C. The resulting mixture is stirred at −78° C. for 30 min, and then stirred an additional 30 min as is allowed to slowly reach room temperature. Solvents are then evaporated under reduced pressured until a total volume of ca. 5 mL is reached, and additional dichloromethane (5 mL) is added. The mixture is stirred at room temperature overnight, followed by an additional 3 hour at 50° C. Evaporation of the volatiles under reduced pressure affords a crude product that is purified by column chromatography on $SiO_2$ using 98:2 to 90:10 dichloromethane:methanol (v/v) as the mobile phase, and then by reprecipitation from dichloromethane into an excess of diethyl ether to afford triazolium salt 1d as a white solid (902 mg, 60%). $^1$H-NMR ($CD_3CN$, 300 MHz): δ=8.65 (s, 1H), 7.23 (s, 2H), 7.20 (s, 2H), 4.67 (sept, J=6.8 Hz, 1H), 2.41 (s, 3H), 2.40 (s, 3H), 2.14 (s, 6H), 2.13 (s, 6H), 1.61 (d, J=6.8 Hz, 6H). $^{13}$C-NMR ($CDCl_3$, 75 MHz): δ=144.1, 143.7, 142.2, 139.5, 135.6, 133.2, 132.7, 131.6, 130.9, 130.2, 57.5, 22.7, 21.5, 21.4, 20.5, 17.5. HR-MS (ESI): Calcd. for $C_{23}H_{30}N_3$ [M+]: 348.2434. found 348.2436. M.p.: 180-181° C.

Example 11

1,3-Dimesityltriazene (8b). A THF solution of MesMgBr.LiCl is first prepared by an adaptation the procedure of Knochel et al. To a stirred suspension of magnesium turnings (0.72 g, 30 mmol) and anhydrous LiCl (1.26 g, 30 mmol) in anhydrous THF (40 mL) is added 2-bromomesitylene (5.05 mL, 33 mmol). The exothermic reaction initiates slowly and is allowed to stir overnight at room temperature. To the resulting mixture, which is cooled to 0° C., is added 2-azidomesitylene (4.59 g, 28.5 mmol). Stirring is continued for 1 hour at 0° C., and then an additional 1 hour while allowing to warm to room temperature. The reaction mixture is quenched by pouring the contents into water. A minimum of aqueous $NH_4Cl$ is added to neutralize the pH, and the organic products are extracted with $Et_2O$. After washing the combined organic layers with brine, solvents are evaporated at room temperature under reduced pressure to afford a crude product that is recrystallized from $Et_2O$-MeOH to afford 8b (7.41 g, 92%) as off-white needles over 2 crops. $^1$H-NMR ($CDCl_3$, 300 MHz):

δ=9.14 (br s, 1H), 6.93 (br s, 4H), 2.32-2.30 (br m, 18H). M.p.: 92-94° C. (dec). Characterization data for 8b are consistent with literature values.

Example 12

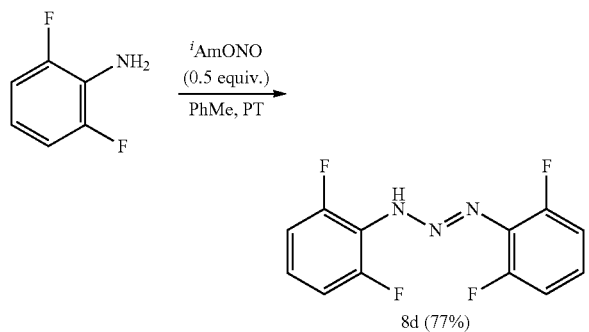

8d (77%)

1,3-Bis(2,6-difluorophenyl)triazene (8d). To a stirred solution of 2,6-difluoroaniline (3.87 g, 30 mmol) in PhMe (20 mL) at room temperature is added isoamyl nitrite (1.76 g, 15 mmol). Stirring is continued until the mixture is homogenous (~1-2 min), and the mixture is let to settle without stirring at room temperature overnight, during which product 8d crystallizes from solution. The solid is collected by filtration, washed with cold PhMe and pentane, and dried under vacuum to afford 8d (3.12 g, 77%) as yellow blocks. Triazene 8d should quickly be stored in a freezer (30° C.) as it thermally decomposes at room temperature. $^1$H-NMR (CDCl$_3$, 300 MHz): δ=9.70 (br s, 1H), 7.16-7.07 (m, 2H), 7.02-6.93 (m, 4H). $^{13}$C-NMR (CDCl$_3$, 75 MHz): δ=155.2 (d, J=250 Hz), 126.2 (br), 112.3 (dd, J=17, 6 Hz). 19F-NMR (CDC$_{13}$, 282 MHz): δ=−121.9 (br). M.p.: 94-95° C. (dec.). HR-MS (ESI): Calcd. for C$_{12}$H$_7$F$_4$N$_3$ [M+H]: 270.0649. found 270.0648.

Example 13

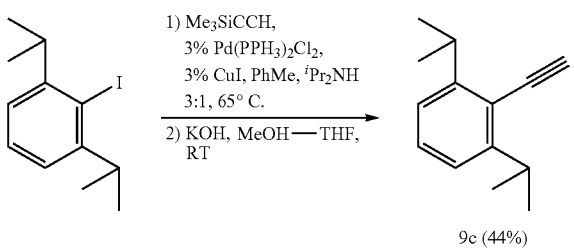

9c (44%)

2,6-Diisopropylphenylacetylene (9c). To a stirred, degassed solution of 2-iodo-1,3-diisopropylbenzene (5.76 g, 20 mmol), trans-dichlorobis(triphenylphosphine)palladium (II) (421 mg, 0.6 mmol), copper(I) iodide (115 mg, 0.6 mmol) in 3:1 (v/v) toluene:diisopropylamine (100 mL) under argon is added trimethylsilylacetylene (4.25 mL, 30 mmol). The resulting mixture is stirred under argon at room temperature for 1 hour, followed by 12 hour at 65° C., during which period a heavy precipitate attributed to iPr$_2$NH.HI is formed. Contents are passed on a SiO$_2$ plug with ethyl acetate as eluent. Volatiles are evaporated under reduced pressure, and the contents are passed on a short SiO$_2$ column with pentane as the eluent to afford the crude TMS-protected alkyne as a pale yellow oil that is directly carried to the next step without further purification. The oil is dissolved in THF (100 mL) and the solution is degassed by bubbling argon gas through for approximately 30 min. To the stirred mixture is added by a solution of potassium hydroxide (2 g) in methanol (10 mL). The reaction mixture is stirred at room temperature for 1 hour, before pouring of the contents in saturated aqueous NaCl. After extration with diethyl ether and evaporation of the volatiles, the crude alkyne is purified by chromatography on SiO$_2$ using pentane as the mobile phase to afford alkyne 9c as a colorless oil (1.67 g, 44% over 2 steps). $^1$H-NMR (CDCl$_3$, 300 MHz): δ=7.30 (t, J=7.7 Hz, 1H), 7.14 (d, J=7.7 Hz, 2H), 3.58 (sept, J=6.9 Hz, 2H), 3.48 (s, 1H), 1.27 (d, J=6.9 Hz, 12H). $^{13}$C-NMR (CDCl$_3$, 75 MHz): δ=151.7, 129.0, 122.3, 120.0, 85.3, 80.7, 31.8, 23.5. Characterization data for 9c are consistent with literature values. (Gagnon, E.; Halperin, S. D.; Métivaud, V.; Maly, K. E.; Wuest, J. D. J. Org. Chem. 2010, 75, 399-406).

Example 14

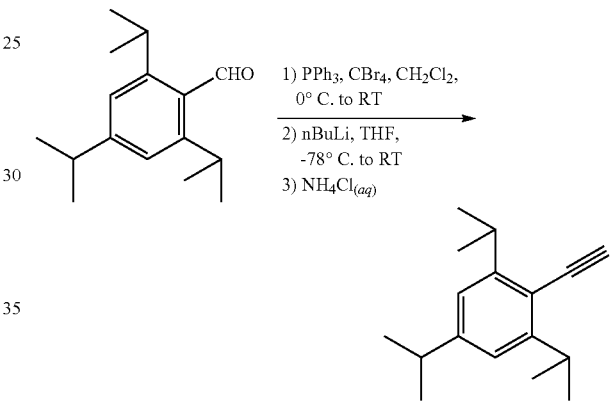

9d (58%)

2,4,6-Triisopropylphenylacetylene (9d). To a stirred, degassed solution of triphenylphosphine (21 g, 80 mmol) and carbon tetrabromide (13.3 g, 40 mmol) in dry dichloromethane at 0° C. was added 2,4,6-triisopropylbenzaldehyde (4.64 g, 20 mmol). The resulting mixture was stirred overnight as it was allowed to slowly warm to room temperature. Solids were filtered off, and the volatiles were evacuated under reduced pressure. Pentane was then added, and after extensive trituration the mixture was filtered on a SiO$_2$ plug with pentane as the eluent to afford after evaporation of the solvents the crude intermediate dibromoalkene as a colorless oil that is directly taken to the next step without surther purification. The intermediate is dissolved in dry THF (50 mL), and to the stirred solution cooled to −78° C. is then added nBuLi (2.5M in hexanes, 10 mL) dropwise. The mixture is stirred for 1 hour at −78° C., and let to warm to room temperature for an additional hour. The reaction is quenched by the addition of saturated aqueous NH$_4$Cl, extracted with pentane, and the organic fractions are dried over anhydrous MgSO$_4$. After filtration and evaporation of the solvents, the crude alkyne is purified by filtration on a SiO$_2$ plug with pentane as the eluent. A small crystal of hydroquinone is added to stabilize the product, and the volatiles are evaporated under reduced pressure to afford 9d as a pale pinkish oil (2.63 g, 58% over 2 steps). $^1$H-NMR (CDCl$_3$, 300 MHz): δ=7.00 (s, 2H), 3.56 (sept, J=6.9 Hz), 3.43 (s, 1H), 2.91 (sept, J=6.9 Hz), 1.28 (d, J=6.9 Hz, 12H), 1.27 (d, J=6.9 Hz, 6H). $^{13}$C-NMR (CDCl$_3$, 75 MHz): δ=151.6, 149.7, 122.3, 120.5, 84.5, 81.0, 34.7, 31.8, 24.1, 23.5. Characterization data for 9d are consistent with literature values. (See Knorr, R.; Ruhdorfer, J.; Böhrer, P.; Bronberger, H.; Räpple, E. Liebigs Ann. Chem. 1994, 433-438).

Example 15

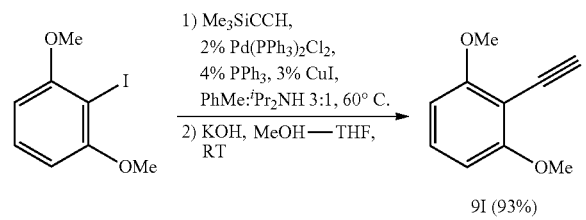

2,6-Dimethoxyphenylacetylene (9l). To a stirred, degassed solution of 2-iodo-1,3-dimethoxybenzene (13.2 g, 50 mmol), trans-dichlorobis(triphenylphosphine)palladium(II) (702 mg, 1 mmol), triphenylphospine (524 mg, 2 mmol), and copper(I) iodide (288 mg, 1.5 mmol) in 3:1 (v/v) toluene:diisopropylamine (200 mL) under argon is added trimethylsilylacetylene (8.0 mL, 57 mmol). The resulting mixture is stirred under argon at room temperature for 1 h, followed by 48 hour at 60° C., during which period a heavy precipitate attributed to iPr$_2$NH.HI is formed. Contents are passed on a SiO$_2$ plug with ethyl acetate as eluent. Volatiles are evaporated under reduced pressure, and the contents are passed on a short SiO$_2$ column with 95:5 to 90:10 pentane:ethyl acetate (v/v) as the eluent to afford the crude TMS-protected alkyne as an off-white solid that is directly carried to the next step without further purification. The solid is dissolved in THF (90 mL) and the solution is degassed by bubbling argon gas through for ca. 30 min. To the stirred mixture is added by a solution of sodium hydroxide (6 g) in methanol (30 mL). The reaction mixture is stirred at room temperature for 1 h, before pouring of the contents in saturated aqueous NaCl. After extration with diethyl ether and evaporation of the volatiles, the crude alkyne is purified by passage through a short SiO$_2$ column using 1:1 dichloromethane:pentane (v/v) as the eluent to afford alkyne 9l as a beige solid (7.55 g, 93% over 2 steps). $^1$H-NMR (CDCl$_3$, 300 MHz): δ=7.25 (t, J=8.4 Hz, 1H), 6.54 (d, J=8.4 Hz, 2H), 3.89 (s, 6H), 3.57 (s, 1H). $^{13}$C-NMR (CDCl$_3$, 75 MHz): δ=161.9, 130.2, 103.2, 99.9, 85.3, 76.3, 55.9. Characterization data for 9l are consistent with literature values (See Wayland, B. B.; Sherry, A. E.; Poszmic, G.; Bunn, A. G. J. Am. Chem. Soc. 1992, 114, 1673-1681).

Example 16

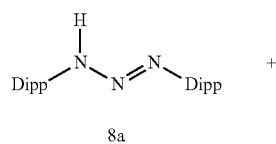

8a

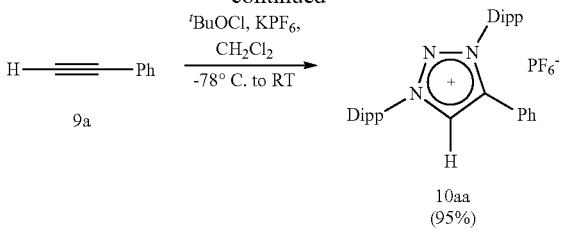

1,3-Bis(2,6-diisopropylphenyl)-4-phenyl-1H-1,2,3-triazolium hexafluorophosphate (10aa). To a stirred suspension of triazene 8a (1098 mg, 3 mmol) and anhydrous potassium hexafluorophosphate (750 mg, 4 mmol) in dry dichloromethane (20 mL) in the dark at −78° C. is added tert-butyl hypochlorite (500 μL, 4.4 mmol), upon which the mixture instantly darkens. Stirring is pursued at −78° C. for 30 min, and phenylacetylene 9a (500 μL, 4.6 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10aa as an off-white solid (1.74 g, 95%). Analytical samples were obtained after recrystallization by vapor diffusion of diethyl ether in an acetonitrile solution of 10aa. $^1$H-NMR (CD$_3$CN, 300 MHz): δ=9.17 (s, 1H), 7.77 (td, J=8.2, 1.4 Hz, 2H), 7.61-7.48 (m, 7H), 7.44-7.41 (m, 2H), 2.46 (sept, J=6.9 Hz, 2H), 2.38 (sept, J=6.9 Hz, 2H), 1.32 (d, J=6.9 Hz, 6H), 1.18 (d, J=6.9 Hz, 6H), 1.12 (d, J=6.9 Hz, 6H), 1.01 (d, J=6.9 Hz, 6H). $^{13}$C-NMR (CD$_3$CN, 75 MHz): δ=146.5, 134.7, 134.5, 133.6, 132.8, 131.5, 130.6, 130.2, 129.8, 126.8, 126.2, 122.8, 30.2, 30.0, 25.5, 25.0, 24.0, 22.7. $^{19}$F-NMR (CD$_3$CN, 282 MHz) δ=71.8 (d, J=705 Hz). $^{31}$P-NMR (CD$_3$CN, 121 MHz): −144.4 (sept, J=705 Hz). M.p.: >250° C. HR-MS (ESI): Calcd. for C$_{32}$H$_{40}$N$_3$ [M+]: 466.3217. found 466.3240.

Example 17

1,3-Bis(2,6-diisopropylphenyl)-4-phenyl-1H-1,2,3-triazolium hexafluorophosphate (10aa), alternate preparation. Proceeding as above with trimethylsilyl phenylacetylene 9r (900 μL, 4.6 mmol) in place of 9a to afford triazolium salt 10aa (1.73 g, 94%). Characterization data are identical as for 10aa prepared by the first method.

Example 18

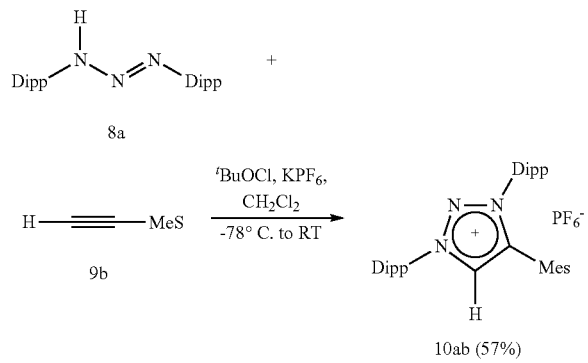

1,3-Bis(2,6-diisopropylphenyl)-4-(2,4,6-trimethylphenyl)-1H-1,2,3-triazolium hexafluorophosphate (10ab). To a stirred suspension of triazene 8a (1098 mg, 3 mmol) and anhydrous potassium hexafluorophosphate (750 mg, 4 mmol) in dry dichloromethane (20 mL) in the dark at −78° C. is added tert-butyl hypochlorite (500 μL, 4.4 mmol), upon which the mixture instantly darkens. Stirring is pursued at −78° C. for 30 min, and mesitylacetylene 9b (650 μL, ~4.6 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ab as an off-white solid (1.11 g, 57%). Analytical samples were obtained after recrystallization by vapor diffusion of diethyl ether in an acetonitrile solution of 10ab. $^1$H-NMR (CD$_3$CN, 300 MHz): δ=9.11 (s, 1H), 7.79 (t, J=7.8 Hz, 1H), 7.68 (t, J=7.8 Hz, 1H), 7.58 (d, J=7.8 Hz, 2H), 7.45 (d, J=7.8 Hz, 2H), 7.06 (s, 2H), 2.34 (sept, J=6.8 Hz, 2H), 2.31 (sept, J=6.8 Hz, 2H), 2.27 (s, 3H), 2.15 (s, 6H), 1.32 (d, J=6.8 Hz, 6H), 1.22 (d, J=6.8 Hz, 6H), 1.10 (d, J=6.8 Hz, 6H), 1.02 (d, J=6.8 Hz, 6H). $^{13}$C-NMR (CD$_3$CN, 75 MHz): δ=146.5, 146.3, 145.8, 144.0, 139.6, 135.9, 134.63, 134.57, 131.3, 130.8, 130.6, 126.6, 126.2, 30.8, 30.4, 26.6, 24.4, 24.2, 21.7, 21.4, 21.3. M.p.: >250° C. HR-MS (ESI): Calcd. for C$_{35}$H$_{46}$N$_3$ [M+]: 508.3686. found 508.3687.

Example 19

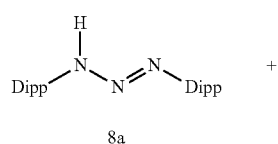

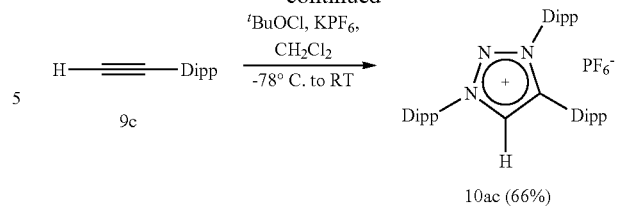

1,3,4-Tris(2,6-diisopropylphenyl)-1H-1,2,3-triazolium hexafluorophosphate (10ac). To a stirred suspension of triazene 8a (1098 mg, 3 mmol) and anhydrous potassium hexafluorophosphate (750 mg, 4 mmol) in dry dichloromethane (20 mL) in the dark at −78° C. is added tert-butyl hypochlorite (500 μL, 4.4 mmol), upon which the mixture instantly darkens. Stirring is pursued at −78° C. for 30 min, and (2,6-diisopropylphenyl)acetylene 9c (930 μl, ~4.6 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ac as an off-white solid (1.38 g, 66%). Analytical samples were obtained after recrystallization by vapor diffusion of diethyl ether in an acetonitrile solution of 10ac. $^1$H-NMR (CD$_3$CN, 300 MHz): δ=9.04 (s, 1H), 7.79 (t, J=7.9 Hz, 1H), 7.67 (t, J=7.9 Hz, 1H), 7.65-7.54 (m, 3H), 7.48 (d, J=7.9 Hz, 2H), 7.41 (d, J=7.9 Hz, 2H), 2.43 (sept, J=6.8 Hz, 2H), 2.33 (sept, J=6.8 Hz, 2H), 2.21 (sept, J=6.8 Hz, 2H), 1.32 (d, J=6.8 Hz, 6H), 1.28 (d, J=6.8 Hz, 6H), 1.17 (d, J=6.8 Hz, 6H), 1.11 (d, J=6.8 Hz, 6H), 0.98 (d, J=6.8 Hz, 6H), 0.93 (d, J=6.8 Hz, 6H). $^{13}$C-NMR (CD$_3$CN, 75 MHz): δ=150.0, 146.4, 146.0, 136.1, 134.6, 134.5, 134.2, 127.0, 126.2, 126.0, 32.8, 31.0, 30.6, 26.5, 24.1, 22.6, 21.9. HR-MS (ESI): Calcd. for C$_{38}$H$_{52}$N$_3$ [M+]: 550.4156. found 550.4159.

Example 20

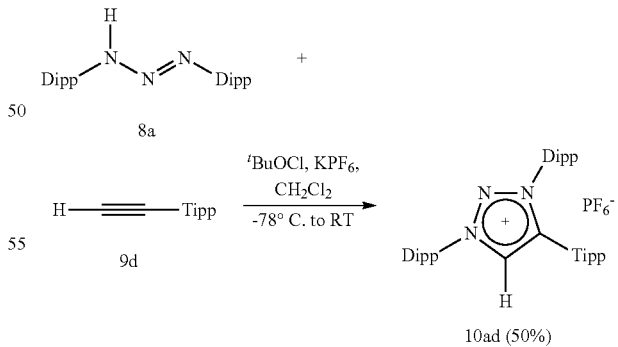

1,3-Bis(2,6-diisopropylphenyl)-4-(2,4,6-triisopropylphenyl)-1H-1,2,3-triazolium hexafluorophosphate (10ad). To a stirred suspension of triazene 8a (1098 mg, 3 mmol) and anhydrous potassium hexafluorophosphate (750 mg, 4 mmol) in dry dichloromethane (20 mL) at −78° C. is added tert-butyl hypochlorite (350 μL, 3.1 mmol), upon which the mixture instantly darkens. Stirring is pursued at −78° C. for 30 min, and (2,4,6-triisopropylphenyl)acetylene 9d (500 μL, ~2.2 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ad as an off-white solid (0.85 g, 50%). Analytical samples were obtained after recrystallization by vapor diffusion of diethyl ether in an acetonitrile solution of 10ad. $^1$H-NMR (CD$_3$CN, 300 MHz): δ=9.02 (s, 1H), 7.79 (t, J=7.9 Hz, 1H), 7.67 (t, J=7.9 Hz, 1H), 7.58 (d, J=7.9 Hz, 2H), 7.48 (d, J=7.9 Hz, 2H), 7.28 (s, 2H), 2.96 (sept, J=6.8 Hz, 1H), 2.41 (sept, J=6.8 Hz, 2H), 2.29 (sept, J=6.8 Hz, 2H), 2.18 (sept, J=6.8 Hz, 2H), 1.33 (d, J=6.8 Hz, 6H), 1.28 (d, J=6.8 Hz, 6H), 1.22 (d, J=6.8 Hz, 6H), 1.17 (d, J=6.8 Hz, 6H), 1.11 (d, J=6.8 Hz, 6H), 0.96 (d, J=6.8 Hz, 6H), 0.93 (d, J=6.8 Hz, 6H). $^{13}$C-NMR (CD$_3$CN, 75 MHz): δ=155.5, 150.0, 146.4, 146.1, 144.6, 136.0, 134.6, 134.4, 131.2, 130.8, 127.1, 126.2, 124.2, 116.3, 35.3, 32.9, 31.0, 30.6, 26.54, 26.49, 24.21, 24.15, 23.9, 22.6, 21.9. HR-MS (ESI): Calcd. for C$_{41}$H$_{58}$N$_3$ [M+]: 592.4625. found 592.4626.

Example 21

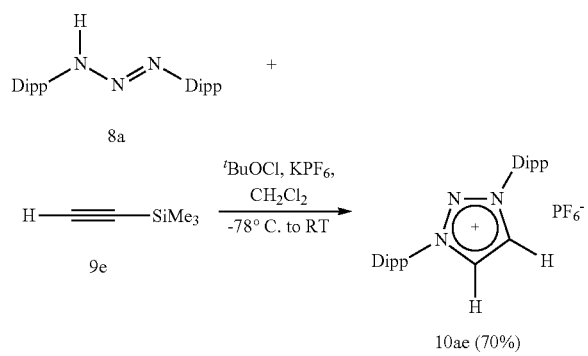

10ae (70%)

1,3-Bis(2,6-diisopropylphenyl)-1H-1,2,3-triazolium hexafluorophosphate (10ae). To a stirred suspension of triazene 8a (2196 mg, 6 mmol) and anhydrous potassium hexafluorophosphate (1500 mg, 8 mmol) in dry dichloromethane (40 mL) in the dark at −78° C. is added tert-butyl hypochlorite (1000 μL, 8.8 mmol), upon which the mixture instantly darkens. Stirring is pursued at −78° C. for 30 min, and trimethylsilylacetylene 9e (1300 μL, 10.2 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ae as an off-white solid (2.25 g, 70%). Analytical samples were obtained after recrystallization by vapor diffusion of diethyl ether in an acetonitrile solution of 10ae. $^1$H-NMR (CD$_3$CN, 300 MHz): δ=8.93 (s, 2H), 7.74 (t, J=7.9 Hz, 2H), 7.53 (d, J=7.9 Hz, 4H), 2.24 (sept, J=6.8 Hz, 4H), 1.28 (d, J=6.8 Hz, 12H), 1.16 (d, J=6.8 Hz, 12H). $^{13}$C-NMR (CD$_3$CN, 75 MHz): δ=146.4, 136.0, 134.5, 131.4, 126.1, 30.1, 24.7, 23.7. HR-MS (ESI): Calcd. for C$_{26}$H$_{36}$N$_3$ [M+]: 390.2904. found 390.2917.

Example 22

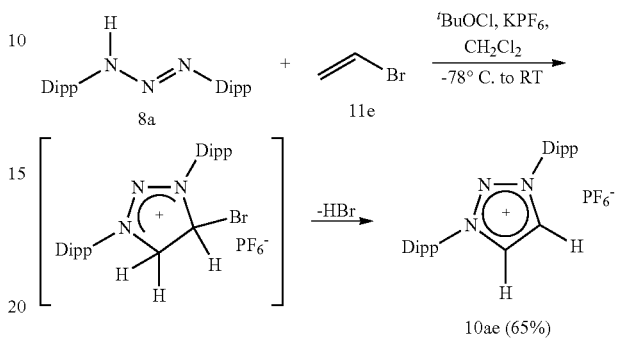

10ae (65%)

1,3-Bis(2,6-diisopropylphenyl)-1H-1,2,3-triazolium hexafluorophosphate (10ae), alternate preparation. To a stirred suspension of triazene 8ai (3.66 g, 10 mmol) and anhydrous potassium hexafluorophosphate (1.84 g, 10 mmol) and excess vinyl bromide 11e (5 mL) in dry dichloromethane (50 mL) in the dark at −78° C. is added tert-butyl hypochlorite (1.66 mL, 15 mmol), upon which the mixture instantly darkens. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ae as an off-white solid (3.49 g, 65%). Characterization data are identical as for 10ae prepared by the first method.

Example 23

1,3-Bis(2,6-diisopropylphenyl)-4-carboxymethyl-1H-1,2, 3-triazolium hexafluorophosphate (10af). To a stirred suspension of triazene 8a (1098 mg, 3 mmol) and anhydrous potassium hexafluorophosphate (750 mg, 4 mmol) in dry dichloromethane (20 mL) in the dark at −78° C. is added tert-butyl hypochlorite (500 μL, 4.4 mmol), upon which the mixture instantly darkens. Stirring is pursued at −78° C. for 30 min, and methyl propiolate 9f (500 μL, 5.6 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10af as an off-white solid (1.15 g, 65%). Analytical samples were obtained after recrystallization by vapor diffusion of diethyl ether in an acetonitrile solution of 10af. $^1$H-NMR (CD$_3$CN, 300 MHz): δ=9.42 (s, 1H), 7.77 (t, J=7.9 Hz, 1H), 7.74 (t, J=7.9 Hz, 1H), 7.54 (d, J=7.9 Hz, 2H), 7.51 (d, J=7.9 Hz, 2H), 3.94 (s, 3H), 2.32 (sept, J=6.8 Hz, 2H), 2.21 (sept, J=6.8 Hz, 2H), 1.29 (d, J=6.8 Hz, 6H), 1.20 (d, J=6.8 Hz, 6H), 1.13 (d, J=6.8 Hz, 6H), 1.09 (d, J=6.8 Hz, 6H). $^{13}$C-NMR (CD$_3$CN, 75 MHz): δ=155.5, 146.4, 146.2, 138.3, 137.2, 134.9, 134.4, 131.1, 131.0, 126.3, 126.2, 55.2, 30.1, 30.0, 25.1, 24.9, 23.8, 23.5. HR-MS (ESI): Calcd. for C$_{28}$H$_{38}$N$_3$O$_2$ [M+]: 448.2959. found 448.2974.

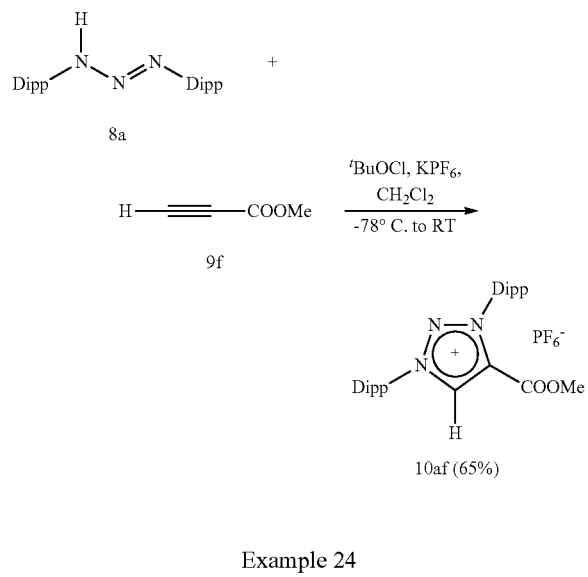

Example 24

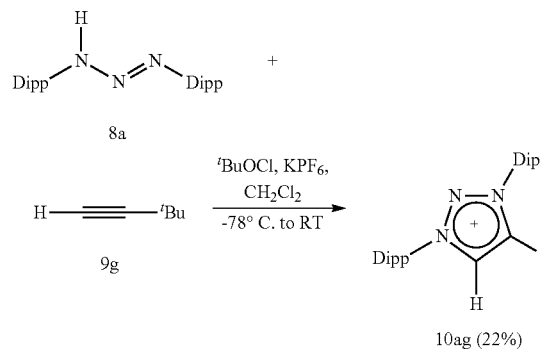

1,3-Bis(2,6-diisopropylphenyl)-4-tert-butyl-1H-1,2,3-triazolium hexafluorophosphate (10ag). To a stirred suspension of triazene 8a (1098 mg, 3 mmol) and anhydrous potassium hexafluorophosphate (750 mg, 4 mmol) in dry dichloromethane (20 mL) in the dark at −78° C. is added tert-butyl hypochlorite (500 μL, 4.4 mmol), upon which the mixture instantly darkens. Stirring is pursued at −78° C. for 30 min, and tert-butylacetylene 9 g (555 μL, 4.5 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ag as an off-white solid (0.40 g, 22%). Analytical samples were obtained after recrystallization by vapor diffusion of diethyl ether in an acetonitrile solution of 10ag. $^1$H-NMR (CD$_3$CN, 300 MHz): δ=8.83 (s, 1H), 7.78 (t, J=7.9 Hz, 1H), 7.74 (t, J=7.9 Hz, 1H), 7.54 (d, J=7.9 Hz, 2H), 7.51 (d, J=7.9 Hz, 2H), 2.24 (d sept, J=6.8 Hz, 4H), 1.35 (d, J=6.8 Hz, 6H), 1.33 (s, 9H), 1.27 (d, J=6.8 Hz, 6H), 1.18 (d, J=6.8 Hz, 6H), 1.04 (d, J=6.8 Hz, 6H). $^{13}$C-NMR (CD$_3$CN, 75 MHz): 155.7, 146.9, 146.4, 134.8, 134.4, 133.2, 131.8, 131.2, 126.2 (2), 33.9, 30.7, 29.8, 29.4, 26.9, 24.7, 24.5, 21.4. HR-MS (ESI): Calcd. for C$_{30}$H$_{44}$N$_3$ [M+]: 446.3530. found 446.3540.

Example 25

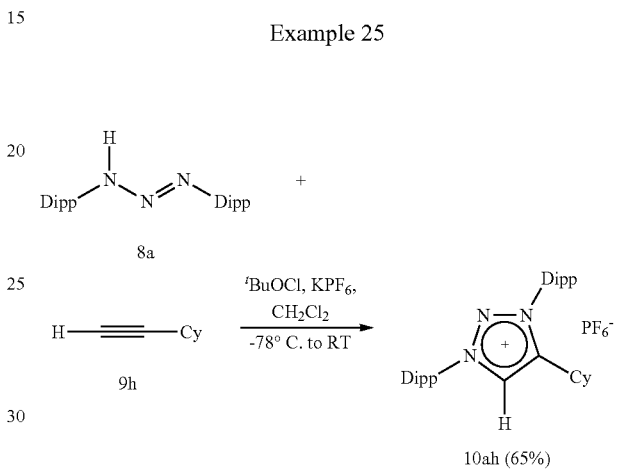

1,3-Bis(2,6-diisopropylphenyl)-4-cyclohexyl-1H-1,2,3-triazolium hexafluorophosphate (10ah). To a stirred suspension of triazene 8a (1098 mg, 3 mmol) and anhydrous potassium hexafluorophosphate (750 mg, 4 mmol) in dry dichloromethane (20 mL) in the dark at −78° C. is added tert-butyl hypochlorite (500 μL, 4.4 mmol), upon which the mixture instantly darkens. Stirring is pursued at −78° C. for 30 min, and cyclohexylacetylene 9 h (600 μL, 4.6 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ah as an off-white solid (1.21 g, 65%). Analytical samples were obtained after recrystallization by vapor diffusion of diethyl ether in an acetonitrile solution of 10ah. $^1$H-NMR (CD$_3$CN, 300 MHz): δ=8.83 (s, 1H), 7.78 (t, J=7.9 Hz, 1H), 7.74 (t, J=7.9 Hz, 1H), 7.56 (d, J=7.9 Hz, 2H), 7.52 (d, J=7.9 Hz, 2H), 2.57 (tt, J=11.7, 3.5 Hz, 1H), 2.24 (sept, J=6.8 Hz, 2H), 2.15 (sept, J=6.8 Hz, 2H), 1.96-1.89 (m, 2H), 1.80-1.76 (m, 2H), 1.68-1.56 (m, 2H), 1.31 (d, J=6.8 Hz, 6H), 1.27 (d, J=6.8 Hz, 6H), 1.14 (d, J=6.8 Hz, 6H), 1.09 (d, J=6.8 Hz, 6H). $^{13}$C-NMR (CD$_3$CN, 75 MHz): δ=153.1, 146.7, 146.4, 134.7, 134.4, 132.4, 131.6, 129.2, 126.6, 126.1, 34.8, 32.5, 30.3, 30.0, 26.04, 26.00, 25.8, 24.7, 24.1, 22.7. HR-MS (ESI): Calcd. for $C_{32}H_{46}N_3$ [M+]: 472.3686. found 472.3696.

Example 26

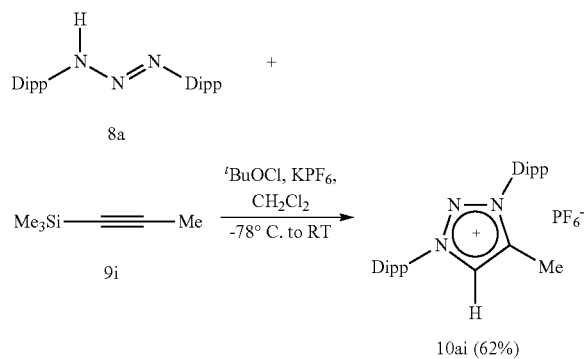

10ai (62%)

1,3-Bis(2,6-diisopropylphenyl)-4-methyl-1H-1,2,3-triazolium hexafluorophosphate (10ai). To a stirred suspension of triazene 8a (1098 mg, 3 mmol) and anhydrous potassium hexafluorophosphate (750 mg, 4 mmol) in dry dichloromethane (20 mL) in the dark at −78° C. is added tert-butyl hypochlorite (500 µL, 4.4 mmol), upon which the mixture instantly darkens. Stirring is pursued at −78° C. for 30 min, and 1-trimethylsilylprop-1-yne 9i (675 µL, 4.6 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ai as an off-white solid (1.02 g, 62%). Analytical samples were obtained after recrystallization by vapor diffusion of diethyl ether in an acetonitrile solution of 10ai. $^1$H-NMR (CD$_3$CN, 300 MHz): δ=8.69 (s, 1H), 7.76 (t, J=7.9 Hz, 1H), 7.73 (t, J=7.9 Hz, 1H), 7.55 (d, J=7.9 Hz, 2H), 7.51 (d, J=7.9 Hz, 2H), 2.38 (s, 3H), 2.32 (sept, J=6.8 Hz, 2H), 2.22 (sept, J=6.8 Hz, 2H), 1.28 (d, J=6.8 Hz, 12H), 1.14 (d, J=6.8 Hz, 6H), 1.10 (d, J=6.8 Hz, 6H). $^{13}$C-NMR (CD$_3$CN, 75 MHz): δ=146.7, 146.5, 145.4, 134.6, 134.3, 133.9, 131.6, 130.0, 126.9, 126.5, 126.0, 30.0, 29.9, 25.4, 24.8, 24.0, 23.2, 22.9, 10.4. HR-MS (ESI): Calcd. for $C_{27}H_{38}N_3$ [M+]: 404.3060. found 404.3059.

Example 27

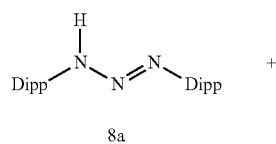

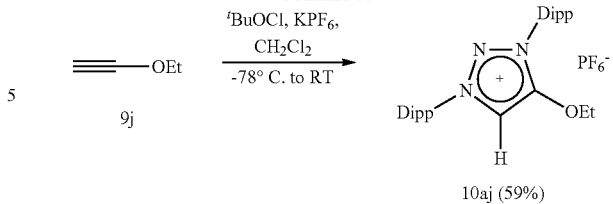

10aj (59%)

1,3-Bis(2,6-diisopropylphenyl)-4-ethoxy-1H-1,2,3-triazolium hexafluorophosphate (10aj). To a stirred suspension of triazene 8a (1098 mg, 3 mmol) and anhydrous potassium hexafluorophosphate (750 mg, 4 mmol) in dry dichloromethane (20 mL) in the dark at −78° C. is added tert-butyl hypochlorite (500 µL, 4.4 mmol), upon which the mixture instantly darkens. Stirring is pursued at −78° C. for 30 min, and ethoxyacetylene 9j (1100 µL, 40% by wt. in hexanes, 4.6 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10aj as an off-white solid (1.02 g, 59%). Analytical samples were obtained after recrystallization by vapor diffusion of diethyl ether in an acetonitrile solution of 10aj. $^1$H-NMR (CD$_3$CN, 300 MHz): δ=8.44 (s, 1H), 7.73 (t, J=7.9 Hz, 2H), 7.51 (d, J=7.9 Hz, 4H), 4.60 (q, J=7.1 Hz, 2H), 2.43 (sept, J=6.8 Hz, 2H), 2.39 (sept, J=6.8 Hz, 2H), 1.41 (t, J=7.1 Hz, 3H), 1.31 (d, J=6.8 Hz, 6H), 1.26 (d, J=6.8 Hz, 6H), 1.15 (d, J=6.8 Hz, 6H), 1.12 (d, J=6.8 Hz, 6H). $^{13}$C-NMR (CD$_3$CN, 75 MHz): δ=155.5, 147.3, 146.4, 134.6, 134.4, 132.3, 127.6, 126.3, 126.0, 116.5, 74.2, 30.1, 29.9, 25.1, 24.7, 23.9, 23.7, 14.5. HR-MS (ESI): Calcd. for $C_{28}H_{40}N_3O$ [M+]: 434.3166. found 434.3173.

Example 28

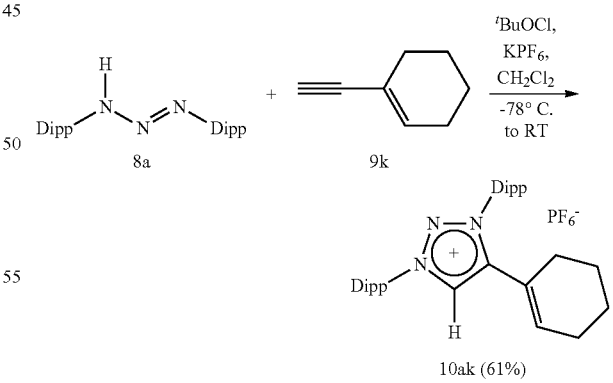

10ak (61%)

1,3-Bis(2,6-diisopropylphenyl)-4-(cyclohexen-1-yl)-1H-1,2,3-triazolium hexafluorophosphate (10ak). To a stirred suspension of triazene 8a (1098 mg, 3 mmol) and anhydrous potassium hexafluorophosphate (750 mg, 4 mmol) in dry dichloromethane (20 mL) in the dark at −78° C. is added tert-butyl hypochlorite (500 µL, 4.4 mmol), upon which the mixture instantly darkens. Stirring is pursued at −78° C. for 30 min, and cyclohexenylacetylene 9k (550 μL, 4.6 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ak as an off-white solid (1.12 g, 61%). Analytical samples were obtained after recrystallization by vapor diffusion of diethyl ether in an acetonitrile solution of 10ak. $^1$H-NMR (CD$_3$CN, 300 MHz): δ=8.79 (s, 1H), 7.75 (t, J=7.9 Hz, 1H), 7.73 (t, J=7.9 Hz, 1H), 7.54 (d, J=7.9 Hz, 2H), 7.51 (d, J=7.9 Hz, 2H), 6.13-6.10 (br m, 1H), 2.32 (sept, J=6.8 Hz, 2H), 2.29 (sept, J=6.8 Hz, 2H), 2.15-2.12 (m, 2H), 2.10-2.07 (m, 2H), 1.71-1.63 (m, 2H), 1.58-1.51 (m, 2H), 1.28 (d, J=6.8 Hz, 6H), 1.25 (d, J=6.8 Hz, 6H), 1.14 (d, J=6.8 Hz, 6H), 1.10 (d, J=6.8 Hz, 6H). $^{13}$C-NMR (CD$_3$CN, 75 MHz): δ=147.7, 146.41, 146.35, 139.8, 134.5, 134.4, 131.6, 131.5, 131.2, 126.7, 126.1, 122.5, 30.2, 29.9, 27.4, 26.7, 25.4, 24.9, 24.0, 22.9, 22.6, 21.6 HR-MS (ESI): Calcd. for C$_{32}$H$_{44}$N$_3$ [M+]: 470.3530. found 470.3532.

Example 29

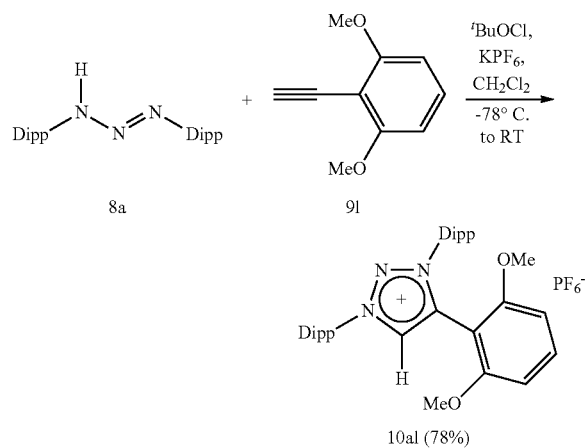

10al (78%)

1,3-Bis(2,6-diisopropylphenyl)-4-(2,6-dimethoxyphenyl)-1H-1,2,3-triazolium hexafluorophosphate (10al). To a stirred suspension of triazene 8a (3.66 g, 10 mmol), 2,6-dimethoxyphenylacetylene 9l (3.24 g, 20 mmol), and anhydrous potassium hexafluorophosphate (1.84 g, 10 mmol) in dry dichloromethane (50 mL) in the dark at −78° C. is added tert-butyl hypochlorite (1.66 mL, 15 mmol), upon which the mixture instantly darkens. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ai as an off-white solid (5.25 g, 78%). Analytical samples were obtained after recrystallization by vapor diffusion of diethyl ether in an acetonitrile solution of 10ai. $^1$H-NMR ((CD$_3$)$_2$SO, 300 MHz): δ=10.03 (s, 1H), 7.79 (t, J=7.9 Hz, 1H), 7.64-7.57 (m, 3H), 7.54 (t, J=7.9 Hz, 1H), 7.42 (d, J=7.9 Hz, 2H), 6.78 (d, J=8.5 Hz, 2H), 3.71 (s, 6H), 2.43 (sept, J=6.8 Hz, 2H), 2.29 (sept, J=6.8 Hz, 2H), 1.27 (d, J=6.8 Hz, 6H), 1.17 (d, J=6.8 Hz, 6H), 1.08 (d, J=6.8 Hz, 6H), 0.99 (d, J=6.8 Hz, 6H). $^{13}$C-NMR ((CD$_3$)$_2$SO, 75 MHz): δ=158.4, 145.2, 144.7, 139.9, 136.4, 135.2, 133.3, 132.9, 130.2, 129.2, 125.0, 124.8, 104.7, 98.0, 56.9, 28.8, 28.6, 25.8, 23.8, 23.1, 21.7. HR-MS (ESI): Calcd. for C$_{34}$H$_{44}$N$_3$O$_2$ [M+]: 526.3428. found 526.3433.

Example 30

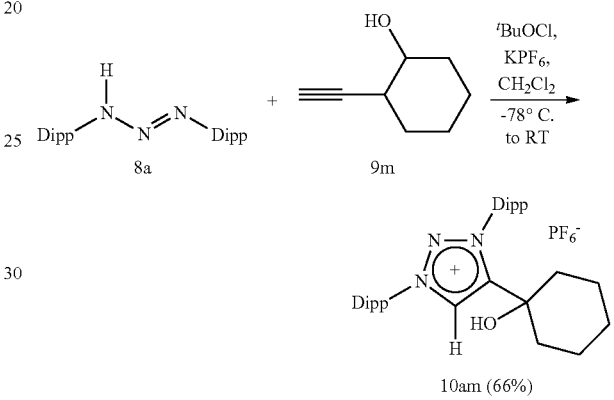

10am (66%)

1,3-Bis(2,6-diisopropylphenyl)-4-(cyclohexen-1-yl)-1H-1,2,3-triazolium hexafluorophosphate (10 am). To a stirred suspension of triazene 8a (1098 mg, 3 mmol) and anhydrous potassium hexafluorophosphate (750 mg, 4 mmol) in dry dichloromethane (20 mL) in the dark at −78° C. is added tert-butyl hypochlorite (500 μL, 4.4 mmol), upon which the mixture instantly darkens. Stirring is pursued at −78° C. for 30 min, and 1-ethynylcyclohexan-1-ol 9m (600 μL, 4.6 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10 am as an off-white solid (1.25 g, 66%). Analytical samples were obtained after recrystallization by vapor diffusion of diethyl ether in an acetonitrile solution of 10 am. $^1$H-NMR (CD$_3$CN, 300 MHz): δ=8.86 (s, 1H), 7.75 (t, J=7.9 Hz, 1H), 7.71 (t, J=7.9 Hz, 1H), 7.52 (d, J=7.9 Hz, 2H), 7.49 (d, J=7.9 Hz, 2H), 3.99 (br s, 1H), 2.30-2.21 (m, 5H), 1.95-1.83 (m, 4H), 1.63-1.51 (m, 5H), 1.32 (d, J=6.8 Hz, 6H), 1.27 (d, J=6.8 Hz, 6H), 1.18 (d, J=6.8 Hz, 6H), 1.04 (d, J=6.8 Hz, 6H). $^{13}$C-NMR (CD$_3$CN, 75 MHz): δ=153.9, 150.0, 146.4, 134.4, 134.3, 132.8, 131.9, 131.3, 126.1, 125.8, 70.6, 36.8, 30.7, 29.9, 26.6, 25.3, 24.6, 24.5, 21.8, 21.7. HR-MS (ESI): Calcd. for $C_{32}H_{46}N_3O$ [M+]: 488.3635. found 488.3640.

Example 31

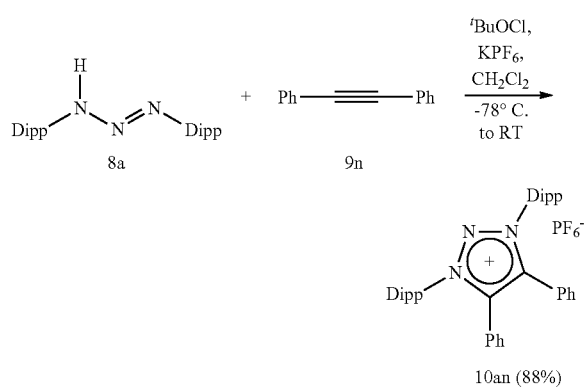

10an (88%)

1,3-Bis(2,6-diisopropylphenyl)-4,5-diphenyl-1H-1,2,3-triazolium hexafluorophosphate (10an). To a stirred suspension of triazene 8a (1098 mg, 3 mmol), diphenylacetylene 9n (801 mg, 4.5 mmol), and anhydrous potassium hexafluorophosphate (750 mg, 4 mmol) in dry dichloromethane (20 mL) in the dark at −78° C. is added tert-butyl hypochlorite (500 mL, 4.6 mmol), upon which the mixture instantly darkens. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10an as an off-white solid (1.82 g, 88%). Analytical samples were obtained after recrystallization by vapor diffusion of diethyl ether in an acetonitrile solution of 10an. $^1$H-NMR (CD$_3$CN, 300 MHz): δ=7.69 (t, J=7.9 Hz, 1H), 7.53-7.45 (m, 6H), 7.39 (t, J=7.9 Hz, 4H), 7.31-7.28 (m, 4H), 2.58 (sept, J=6.8 Hz, 4H), 1.15 (d, J=6.8 Hz, 12H), 1.04 (d, J=6.8 Hz, 12H). $^{13}$C-NMR (CD$_3$CN, 75 MHz): δ=146.9, 143.4, 134.5, 133.0, 131.3, 130.2, 130.1, 126.5, 122.8, 30.0, 26.1, 22.7. HR-MS (ESI): Calcd. for $C_{38}H_{44}N_3$ [M+]: 542.3530. found 542.3536.

Example 32

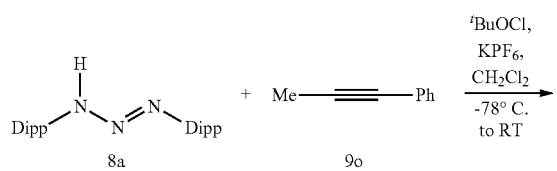

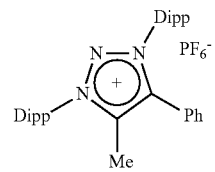

10ao (70%)

1,3-Bis(2,6-diisopropylphenyl)-4-phenyl-5-methyl-1H-1,2,3-triazolium hexafluorophosphate (10ao). To a stirred suspension of triazene 8a (1098 mg, 3 mmol) and anhydrous potassium hexafluorophosphate (750 mg, 4 mmol) in dry dichloromethane (20 mL) in the dark at −78° C. is added tert-butyl hypochlorite (500 μL, 4.4 mmol), upon which the mixture instantly darkens. Stirring is pursued at −78° C. for 30 min, and 1-phenylprop-1-yne 9o (600 μL, 4.8 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ao as an off-white solid (1.31 g, 70%). Analytical samples were obtained after recrystallization by vapor diffusion of diethyl ether in an acetonitrile solution of 10ao. $^1$H-NMR (CD$_3$CN, 300 MHz): δ=7.79 (t, J=7.9 Hz, 1H), 7.67 (t, J=7.9 Hz, 1H), 7.59 (d, J=7.9 Hz, 2H), 7.56-7.46 (m, 5H), 7.44 (d, J=7.9 Hz, 2H), 2.43 (s, 3H), 2.41 (sept, J=6.8 Hz, 4H), 1.32 (d, J=6.8 Hz, 6H), 1.15 (d, J=6.8 Hz, 6H), 1.10 (d, J=6.8 Hz, 6H), 1.04 (d, J=6.8 Hz, 6H). $^{13}$C-NMR (CD$_3$CN, 75 MHz): δ=146.9, 146.7, 142.2, 134.6, 134.4, 133.0, 130.9, 130.4, 130.2, 129.4, 126.7, 126.4, 123.1, 30.1, 29.9, 26.1, 25.6, 23.6, 22.7, 10.7. HR-MS (ESI): Calcd. for $C_{33}H_{42}N_3$ [M+]: 480.3373. found 480.3378.

Example 33

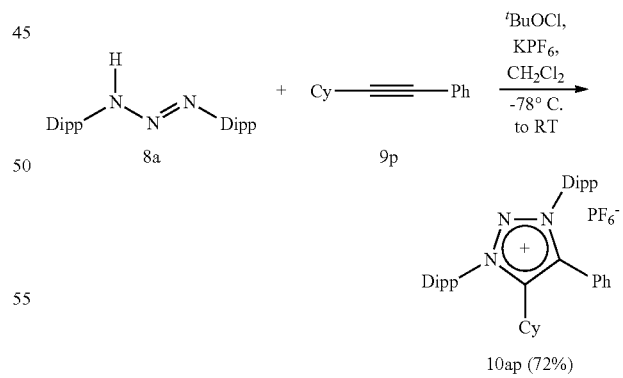

10ap (72%)

1,3-Bis(2,6-diisopropylphenyl)-4-phenyl-5-cyclohexyl-1H-1,2,3-triazolium hexafluorophosphate (10ap). To a stirred suspension of triazene 8a (1098 mg, 3 mmol) and anhydrous potassium hexafluorophosphate (750 mg, 4 mmol) in dry dichloromethane (20 mL) in the dark at −78° C. is added tert-butyl hypochlorite (500 μL, 4.4 mmol), upon which the mixture instantly darkens. Stirring is pursued at −78° C. for 30 min, and cyclohexylphenylacetylene 9p (900 μL, 4.9 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ap as an off-white solid (1.50 g, 72%). Analytical samples were obtained after recrystallization by vapor diffusion of diethyl ether in an acetonitrile solution of 10ap. $^1$H-NMR (CD$_3$CN, 300 MHz): δ=7.80 (t, J=7.9 Hz, 1H), 7.60 (d, J=7.9 Hz, 2H), 7.58-7.52 (m, 6H), 7.36 (d, J=7.9 Hz, 2H), 2.60 (tt, J=12.4, 3.0 Hz, 1H), 2.42 (sept, J=6.8 Hz, 2H), 2.35 (sept, J=6.8 Hz, 2H), 1.91-1.86 (m, 2H), 1.65-1.60 (m, 2H), 1.53-1.43 (m, 1H), 1.40-1.32 (m, 2H), 1.35 (d, J=6.8 Hz, 6H), 1.20 (d, J=6.8 Hz, 6H), 1.16 (d, J=6.8 Hz, 6H), 1.11-1.06 (m, 2H), 1.09 (d, J=6.8 Hz, 6H), 0.97-0.87 (m, 1H). $^{13}$C-NMR (CD$_3$CN, 75 MHz): δ=148.7, 147.0, 146.8, 143.8, 134.7, 134.3, 133.3, 131.8, 130.2, 129.6, 129.1, 126.8, 126.2, 123.0, 36.6, 31.9, 30.2, 30.1, 26.7, 26.45, 26.36, 25.8, 23.3, 22.8. HR-MS (ESI): Calcd. for C$_{38}$H$_{50}$N$_3$ [M+]: 548.3999. found 548.4008.

Example 34

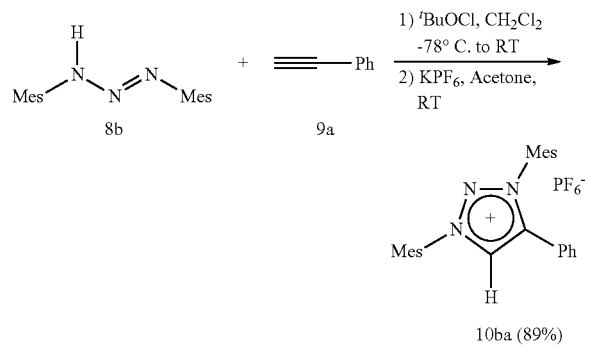

10ba (89%)

1,3-Bis(2,4,6-trimethylphenyl)-4-phenyl-1H-1,2,3-triazolium hexafluorophosphate (10ba). To a stirred suspension of triazene 8b (845 mg, 3 mmol) and phenylacetylene 9a (660 μL, 6 mmol) in dry dichloromethane (20 mL) in the dark at −78° C. is added tert-butyl hypochlorite (500 μL, 4.4 mmol), upon which the mixture instantly darkens. The mixture is stirred overnight as it is slowly allowed to warm to room temperature. The contents are then filtered, and the solid residue is washed with dichloromethane. The filtrate is collected, and volatiles are evaporated under reduced pressure. The crude solid is redissolved in acetone (20 mL), to which is then added potassium hexafluorophosphate (750 mg, 4 mmol). The mixture is stirred at room temperature for ca. 1 hour, filtered, and the solid residue is washed with dichloromethane. The collected filtrate is evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ba as an off-white solid (1.42 g, 89%). Analytical samples were obtained after recrystallization by vapor diffusion of diethyl ether in an acetonitrile solution of 10ba. $^1$H-NMR (CD$_3$CN, 300 MHz): δ=9.03 (s, 1H), 7.61 (tt, J=7.2, 1.5 Hz, 1H), 7.53-7.43 (m, 4H), 7.24 (s, 2H), 7.20 (s, 2H), 2.42 (s, 3H), 2.39 (s, 3H), 2.21 (s, 6H), 2.04 (s, 6H). $^{13}$C-NMR (CD$_3$CN, 75 MHz): δ=145.9, 144.7, 144.4, 136.0, 135.6, 133.5, 132.5, 131.3, 131.0, 130.8, 129.5, 122.9, 21.4, 17.7, 17.6. HR-MS (ESI): Calcd. for C$_{26}$H$_{28}$N$_3$ [M+]: 382.2278. found 382.2288.

Example 35

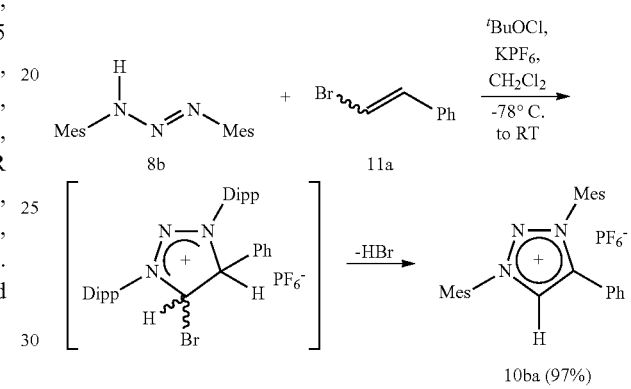

10ba (97%)

1,3-Bis(2,4,6-trimethylylphenyl)-4-phenyl-1H-1,2,3-triazolium hexafluorophosphate (10ba), alternate preparation. To a stirred suspension of triazene 8b (5.63 g, 20 mmol) and anhydrous potassium hexafluorophosphate (3.68 g, 10 mmol) and β-bromostyrene 11a (mixture of isomers, 5.13 mL, 40 mmol) in dry dichloromethane (100 mL) in the dark at −78° C. is added tert-butyl hypochlorite (3.33 mL, 30 mmol), upon which the mixture instantly darkens. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ba as an off-white solid (10.21 g, 97%). Analytical samples were obtained after recrystallization by vapor diffusion of diethyl ether in an acetonitrile solution of 10ba. Characterization data are identical as for 10ba prepared by the first method.

Example 36

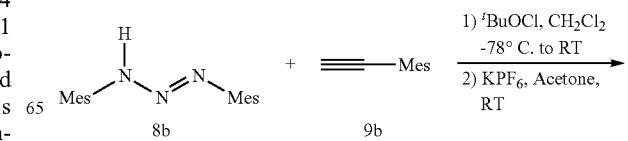

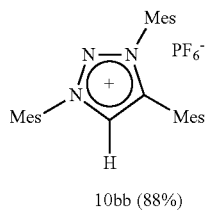

10bb (88%)

1,3,4-Tris(2,4,6-trimethylphenyl)-1H-1,2,3-triazolium hexafluorophosphate (10bb). To a stirred suspension of triazene 8b (5.63 g, 20 mmol) and mesitylacetylene 9b (5.76 g, 40 mmol) in dry dichloromethane (100 mL) in the dark at −78° C. is added tert-butyl hypochlorite (3.33 mL, 30 mmol), upon which the mixture instantly darkens. The mixture is stirred overnight as it is slowly allowed to warm to room temperature. Volatiles are evaporated under reduced pressure, and the crude solid is redissolved in acetone (50 mL), to which is then added potassium hexafluorophosphate (3.68 g, 20 mmol). The mixture is stirred at room temperature for ca. 1 hour, filtered, and the solid residue is washed with dichloromethane. The collected filtrate is evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10bb as an off-white solid (10.10 g, 88%). Analytical samples were obtained after recrystallization by vapor diffusion of diethyl ether in an acetonitrile solution of 10bb. $^1$H-NMR (CD$_3$CN, 300 MHz): δ=8.94 (s, 1H), 7.27 (s, 2H), 7.10 (s, 2H), 7.05 (s, 2H), 2.43 (s, 3H), 2.31 (s, 3H), 2.28 (s, 3H), 2.25 (s, 6H), 2.17 (s, 6H), 2.06 (s, 6H). $^{13}$C-NMR (CD$_3$CN, 75 MHz): δ=145.2, 144.5, 144.3, 143.9, 139.6, 135.7, 135.2, 132.4, 131.7, 131.5, 131.3, 131.1, 130.9, 119.0, 21.5, 21.4, 21.3, 19.1, 17.9. HR-MS (ESI): Calcd. for C$_{29}$H$_{34}$N$_3$ [M+]: 424.2747. found 424.2758.

Example 37

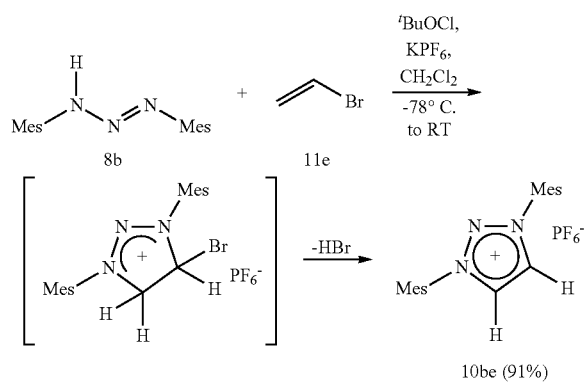

10be (91%)

1,3-Bis(2,4,6-trimethylphenyl)-1H-1,2,3-triazolium hexafluorophosphate (10be). To a stirred suspension of triazene 8b (5.63 g, 20 mmol) and anhydrous potassium hexafluorophosphate (3.68 g, 20 mmol) and excess vinyl bromide 11e (10 mL) in dry dichloromethane (100 mL) in the dark at 78° C. is added tert-butyl hypochlorite (3.33 mL, 30 mmol), upon which the mixture instantly darkens. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10be as an off-white solid (8.21 g, 91%). $^1$H-NMR (CD$_3$CN, 300 MHz): δ=8.82 (s, 2H), 7.21 (s, 4H), 2.40 (s, 6H), 2.09 (s, 12H). $^{13}$C-NMR (CD$_3$CN, 75 MHz): δ=144.3, 135.7, 135.1, 132.3, 130.9, 21.4, 17.5. HR-MS (ESI): Calcd. for C$_{20}$H$_{24}$N$_3$ [M+]: 306.1965. found 306.1973.

Example 38

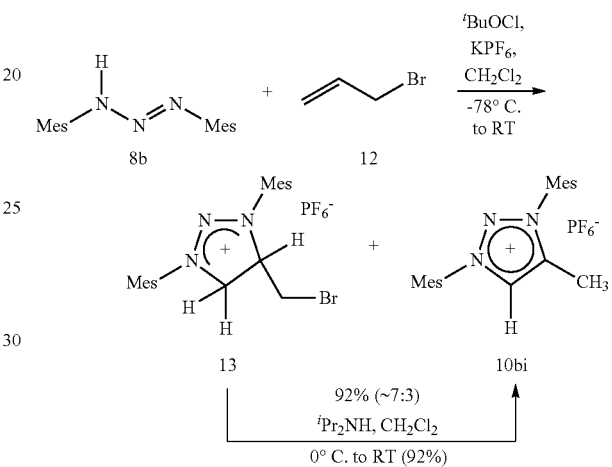

1,3-Bis(2,4,6-trimethylphenyl)-4-methyl-1H-1,2,3-triazolium hexafluorophosphate (10bi). To a stirred suspension of triazene 8b (1.70 g, 6 mmol) and anhydrous potassium hexafluorophosphate (1.10 g, 6 mmol) and allyl bromide 12 (1.04 mL, 12 mmol) in dry dichloromethane (20 mL) in the dark at −78° C. is added tert-butyl hypochlorite (1.0 mL, 9 mmol), upon which the mixture instantly darkens. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether affords the crude dihydrotriazolium salt 13 as a beige solid (3.02 g, ~92%), which is contaminated by ca. 30% of the aromatized triazolium salt 10bi. $^1$H-NMR (CDCl$_3$, 300 MHz): δ=7.07 (s, 2H), 7.06 (s, 2H), 6.03 (t, J=12.7 Hz), 5.20 (t, J=14.9 Hz, 1H), 4.85 (t, J=12.5 Hz, 1H), 3.91 (dd, J=12.8, 2.5 Hz, 1H), 3.68 (d, J=12.6 Hz, 1H), 2.45-2.36 (m, 18H). $^{13}$C-NMR (CDCl$_3$, 75 MHz): δ=142.8, 142.6, 135.9, 134.8, 134.3, 134.1, 132.2, 131.2, 130.5, 128.8, 68.3, 59.1, 30.1, 21.3, 21.2, 19.0, 18.7, 17.8. Calcd. for C$_{21}$H$_{27}$BrN$_3$ [M+]: 400.1383. found 400.1400.

To a stirred solution of the crude dihydrotriazolium salt 13 (2.70 g, 5 mmol) in dichloromethane (20 mL) at 0° C. is added diisopropylamine (2 mL). The mixture is stirred for 2 h as it is slowly allowed to warm to room temperature. Volatiles are evaporated under reduced pressure, and contents are redissolved in dichloromethane. The organic layer is washed with 2N aqueous HCl, then saturated aqueous NaCl. Evaporation of the solvents under reduced pressure affords the crude triazolium salt that is further purified by trituration in diethyl ether, filtration and drying under vacuum to afford 10bi (2.12 g, 92%) as an off-white solid. $^1$H-NMR (CDCl$_3$, 300 MHz): δ=8.63 (s, 1H), 7.15 (s, 2H), 7.09 (s, 2H), 2.48 (s, 3H), 2.43 (s, 3H), 2.40 (s, 3H), 2.13 (s, 6H), 2.07 (s, 6H). $^{13}$C-NMR (CD$_3$CN, 75 MHz): δ=144.7, 144.5, 144.1, 136.1, 135.6, 133.2, 132.5, 131.2, 130.9, 129.9, 21.49, 21.45, 17.43, 17.38, 9.7. HR-MS (ESI): Calcd. for C$_{21}$H$_{26}$N$_3$ [M+]: 320.2121. found 320.2136.

Example 39

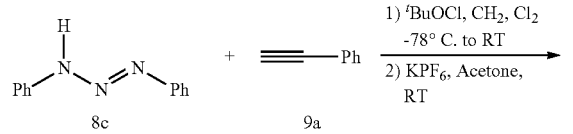

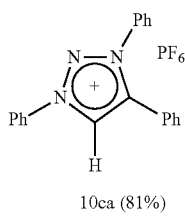

1,3,4-Triphenyl-1H-1,2,3-triazolium hexafluorophosphate (10ca). To a stirred suspension of triazene 8c (591 mg, 3 mmol) and phenylacetylene 9a (6604, 6 mmol) in dry dichloromethane (10 mL) in the dark at −78° C. is added tert-butyl hypochlorite (500 μL, 4.4 mmol), upon which the mixture instantly darkens. The mixture is stirred overnight as it is slowly allowed to warm to room temperature. Acetone (10 mL), and potassium hexafluorophosphate (550 mg, 3 mmol) are added to the mixture, and stirring is continued at room temperature for ca. 1 hour. The mixture is then filtered, and the solid residue is washed with acetone and dichloromethane. The collected filtrate is evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10ca as an off-white solid (1.07 g, 81%). Analytical samples were obtained after recrystallization by vapor diffusion of diethyl ether in an acetonitrile solution of 10ca. $^1$H-NMR (CD$_3$CN, 300 MHz): δ=9.13 (s, 1H), 8.05 (dd, J=7.1, 3.5 Hz, 2H), 7.79-7.70 (m, 4H), 7.65-7.59 (m, 5H), 7.52-7.46 (m, 4H). $^{13}$C-NMR (CD$_3$CN, 75 MHz): δ=145.1, 136.1, 135.1, 133.5, 133.4, 133.0, 131.7, 131.3, 130.5 (2), 128.4, 127.0, 123.3, 123.0. HR-MS (ESI): Calcd. for C$_{20}$H$_{16}$N$_3$ [M+]: 298.1339. found 298.1341.

Example 40

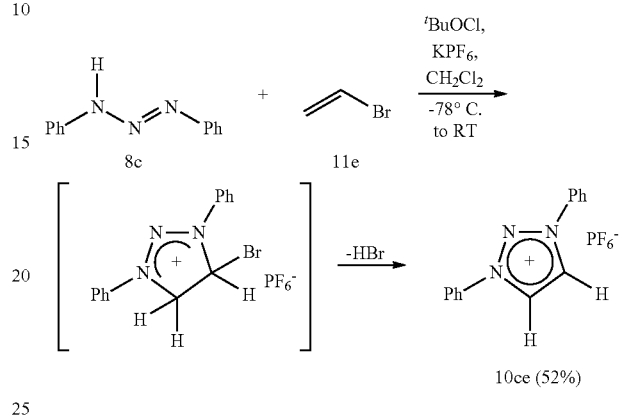

1,3-Diphenyl-1H-1,2,3-triazolium hexafluorophosphate (10ce). To a stirred suspension of triazene 8c (1.18 g, 6 mmol) and anhydrous potassium hexafluorophosphate (1.50 g, 8 mmol) and excess vinyl bromide 11e (5 mL) in dry dichloromethane (20 mL) in the dark at −78° C. is added tert-butyl hypochlorite (1.0 mL, 9 mmol), upon which the mixture instantly darkens. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. The mixture is filtered, and the collected solid are washed with copious quantities of diethyl ether. The crude solids are further purified by trituration in hot ethyl acetate, followed by drying under vacuum, to afford triazolium salt 10ce as a yellow solid (1.15 g, 52%). $^1$H-NMR (CD$_3$CN, 300 MHz): δ=8.98 (s, 2H), 8.03-7.96 (m, 4H), 7.77-7.72 (m, 6H). $^{13}$C-NMR (CD$_3$CN, 75 MHz): δ=136.1, 133.5, 131.6, 130.7, 123.1. HR-MS (ESI): Calcd. for C$_{14}$H$_{12}$N$_3$ [M+]: 222.1026. found 222.1032.

Example 41

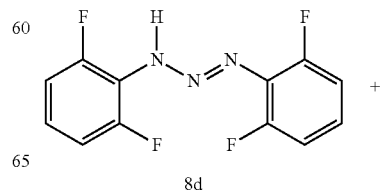

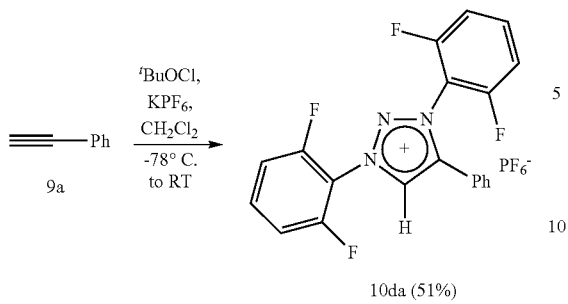

10da (51%)

1,3-Bis(2,6-difluorophenyl)-4-phenyl-1H-1,2,3-triazolium hexafluorophosphate (10da). To a stirred suspension of triazene 8d (808 mg, 3 mmol) and anhydrous potassium hexafluorophosphate (750 mg, 4 mmol) in dry dichloromethafne (20 mL) in the dark at −78° C. is added tert-butyl hypochlorite (500 μL, 4.4 mmol), upon which the mixture instantly darkens. Stirring is pursued at −78° C. for 30 min, and phenylacetylene 9a (660 μL, 6 mmol) is added. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10da as an off-white solid (0.79 g, 51%). Analytical samples were obtained after recrystallization by vapor diffusion of diethyl ether in an chloroform solution of 10da. $^1$H-NMR (CD$_3$CN, 300 MHz): δ=9.23 (s, 1H), 7.94-7.83 (m, 2H), 7.70-7.66 (m, 1H), 7.63-7.53 (m, 4H), 7.47 (t, J=7.9 Hz, 2H), 7.37 (td, J=8.0, 3.3 Hz, 2H). $^{13}$C-NMR (CD$_3$CN, 75 MHz): δ=157.7 (d, J=258 Hz), 157.0 (d, J=257 Hz), 147.3, 137.6 (t, J=10 Hz), 136.9 (t, J=10 Hz), 133.9, 133.1, 130.9, 130.0, 122.1, 114.9 (d, J=21 Hz), 114.7 (d, J=22 Hz), 113.7 (t, J=8 Hz), 111.9 (t, J=8 Hz). 19F-NMR (CD$_3$CN, 282 MHz): δ=−72.0 (d, J=705 Hz, 6F), −117.4 (2F), −119.2 (2F). HR-MS (ESI): Calcd. for C$_{20}$H$_{12}$F$_4$N$_3$ [M+]: 370.0962. found 370.0967.

Example 42

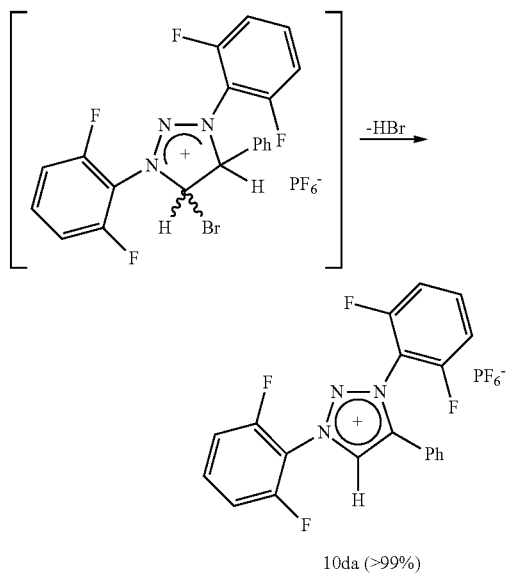

10da (>99%)

1,3-Bis(2,6-difluorophenyl)-4-phenyl-1H-1,2,3-triazolium hexafluorophosphate (10da), alternate preparation. To a stirred suspension of triazene 8d (808 mg, 3 mmol) and anhydrous potassium hexafluorophosphate (750 mg, 4 mmol) and β-bromostyrene 11a (mixture of isomers, 770 μL, 6 mmol) in dry dichloromethane (20 mL) in the dark at −78° C. is added tert-butyl hypochlorite (500 μL, 4.4 mmol), upon which the mixture instantly darkens. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10da as a white solid (1.55 g, 100%). Analytical samples were obtained after recrystallization by vapor diffusion of diethyl ether in an acetonitrile solution of 10da. Characterization data are identical as for 10da prepared by the first method.

Example 43

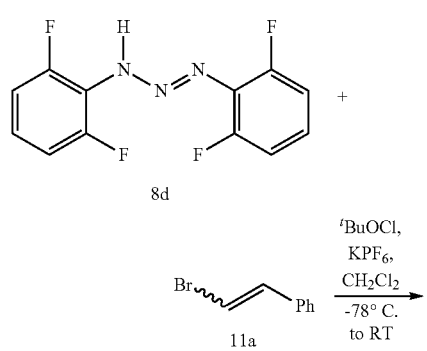

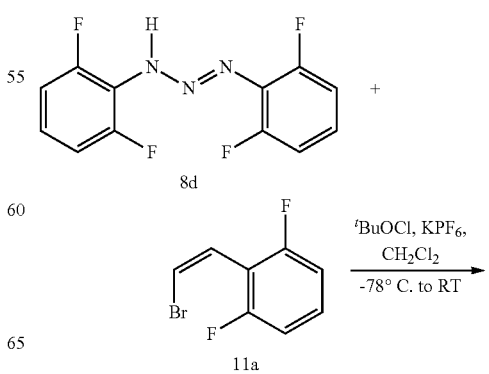

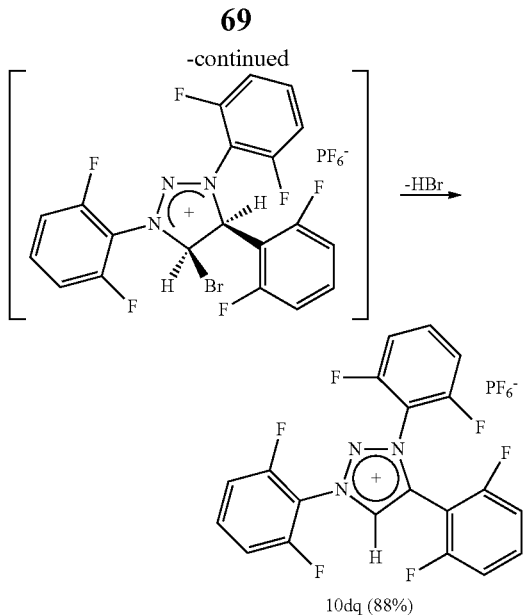

10dq (88%)

1,3,4-Tris(2,6-difluorophenyl)-1H-1,2,3-triazolium hexafluorophosphate (10dq). To a stirred suspension of triazene 8d (808 mg, 3 mmol) and anhydrous potassium hexafluorophosphate (750 mg, 4 mmol) and (Z)-1-Bromo-2-(2,6-difluorophenyl)ethene 11q (1.32 g, 6 mmol) in dry dichloromethane (20 mL) in the dark at −78° C. is added tert-butyl hypochlorite (500 μL, 4.4 mmol), upon which the mixture instantly darkens. The mixture is stirred overnight as it is slowly allowed to warm to room temperature. The contents are then filtered, and the solid residue is washed with dichloromethane. The filtrate is collected, and volatiles are evaporated under reduced pressure. Diethyl ether is then added, and the mixture is vigorously triturated for ca. 1 hour, with occasional scratching of the glass surfaces to ensure efficient mixing. Filtration and washing with copious quantities of diethyl ether afford, after drying under vacuum, triazolium salt 10dq as an off-white solid (1.45 g, 88%). Analytical samples were obtained after recrystallization by vapor diffusion of diethyl ether in an acetonitrile solution of 10dq. $^1$H-NMR (($CD_3$)$_2$SO, 300 MHz): δ=10.37 (s, 1H), 8.05-7.90 (m, 2H), 7.89-7.81 (m, 1H), 7.69 (t, J=8.9 Hz, 2H), 7.61 (t, J=8.9 Hz, 2H), 7.44 (t, J=8.9 Hz, 2H). $^{13}$C-NMR ((($CD_3$)$_2$SO, 75 MHz): δ=159.4 (dd, J=253, 4 Hz), 155.7 (d, J=257 Hz), 155.3 (d, J=257 Hz), 137.1 (2t, J=10 Hz), 136.2, 135.9 (t, J=10 Hz), 134.6, 114.0 (d, J=18 Hz), 113.8 (d, J=18 Hz), 113.0 (d, J=20 Hz), 112.6 (t, J=14 Hz), 110.3 (t, J=15 Hz), 99.1 (t, J=18 Hz). 19F-NMR ($CD_3$CN, 282 MHz): δ=−71.9 (d, J=705 Hz, 6F), −110.3 (2F), −118.8 (2F), −119.0 (2F). HR-MS (ESI): Calcd. for $C_{20}H_{10}F_6N_3$ [M+]: 406.0773. found 406.0784.

Example 44

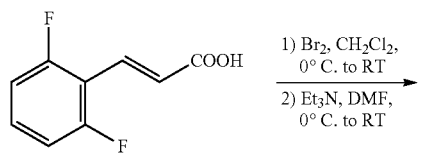

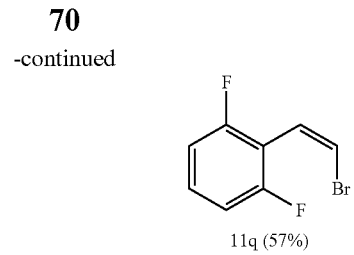

11q (57%)

(Z)-1-Bromo-2-(2,6-difluorophenyl)ethene (11q). To a stirred suspension of E-2,6-difluorocinnamic acid (2.0 g, 11 mmol) in dichloromethane at 0° C. is added bromine (0.56 mL, 11 mmol) dropwise. The mixture is stirred overnight as it is slowly allowed to reach temperature. Evaporation of the volatiles under reduced pressure affords the crude dibrominated carboxylic acid intermediate that is directly carried to the next step without further purification. To the crude solid is added DMF (20 mL) and a small crystal of BHT. The mixture is cooled to 0° C., and triethylamine (3 mL) is added. The mixture is stirred overnight as it is slowly allowed to reach temperature. Contents are poured in 2N aqueous HCl, extracted with diethyl ether, and the combined organic fractions are washed with saturated aqueous NaCl. Evaporation of the volatiles yields a crude product that is further purified by passing on a $SiO_2$ plug using pentane as an eluent. Evaporation of the solvents under reduced pressure affords bromoalkene 11q as a colorless oil (1.35 g, 57%, ≥20:1 d.r. by 19F-NMR). $^1$H-NMR (CDCl$_3$, 300 MHz): δ=7.42-7.32 (m, 1H), 7.07 (d, J=7.9 Hz, 1H), 7.05-6.95 (m, 2H), 6.84 (d, J=7.9 Hz, 1H). $^{13}$C-NMR (CDCl$_3$, 75 MHz): δ=159.9 (dd, J=250, 7 Hz), 130.0 (t, J=10 Hz), 122.3, 114.8, 130.0 (t, J=20 Hz), 111.5 (dd, J=18, 7 Hz). 19F-NMR (CDCl$_3$, 282 MHz): δ=−108.5. HR-MS (EI): Calcd. for $C_8H_5F_2Br$ [M+]: 217.9543. found 217.9538.

Example 45

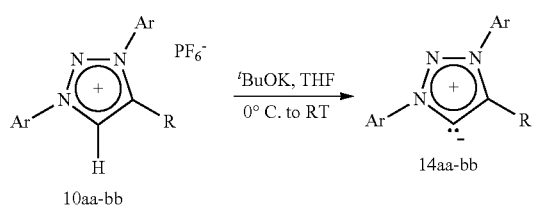

10aa-bb        14aa-bb

General procedure for the preparation of MICs 14aa-bb by deprotonation of triazolium salts 10aa-bb. Anhydrous THF is added to a stirred mixture of triazolium salt 10aa-bb and potassium tert-butoxide at 0° C. The reaction mixture is stirred for 30 min at 0° C., then warmed to room temperature while stirring for an additional 30 min. Volatiles are evaporated under reduced pressure, and dry benzene (or toluene) is added. The mixture is triturated for 15-30 mins, and filtered through a filter cannula. Evaporation of the solvents under reduced pressure affords the solid MICs 14aa-bb.

Example 46

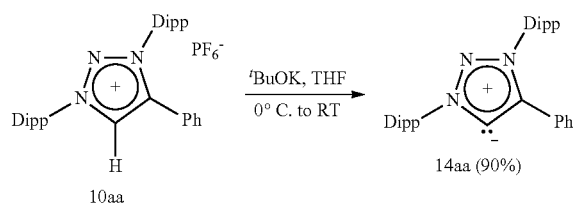

1,3-Bis(2,6-diisopropylphenyl)-4-phenyl-1H-1,2,3-triazol-5-ylidene (14aa). Following the general procedure with 10aa (306 mg, 0.5 mmol), potassium tert-butoxide (112 mg, 1.0 mmol) in THF (10 mL), extraction/tritutation in PhMe (20 mL) yields after filtration and evaporation of the volatiles 14aa (210 mg, 90%) as a yellow solid. $^1$H-NMR($C_6D_6$, 300 MHz): δ=8.05 (dd, J=8.5, 1.5 Hz, 2H), 7.34 (dd, J=8.5, 7.5 Hz), 7.25-7.20 (m, 3H), 7.05 (d, J=7.8 Hz, 2H), 7.02-6.90 (m, 3H), 3.11 (sept, J=6.9 Hz, 2H), 2.66 (sept, J=6.9 Hz, 2H), 1.33 (d, J=6.9 Hz, 6H), 1.21 (d, J=6.9 Hz, 6H), 1.09 (d, J=6.9 Hz, 6H), 0.90 (d, J=6.9 Hz, 6H). $^{13}$C-NMR($C_6D_6$, 75 MHz): δ=204.1, 150.4, 146.0, 145.8, 139.9, 134.6, 132.5, 131.6, 130.2, 128.8, 128.5, 125.0, 124.2, 29.4, 29.3, 25.4, 24.9, 24.5, 23.1.

Example 47

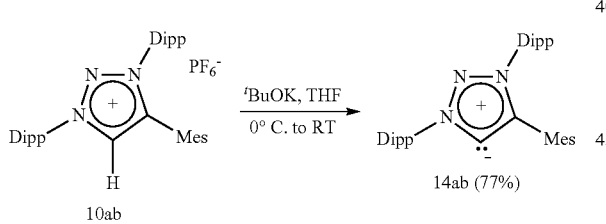

1,3-Bis(2,6-diisopropylphenyl)-4-(2,4,6-trimethylphenyl)-1H-1,2,3-triazol-5-ylidene (14ab). Following the general procedure with 10ab (325 mg, 0.5 mmol), potassium tert-butoxide (112 mg, 1.0 mmol) in THF (10 mL), extraction/tritutation in PhH (20 mL) yields after filtration and evaporation of the volatiles 14ab (196 mg, 77%) as an off-white solid. $^1$H-NMR ($C_6D_6$, 300 MHz): δ=7.36 (t, J=7.9 Hz, 1H), 7.23 (d, J=7.6 Hz, 2H), 7.09 (t, J=7.9 Hz, 1H), 6.94 (d, J=7.7 Hz, 2H), 6.69 (s, 2H), 3.05 (sept, J=6.9 Hz, 2H), 2.70 (sept, J=6.9 Hz, 2H), 2.32 (s, 6H), 2.05 (s, 3H), 1.36 (d, J=6.9 Hz, 6H), 1.26 (d, J=6.9 Hz, 6H), 1.10 (d, J=6.9 Hz, 6H), 0.95 (d, J=6.9 Hz, 6H). $^{13}$C-NMR ($C_6D_6$, 75 MHz): δ=205.8 (C), 148.6 (C), 146.0 (2C), 140.0 (C), 139.2 (C), 138.2 (C), 133.9 (C), 131.1 (CH), 130.2 (CH), 129.5 (CH), 128.9 (C) 124.6 (CH), 124.1 (CH), 29.8 (CH), 29.4 (CH), 26.9 ($CH_3$), 24.7 ($CH_3$), 24.3 ($CH_3$), 22.1 ($CH_3$), 22.0 ($CH_3$), 21.3 ($CH_3$).

Example 48

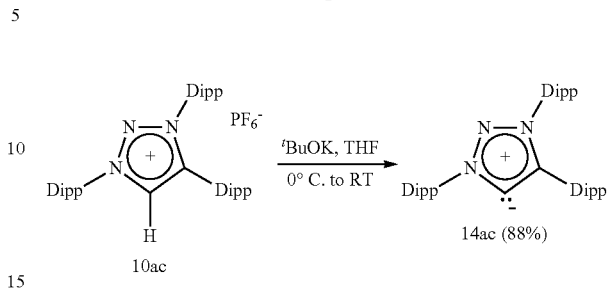

1,3-Tris(2,6-diisopropylphenyl)-1H-1,2,3-triazol-5-ylidene (14ac). Following the general procedure with 10ac (348 mg, 0.5 mmol), potassium tert-butoxide (112 mg, 1.0 mmol) in THF (10 mL), extraction/tritutation in PhMe (20 mL) yields after filtration and evaporation of the volatiles 14ac (241 mg, 88%) as a yellow solid. $^1$H-NMR ($C_6D_6$, 300 MHz): δ=7.34 (dd, J=8.4, 7.0 Hz, 1H), 7.26 (dd, J=8.4, 7.0 Hz, 1H), 7.22 (d, J=7.5 Hz, 2H), 7.14 (d, J=7.0 Hz, 2H), 7.08 (dd, J=8.5, 7.0 Hz, 1H), 6.95 (d, J=7.4 Hz, 2H), 3.06 (sept, J=6.9 Hz, 2H), 2.96 (sept, J=6.9 Hz, 2H), 2.61 (sept, J=6.9 Hz, 2H), 1.37 (d, J=6.9 Hz, 6H), 1.36 (d, J=6.9 Hz, 6H), 1.26 (d, J=6.9 Hz, 6H), 1.09 (d, J=6.9 Hz, 6H), 0.96 (d, J=6.9 Hz, 6H), 0.90 (d, J=6.9 Hz, 6H). $^{13}$C-NMR ($C_6D_6$, 75 MHz): δ=206.3 (C), 149.7 (C), 146.9 (C), 146.0 (C), 146.8 (C), 139.8 (C), 134.1 (C), 130.9 (CH), 130.2 (CH), 130.0 (CH), 129.2 (C) 125.4 (CH), 124.1 (CH), 124.0 (CH), 31.9 (CH), 30.0 (CH), 29.5 (CH), 27.1 ($CH_3$), 26.8 ($CH_3$), 24.9 ($CH_3$), 24.0 ($CH_3$), 22.7 ($CH_3$), 22.1 ($CH_3$).

Example 49

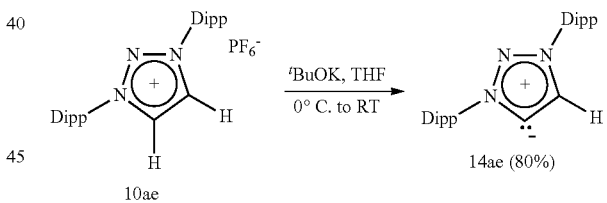

1,3-Bis(2,6-diisopropylphenyl)-1H-1,2,3-triazol-5-ylidene (14ae). Following the general procedure with 10ae (268 mg, 0.5 mmol), potassium tert-butoxide (112 mg, 1.0 mmol) in THF (10 mL), extraction/tritutation in PhH (20 mL) yields after filtration and evaporation of the volatiles 14ae (156 mg, 80%) as a pale yellow solid. The NMR spectra of 14ae shows concentration-dependent broadening/coaleacence, attributed to the exchange of protons at the C4/C5 position. At low concentration in the presence of ~1 equivalent residual PhMe, the spectra of 14ae is clearly asymmetric, but shows some peak broadening, indicative of slow proton exchange at C4/C5 with respect to the NMR timescale. At higher concentrations, the exchange accelerates and the spectra of 14ae becomes symmetric, and displays resonances at the expected mid-point chemical shifts of the low [14ae] resonances. Low concentration of 14ae: $^1$H-NMR ($C_6D_3$, 300 MHz): δ=7.53 (br s, 1H), 7.32 (br m, 1H), 7.20 (br m, 1H), 7.14-7.10 (m, 2H), 7.07-7.00 (m, 2H), 2.94 (br m, 2H), 2.47 (br m, 2H), 1.28 (br m, 6H), 1.23 (br m, 6H), 1.05 (br m, 12H).

¹³C-NMR (C₆D₆, 75 MHz): δ=201.9 (C), 146.0 (C), 145.9 (C), 139.9 (C), 138.4 (CH), 133.9 (C), 131.4 (CH), 130.2 (CH), 124.4 (CH), 124.1 (CH), 29.2 (2 CH), 25.0 (CH₃), 24.8 (CH₃), 24.4 (CH₃), 24.2 (CH₃)

High concentration of 14ae: ¹H-NMR (C₆D₃, 300 MHz): δ=7.56 (br s, 1H), 7.27 (t, J=7.6 Hz, 2H), 7.10 (d, J=7.7 Hz, 4H), 2.70 (br sept, J=6.8 Hz, 4H), 2.47 (br m, 2H), 1.15 (d, J=6.8 Hz, 12H), 1.11 (d, J=6.8 Hz, 12H). ¹³C-NMR (C₆D₆, 75 MHz): δ=~170 (br, C/CH), 145.9 (C), 136.8 (C), 130.8 (CH), 124.3 (CH), 29.2 (CH), 24.9 (CH), 24.2 (CH).

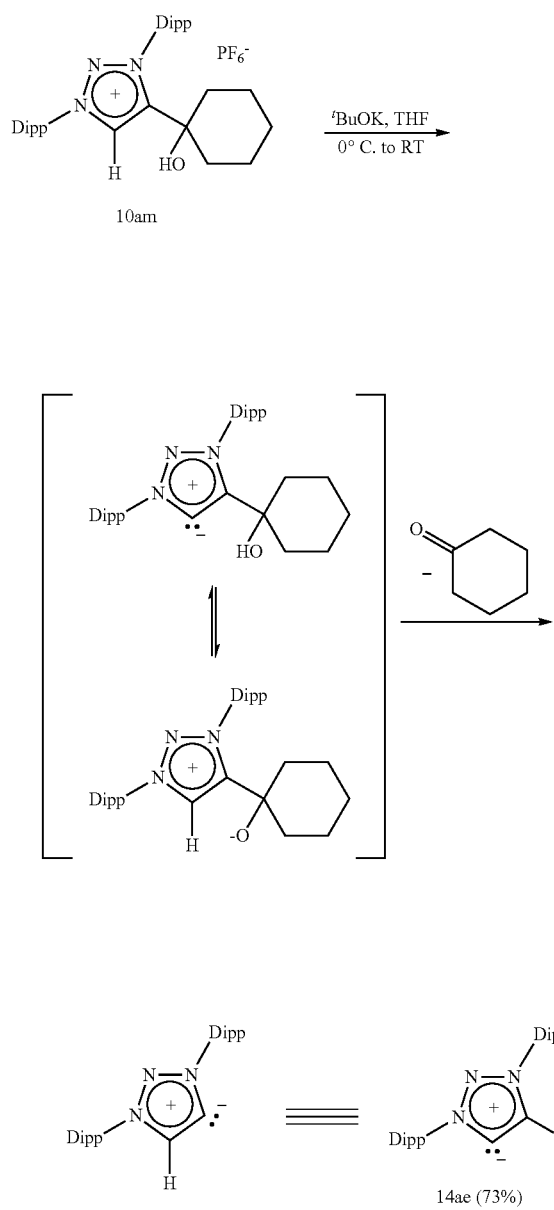

Example 50

1,3-Bis(2,6-diisopropylphenyl)-1H-1,2,3-triazol-5-ylidene (14ae), alternate preparation. Following the general procedure with 10 am (211 mg, 0.33 mmol), potassium tert-butoxide (48 mg, 0.43 mmol) in THF (10 mL), extraction/tritutation in PhH (20 mL) yields after filtration and evaporation of the volatiles 14ae (95 mg, 73%) as a beige solid. Characterization data are identical as for 14ae prepared by the first method.

Example 51

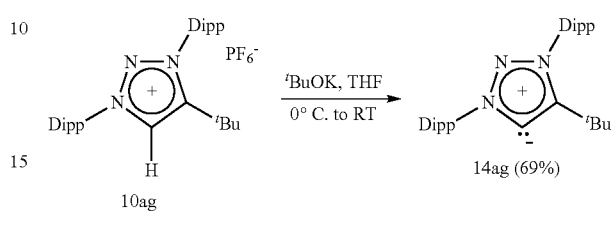

1,3-Bis(2,6-diisopropylphenyl)-4-(tert-butyl)-1H-1,2,3-triazol-5-ylidene (14ag). Following the general procedure with 10ag (197 mg, 0.33 mmol), potassium tert-butoxide (56 mg, 0.5 mmol) in THF (10 mL), extraction/tritutation in PhMe (20 mL) yields after filtration and evaporation of the volatiles 14ag (196 mg, 69%) as an off-white solid. ¹H-NMR (C₆D₃, 300 MHz): δ=7.30 (t, J=7.8 Hz, 1H), 7.24-7.16 (m, 3H), 7.03 (d, J=7.7 Hz, 2H), 2.89 (sept, J=6.9 Hz, 2H), 2.54 (sept, J=6.9 Hz, 2H), 1.47 (s, 9H), 1.32 (d, J=6.9 Hz, 6H), 1.19 (d, J=6.9 Hz, 6H), 1.18 (d, J=6.9 Hz, 6H), 1.11 (d, J=6.9 Hz, 6H). ¹³C-NMR (C₆D₆, 75 MHz): δ=203.0 (C), 158.2 (C), 146.3 (C), 145.7 (C), 140.1 (C), 135.9 (C), 131.3 (CH), 129.9 (CH), 124.2 (CH), 124.0 (CH), 34.2 (C), 32.6 (CH₃), 29.7 (CH), 29.2 (CH), 27.0 (CH₃), 25.1 (CH₃), 24.3 (CH₃), 22.1 (CH₃).

Example 52

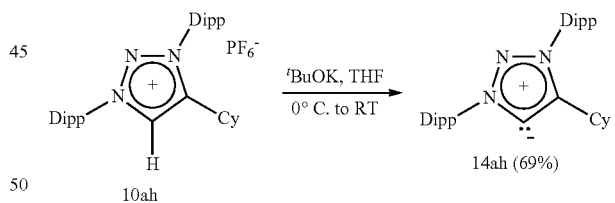

1,3-Bis(2,6-diisopropylphenyl)-4-cyclohexyl-1H-1,2,3-triazol-5-ylidene (14ah). Following the general procedure with 10ah (309 mg, 0.5 mmol), potassium tert-butoxide (112 mg, 1.0 mmol) in THF (10 mL), extraction/tritutation in PhH (20 mL) yields after filtration and evaporation of the volatiles 14ah (162 mg, 69%) as an off-white solid. ¹H-NMR (C₆D₃, 300 MHz): δ=7.31 (t, J=7.8 Hz, 1H), 7.24-7.16 (m, 3H), 7.08 (d, J=7.7 Hz, 2H), 2.97 (sept, J=6.9 Hz, 2H), 2.49 (sept, J=6.9 Hz, 2H), 2.40-2.22 (m, 3H), 1.95 (d, J=11.6 Hz, 2H), 1.75 (d, J=12.9 Hz, 2H), 1.49-1.44 (m, 1H), 1.32 (d, J=6.9 Hz, 6H), 1.21 (d, J=6.9 Hz, 6H), 1.17 (d, J=6.9 Hz, 6H), 1.11 (d, J=6.9 Hz, 6H), 1.11-0.98 (m, 3H). ¹³C-NMR (C₆D₆, 75 MHz): δ=199.8 (C), 155.8 (C), 146.5 (C), 145.7 (C), 140.3 (C), 132.5 (C), 131.4 (CH), 129.9 (CH), 124.6 (CH), 124.0 (CH), 36.4

(CH), 34.9 (CH$_2$), 29.3 (CH), 29.2 (CH), 26.8 (CH$_2$), 26.4 (CH$_2$), 26.1 (CH$_3$), 24.7 (CH$_3$), 24.5 (CH$_3$), 23.3 (CH$_3$).

Example 53

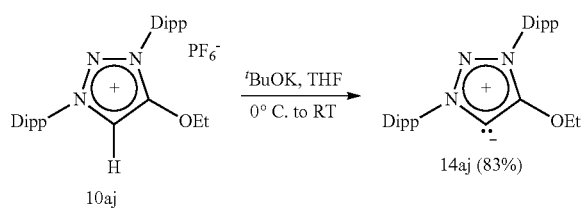

1,3-Bis(2,6-diisopropylphenyl)-4-ethoxy-1H-1,2,3-triazol-5-ylidene (14aj). Following the general procedure with 10aj (290 mg, 0.5 mmol), potassium tert-butoxide (112 mg, 1.0 mmol) in THF (10 mL), extraction/tritutation in PhH (20 mL) yields after filtration and evaporation of the volatiles 14aj (181 mg, 83%) as an off-white solid. $^1$H-NMR (C$_6$D$_3$, 300 MHz): δ=7.34 (dd, J=8.4, 7.2 Hz, 1H), 7.28-7.18 (m, 3H), 7.13 (d, J=7.6 Hz, 2H), 4.70 (q, J=7.0 Hz, 2H), 3.13 (sept, J=6.9 Hz, 2H), 2.80 (sept, J=6.9 Hz, 2H), 1.35 (d, J=6.9 Hz, 6H), 1.27 (d, J=6.9 Hz, 6H), 1.26 (d, J=6.9 Hz, 6H), 1.19 (d, J=6.9 Hz, 6H), 1.17 (t, J=7.0 Hz, 3H). $^{13}$C-NMR (C$_6$D$_6$, 75 MHz): δ=179.6 (C), 161.9 (C), 146.7 (C), 145.7 (C), 140.7 (C), 131.3 (CH), 130.0 (CH), 127.3 (C), 124.4 (CH), 124.0 (CH), 68.8 (CH$_2$), 29.4 (CH), 29.2 (CH), 25.1 (CH$_3$), 24.7 (CH$_3$), 24.4 (CH$_3$), 24.0 (CH$_3$), 15.0 (CH$_3$).

Example 54

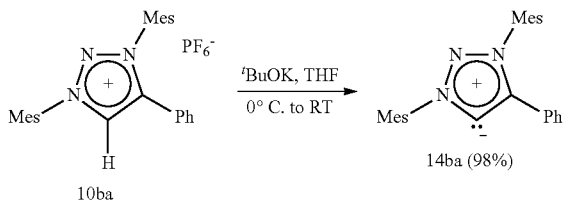

1,3-Bis(2,4,6-trimethylphenyl)-4-phenyl-1H-1,2,3-triazol-5-ylidene (14ba). Following the general procedure with 10ba (3.17 g, 6 mmol), potassium tert-butoxide (840 mg, 7.5 mmol) in THF (40 mL), extraction/tritutation in PhH (2×25 mL) yields after filtration and evaporation of the volatiles 14ba (2.25 g, 98%) as a pale brown solid. $^1$H-NMR (C$_6$D$_3$, 300 MHz): δ=8.07 (d, J=7.3 Hz, 2H), 7.06 (t, J=7.2 Hz, 2H), 6.97 (t, J=7.3 Hz, 1H), 6.81 (s, 2H), 6.62 (s, 2H), 2.27 (s, 6H), 2.14 (s, 3H), 2.01 (s, 3H), 1.86 (s, 6H). $^{13}$C-NMR (C$_6$D$_6$, 75 MHz): δ=201.1 (C), 148.3 (C), 139.3 (C), 138.8 (C), 137.6 (C), 134.0 (C), 133.8 (C), 131.5 (C), 130.1 (CH), 129.6 (CH), 129.1 (CH), 128.6 (CH), 128.0 (CH), 20.3 (CH$_3$), 20.2 (CH$_3$), 17.1 (CH$_3$), 16.5 (CH$_3$). M.p.: 154-156° C. (dec).

Example 55

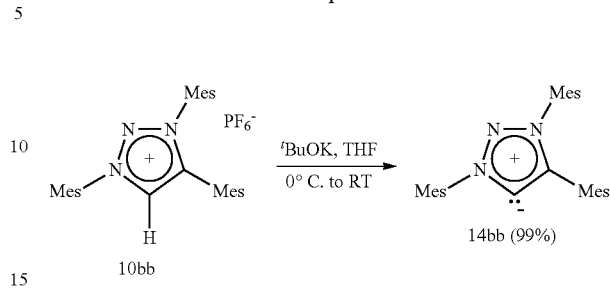

1,3,4-Tris(2,4,6-trimethylphenyl)-1H-1,2,3-triazol-5-ylidene (14bb). Following the general procedure with 10bb (570 mg, 1 mmol), potassium tert-butoxide (168 mg, 1.5 mmol) in THF (15 mL), extraction/tritutation in PhH (20 mL) yields after filtration and evaporation of the volatiles 14bb (420 mg, 99%) as a grey solid. $^1$H-NMR (C$_6$D$_3$, 300 MHz): δ=6.83 (s, 2H), 6.72 (s, 2H), 6.48 (s, 2H), 2.33 (s, 6H), 2.31 (s, 6H), 2.16 (s, 3H), 2.04 (s, 3H), 1.95 (s, 6H), 1.89 (s, 3H). $^{13}$C-NMR (C$_6$D$_6$, 75 MHz): δ=203.2 (C), 148.7 (C), 140.2 (C), 139.7 (C), 139.1 (2C), 138.7 (C), 138.3 (C), 135.1 (C), 135.0 (C), 134.2 (C), 130.1 (CH), 129.6 (2CH), 22.1 (CH$_3$), 21.5 (CH$_3$), 21.4 (CH$_3$), 21.1 (CH$_3$), 19.2 (CH$_3$), 18.3 (CH$_3$). M.p.: 92-94° C. (dec).

Example 56

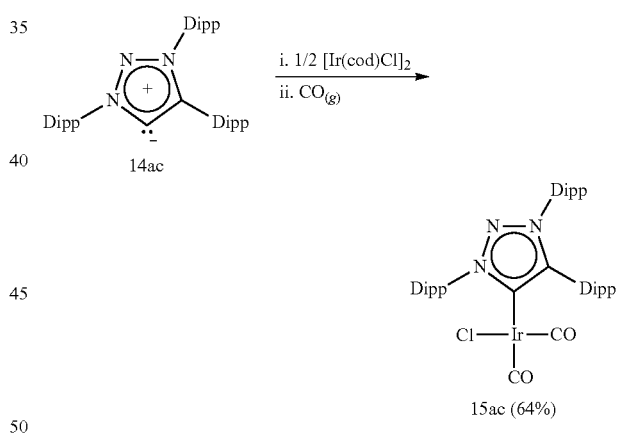

Iridium Complex 15ac. Dry THF (2 mL) is added to a Schlenk flask containing MIC 14ac (55 mg, 0.1 mmol) and [Ir(cod)Cl]$_2$ (34 mg, 0.05 mmol), and the resulting mixture is stirred at room temperature overnight. To the resulting solution is then bubbled CO(g) for 30 minutes, followed by further stirring for ca. 1 hour under a CO atmosphere. Volatiles are evaporated under reduced pressure and the crude product is purified by column chromatography on SiO$_2$ using 3:1 to 1:1 pentane:dichloromethane (v/v) as the mobile phase to afford complex 15ac as a pale yellow solid (53 mg, 64%). Crystals suitable for X-ray study were obtained by the slow vapour diffusion of pentane into a chloroform solution of 15ac. Note: The NMR spectra of 15ac show broadened features indicative of restricted rotation at the NMR timescale. $^1$H-NMR (C$_6$D$_6$, 300 MHz): δ=7.37 (t, J=7.7 Hz, 1H), 7.28-7.21 (m, 3H), 7.14-7.05 (m, 3H), 6.97 (br m, 2H), 3.50-2.25

(br, 4H), 2.50 (sept, J=6.8 Hz), 1.85-1.70 (br m, 12H), 1.55-1.30 (br m, 6H), 1.28-1.17 (br m, 6H), 1.08-0.75 (br m, 12H). $^{13}$C-NMR (CDCl$_3$, 75 MHz): δ=180.9, 172.0 (br), 169.0, 149.4, 147.9, 146.3 (br), 135.5, 132.2, 131.7, 131.5, 130.9, 125.6 (br), 125.1 (br), 124.4 (br), 123.4, 31.5, 29.9, 29.8, 26.5 (br), 23.9, 21.9. IR(CH$_2$Cl$_2$): ν CO 2060.1, 1975.2 cm$^{-1}$ Calcd. for C$_{40}$H$_{51}$ClIrN$_3$O$_2$ [M+Na]: 856.3192. found 856.3172.

Example 57

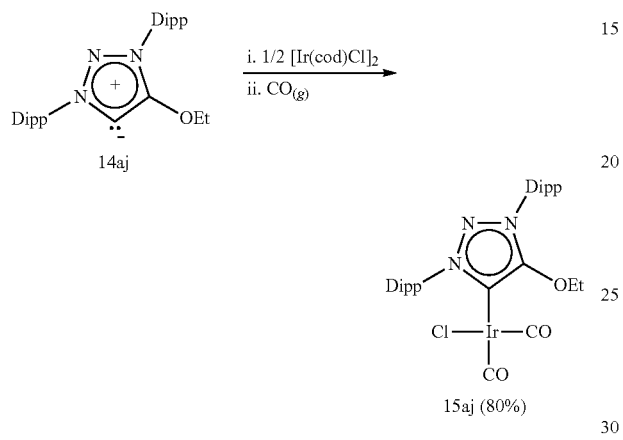

15aj (80%)

Iridium Complex 15aj. Dry THF (10 mL) is added to a Schlenk flask containing MIC 14aj (65 mg, 0.15 mmol) and [Ir(cod)Cl]$_2$ (50 mg, 0.075 mmol), and the resulting mixture is stirred at room temperature for 2 days. To the resulting solution is then bubbled CO(g) for 30 minutes, followed by further stirring for ca. 1 hour under a CO atmosphere. Volatiles are evaporated under reduced pressure and the crude product is purified by column chromatography on SiO$_2$ using 1:1 pentane:dichloromethane (v/v) as the mobile phase to afford complex 15aj as a pale yellow solid (86 mg, 80%). $^1$H-NMR (CDCl$_3$, 300 MHz): δ=7.61-7.54 (m, 2H), 7.35 (d, J=7.8 Hz, 2H), 7.34 (d, J=7.8 Hz, 2H), 4.99 (q, J=7.0 Hz, 2H), 2.67 (sept, J=6.8 Hz), 2.44 (sept, J=6.8 Hz), 1.40 (d, J=6.8 Hz, 6H), 1.33 (t, J=7.0 Hz, 3H), 1.26 (d, J=6.8 Hz, 6H), 1.20 (d, J=6.8 Hz, 6H), 1.10 (d, J=6.8 Hz, 6H). $^{13}$C-NMR (CDCl$_3$, 75 MHz): δ=180.9, 168.8, 159.6, 147.9, 146.3, 145.6, 136.8, 132.1, 131.6, 128.7, 124.4, 124.1, 73.6, 29.9, 29.4, 29.0, 26.7, 24.3, 24.1, 22.7, 15.1. IR (CH$_2$Cl$_2$): νCO 2061.9, 1978.7 cm$^{-1}$ Calcd. for C$_{30}$H$_{39}$ClIrN$_3$O$_3$ [M+Na]: 740.2207. found 740.2193.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A stable mesoionic triazolium carbene compound having the structure of Formula I:

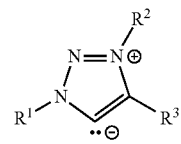

wherein, $R^1$, $R^2$, and $R^3$ are independently selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_3$-$C_{10}$ heterocycloalkyl, optionally substituted aryl, and optionally substituted heteroaryl; and salts thereof.

2. The compound of claim 1 having the structure of Formula II:

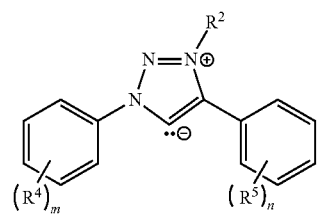

wherein, $R^2$ is selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_3$-$C_{10}$ heterocycloalkyl, optionally substituted aryl, and optionally substituted heteroaryl;

$R^4$ and $R^5$ are, in each instance, independently selected from the group consisting of hydrogen, optionally substituted $C_1$-$C_6$ alkyl, optionally substituted $C_2$-$C_6$ alkenyl, optionally substituted $C_2$-$C_6$ alkynyl, halogen, and hydroxyl;

subscripts m and n are independently integers of from 0 to 5;

and salts thereof.

3. The compound of claim 2 having the structure of Formula III:

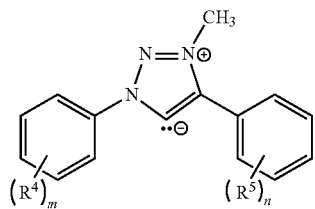

wherein, $R^4$ and $R^5$ are, in each instance, independently selected from the group consisting of hydrogen, optionally substituted $C_1$-$C_6$ alkyl, optionally substituted $C_2$-$C_6$ alkenyl, optionally substituted $C_2$-$C_6$ alkynyl, halogen, and hydroxyl;

subscripts m and n are independently integers of from 0 to 5;

and salts thereof.

4. The compound of claim 2 having the structure of Formula IV:

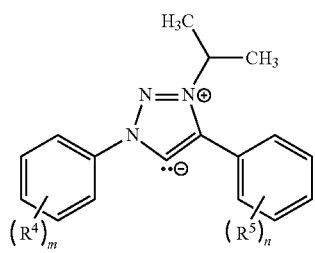

(IV)

wherein,

R$^4$ and R$^5$ are, in each instance, independently selected from the group consisting of hydrogen, optionally substituted C$_1$-C$_6$ alkyl, optionally substituted C$_2$-C$_6$ alkenyl, optionally substituted C$_2$-C$_6$ alkynyl, halogen, and hydroxyl;

subscripts m and n are independently integers of from 0 to 5;

and salts thereof.

5. The compound of claim 1 having the structure of Formula V:

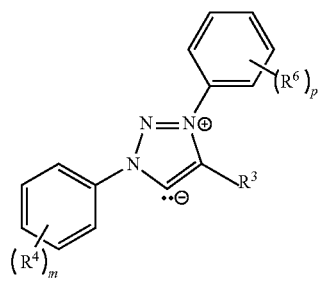

(V)

wherein,

R$^3$ is selected from the group consisting of optionally substituted C$_1$-C$_{10}$ alkyl, optionally substituted C$_2$-C$_{10}$ alkenyl, optionally substituted C$_2$-C$_{10}$ alkynyl, optionally substituted C$_3$-C$_{10}$ cycloalkyl, optionally substituted C$_3$-C$_{10}$ heterocycloalkyl, optionally substituted aryl, and optionally substituted heteroaryl;

R$^4$ and R$^6$ are, in each instance, independently selected from the group consisting of hydrogen, optionally substituted C$_1$-C$_6$ alkyl, optionally substituted C$_2$-C$_6$ alkenyl, optionally substituted C$_2$-C$_6$ alkynyl, halogen, and hydroxyl;

subscripts m and p are independently integers of from 0 to 5;

and salts thereof.

6. The compound of claim 5 having the structure of Formula VI:

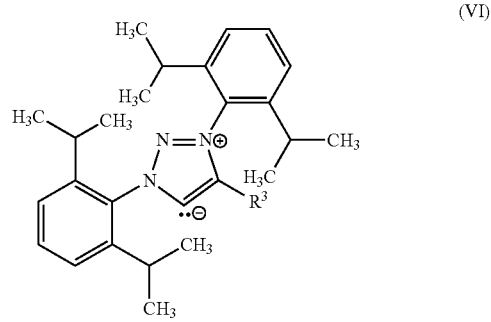

(VI)

wherein,

R$^3$ is selected from the group consisting of optionally substituted C$_1$-C$_{10}$ alkyl, optionally substituted C$_2$-C$_{10}$ alkenyl, optionally substituted C$_2$-C$_{10}$ alkynyl, optionally substituted C$_3$-C$_{10}$ cycloalkyl, optionally substituted C$_3$-C$_{10}$ heterocycloalkyl, optionally substituted aryl, and optionally substituted heteroaryl;

and salts thereof.

7. The compound of claim 5 having the structure of Formula VII:

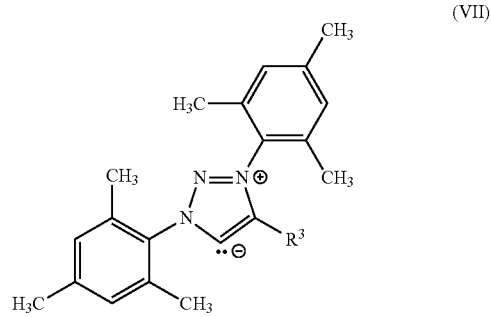

(VII)

wherein,

R$^3$ is selected from the group consisting of optionally substituted C$_1$-C$_{10}$ alkyl, optionally substituted C$_2$-C$_{10}$ alkenyl, optionally substituted C$_2$-C$_{10}$ alkynyl, optionally substituted C$_3$-C$_{10}$ cycloalkyl, optionally substituted C$_3$-C$_{10}$ heterocycloalkyl, optionally substituted aryl, and optionally substituted heteroaryl;

and salts thereof.

8. The compound of any one of claims 2-4, wherein R$^4$ and R$^5$ are, in each instance, independently selected from the group consisting of hydrogen, methyl, ethyl, propyl, isopropyl, butyl, isobutyl, halogen, and hydroxyl.

9. The compound of claim 8, wherein R$^4$ and R$^5$ are both isopropyl and subscripts m and n are both 2.

10. The compound of claim 8, wherein R$^4$ is isopropyl and subscript m is 2.

11. The compound of claim 8, wherein R$^5$ is isopropyl and subscript n is 2.

12. The compound of claim 8, wherein R$^4$ and R$^5$ are both methyl and subscripts m and n are both 3.

13. The compound of claim 8, wherein R$^4$ is methyl and subscript m is 3.

14. The compound of claim 8, wherein R$^5$ is methyl and subscript n is 3.

15. The compound of claim 8, wherein m and n are both 0.

16. The compound of claim 8, wherein m is 0.

17. The compound of claim 8, wherein n is 0.

18. The compound of claim 5, wherein $R^4$ and $R^6$ are both isopropyl and subscripts m and p are both 2.

19. The compound of claim 5, wherein $R^4$ is isopropyl and subscript m is 2.

20. The compound of claim 5, wherein $R^6$ is isopropyl and subscript p is 2.

21. The compound of claim 5, wherein $R^4$ and $R^6$ are both methyl and subscripts m and p are both 3.

22. The compound of claim 5, wherein $R^4$ is methyl and subscript m is 3.

23. The compound of claim 5, wherein $R^6$ is methyl and subscript p is 3.

24. The compound of claim 5, wherein m and p are both 0.

25. The compound of claim 5, wherein m is 0.

26. The compound of claim 5, wherein p is 0.

27. The compound of claim 1 having the structure selected from the group consisting of

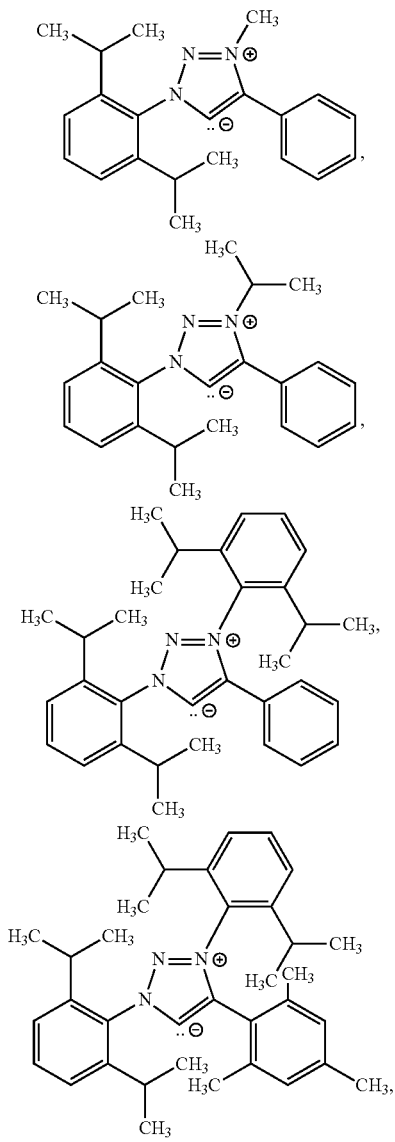

-continued

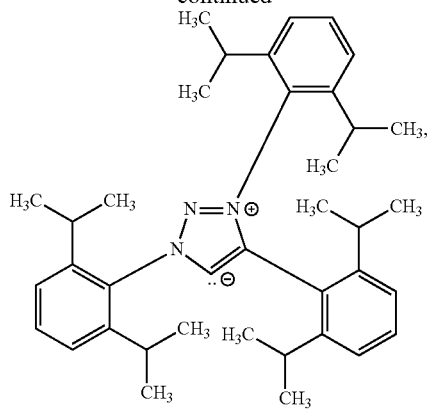

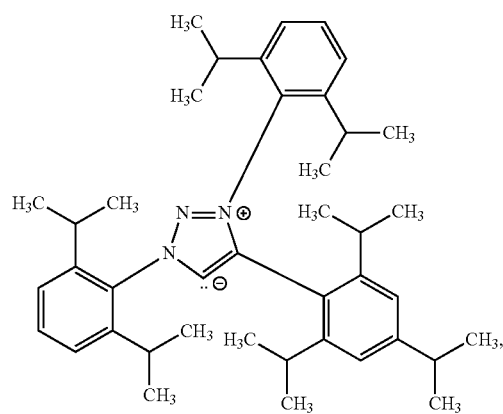

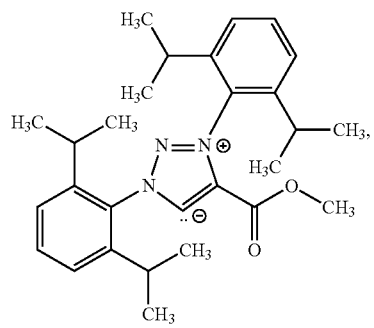

-continued
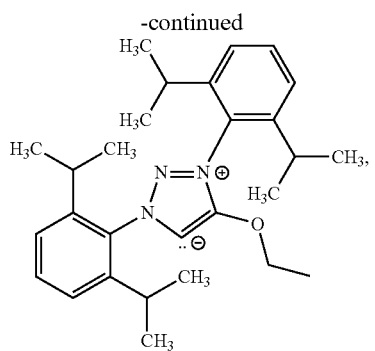
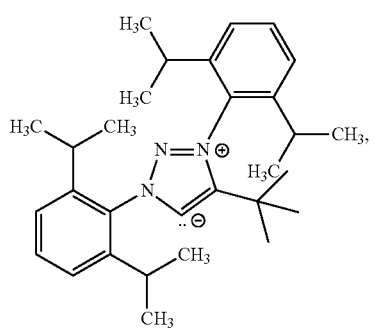
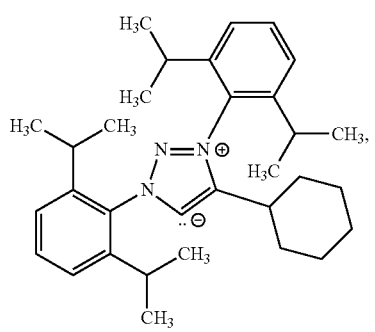
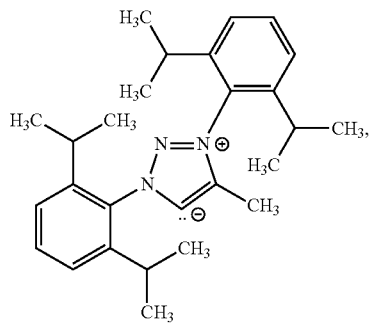
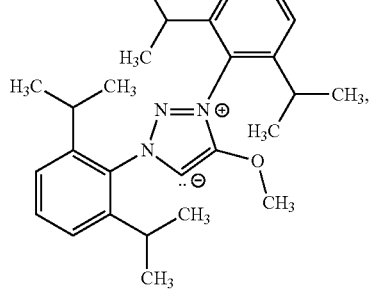
-continued
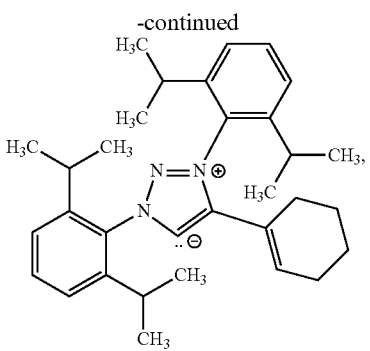
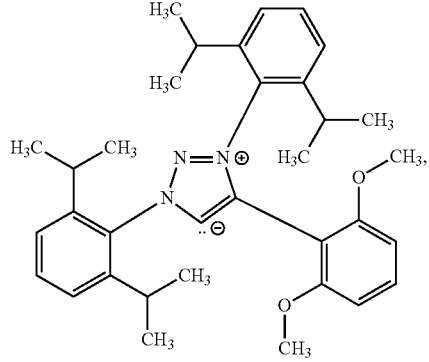
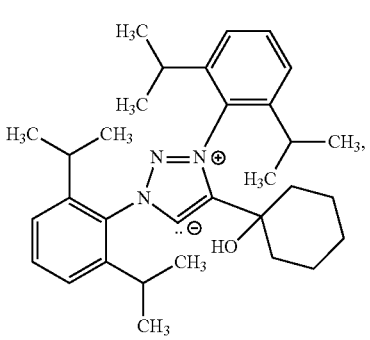
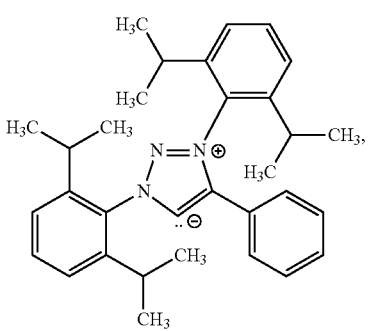
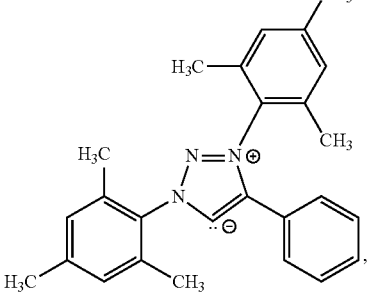

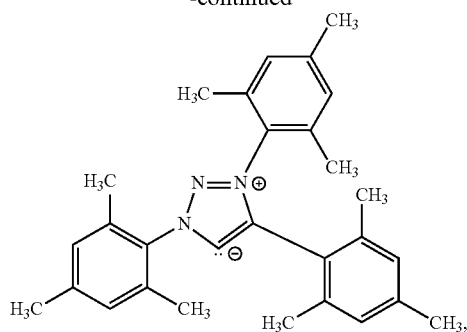
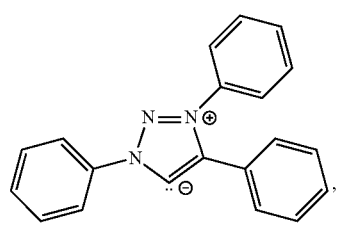
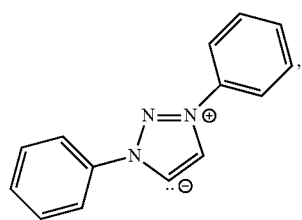
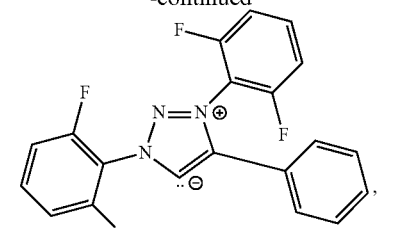
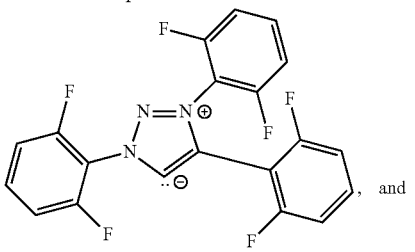
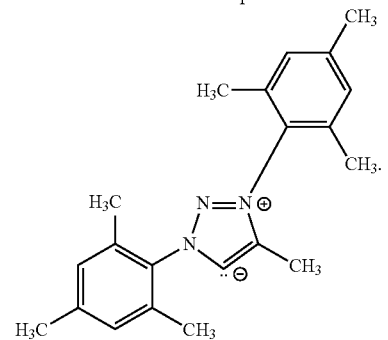
* * * * *